United States Patent
Suzuki et al.

(10) Patent No.: US 7,122,543 B2
(45) Date of Patent: Oct. 17, 2006

(54) SUBSTITUTED BENZOIC ACID DERIVATIVES HAVING NF-κB INHIBITING ACTION

(75) Inventors: Kenji Suzuki, Osaka (JP); Yoichi Nunokawa, Toyonaka (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 308 days.

(21) Appl. No.: 10/416,755

(22) PCT Filed: Sep. 11, 2002

(86) PCT No.: PCT/JP02/09298

§ 371 (c)(1),
(2), (4) Date: May 15, 2003

(87) PCT Pub. No.: WO03/024913

PCT Pub. Date: Mar. 27, 2003

(65) Prior Publication Data

US 2004/0039061 A1 Feb. 26, 2004

(30) Foreign Application Priority Data

Sep. 17, 2001 (JP) .............................. 2001-282255

(51) Int. Cl.
- *A61K 31/235* (2006.01)
- *C07C 50/04* (2006.01)
- *C07C 50/26* (2006.01)
- *C07C 50/28* (2006.01)

(52) U.S. Cl. .................. 514/231.5; 514/277; 514/318; 514/332; 514/544; 544/124; 546/194; 552/293; 552/307

(58) Field of Classification Search ............. 552/293, 552/307; 546/194; 544/124; 514/231.5; 514/277, 318, 332, 544

See application file for complete search history.

(56) References Cited

U.S. PATENT DOCUMENTS 6,156,516 A 12/2000 Nunokawa

FOREIGN PATENT DOCUMENTS

| JP | 7-291859 | 11/1995 |
|----|----------|---------|
| JP | 11-266872 | 3/1998 |
| WO | 99/48491 A1 | 9/1999 |
| WO | 01/21206 A1 | 3/2001 |
| WO | 02/76918 A1 | 10/2002 |

*Primary Examiner*—Barbara P. Badio
(74) *Attorney, Agent, or Firm*—Drinker, Biddle & Reath LLP

(57) ABSTRACT

A substituted benzoic acid derivative which is represented by the following formula (I) and has an NF-κB inhibiting action (in the formula, $R^3$, $R^4$ and $R^5$ each independently represents a hydrogen atom, an alkyl group having 1 to 6 carbon(s) or an alkoxy group having 1 to 6 carbon(s); $R^9$ and $R^{10}$ each independently represents a hydrogen atom, an alkyl group having 1 to 6 carbon(s) or an acyl group having 2 to 11 carbons); $R^2$ represents an optionally-substituted aromatic hydrocarbon group or an optionally-substituted heterocyclic group; and X represents a carboxyl group which may be esterified or amidated)

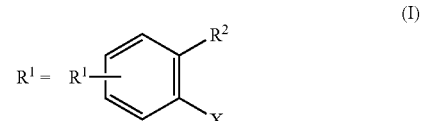

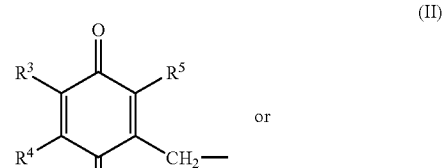

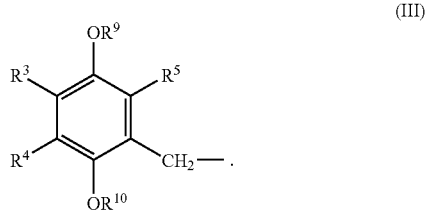

10 Claims, No Drawings

SUBSTITUTED BENZOIC ACID DERIVATIVES HAVING NF-κB INHIBITING ACTION

CROSS REFERENCE TO RELATED APPLICATIONS

This application is a U.S. National Stage application of International Application No. PCT/JP02/09298, filed Sep. 11, 2002, and which claims benefit of Japanese Patent Application 2001-282255, which was filed Sep. 17, 2001, the entire contents of which are hereby incorporated by reference.

TECHNICAL FIELD

The present invention relates to a novel substituted benzoic acid derivative and, more particularly, it relates to a preventive or therapeutic agent for diseases caused by the activation of NF-κB, which is an NF-κB inhibitor containing a substituted benzoic acid derivative or hydroquinone form or a pharmaceutically acceptable salt thereof, as an active ingredient.

BACKGROUND OF THE INVENTION

NF-κB is a protein which regulates the gene expression and is one of the so-called transcription factors. When normal cells are stimulated by an inflammatory cytokine such as interleukin-1 (IL-1) and TNF-α or by lipopolysaccharide, or ultraviolet rays, NF-κB is activated and migrates from the cytosol into the nucleus to bind to its specific nucleotide sequences on the genome DNA and thereby participate in the expression of various genes (Blackwell, T. S. and Christman, J. W. (1997) *Am. J. Respir. Cell. Mol. Biol.,* 17, 3–9).

Among the genes of which the expression is under the control of NF-κB, many genes participate in an immunoinflammatory reaction, such as inflammatory cytokines (e.g., IL-1, IL-6, IL-8 and TNF-α), cell adhesion molecules (e.g., ICAM-1, VCAM-1 and ELAM-1) and inducible NO-synthase (iNOS) (Collins, T., Read, M. A., Neish, A. S., Whitley, M. Z., Thanos, D. and Maniatis, T. (1995) *Faseb. J.,* 9, 899–909). It is further known that, when inflammatory cytokine binds to its receptor, it transmits the signal which activates NF-κB through various pathways and it is believed to be a cause for more exacerbation of inflammation. As such, activation of NF-κB in inflammation is understood as a cause and an exacerbating factor of a diseases (Baeuerle, P. A. and Baichwal, V. R. (1997) *Adv. Immunol.,* 65, 111–137).

Further, it has been reported in recent years that HIV, HTLV-1, CMV, adenovirus, etc. activate NF-κB in host cells (Dezube, B. J., Pardee, A. B., Beckett, L. A., Ahlers, C. M., Ecto, L., Allen-Ryan, J., Anisowicz, Z. A., Sager, R. and Crumpacker, C. S. (1992) *J. Acquir. Immune Defic. Syndr.,* 5, 1099–1104; Nabel, G. and Baltimore, D. (1987) *Nature,* 326, 711–713; Fazely, F., Dezube, B. J., Allen-Ryan, J., Pardee, A. B. and Ruprechet, R. M. (1991) *Blood,* 77, 1653–1656; Munoz, E. and Israel, A. (1995) *Immunobiology,* 193, 128–136) and it is believed that activation of NF-κB participates in self-replication and proliferation of virus in the infected host cells.

Accordingly, when activation of NF-κB is suppressed, it is possible to suppress expression and induction of all of those inflammatory cytokines, cell adhesion molecule gene and virus and suppressors for NF-κB activation is promising as a therapeutic agent for diseases directly or indirectly caused by activation of NF-κB, particularly for various inflammatory diseases and autoimmune diseases, or as a immunosuppressant or as a therapeutic agent for viral diseases.

At present, many anti-inflammatory agents are clinically used for the purpose of treating osteoarthritis, lumbago, rheumatoid arthritis, etc. However, with regard to an agent which suppresses production of various inflammatory cytokines and expression of cell adhesion molecules, no effective one has been available yet. A frequently-used NSAIDs (nonsteroidal anti-inflammatory drugs) suppresses production of prostaglandins by inhibition of cyclooxigenase in a metabolic pathway of arachidonic acid cascade but, generally, they do not directly inhibit the production of cytokines. Although steroids suppress the production of cytokines, they have been known to cause severe adverse actions such as undesirable harmonic action, exacerbation of infectious diseases, generation of peptic ulcer, central action, etc. and therefore not amenable to a long-term administration.

However, among those anti-inflammatory agents, several drugs which suppress the activation of NF-κB by high dose have been reported in recent years (Auphan, N., DiDonato, J. A., Rosette, C., Helmberg, A. and Karin, M. (1995) *Science,* 270, 286–290; Shackelford, R. E., Alford, P. B., Xue, Y., Thai, S. F., Adams, D. O. and Pizzo, S. (1997) *Mol. Pharmacol.,* 52, 421–429; Bitko, V., Valazquez, A., Yang, L., Yang, Y. C. and Barik, S. (1997) *Virology,* 232, 369–378). For example, benzoic acid derivatives such as salicylic acid and aspirin have been reported to suppress the activation of NF-κB (*Science,* 265, 956–959, 1994) but insufficient effect, expression of adverse action caused by various pharmacological actions, etc. have been pointed out as the problems.

Accordingly, there has been a demand for development of medicines which inhibit the activation of NF-κB in more specific manner having higher safety. And investigation and molecular design of inhibitors for NFKB activation have been carried out by many investigators.

In recent years, as inhibitors for activation of NFKB, there have been reported isocarbazole derivatives (JP-A-08-319238; JP-A-2000-169479), isoquinoline derivatives (JP-A-10-87491; JP-A-11-180873), benzoquinone derivatives (JP-A-7-291859; JP-A-11-266872), β-lactam derivatives (JP-A-11-71278), lignan derivatives (JP-A-10175861), benzylidene derivatives (PCT/JP98/04774), pyrimidine-5-carboxamide derivatives (WO97/09315; WO97/09325), cyclopentabenzofuran derivatives (WO00/08007), benzene derivatives (WO00/15603), pyrrolidone dithiocarbonate (PDTC) (*Eur. J. Immunol.* (1999) 29, 1890–1900), 3-deazaadenosine (DZA) (J. Biol. Chem. (1999) 274, 27, 18981–18988), 2,21-bi-1H-pyrrole derivatives (*J. Immunol.* (1999) 162, 7102–7109), etc.

With regard to the action mechanism of those substances for suppressing the activation of NF-κB, there are many ambiguous points but, with respect to substances which are believed to inhibit the activation by antioxidant effects or activities of inhibiting protein phosphorylation, it is believed that stability as a substance or specificity of action will become problems. Further, at the present time, drugs exhibiting a enough potency as an inhibitor for the transcription factor NF-κB.

As an example for the fact that substituted benzoic acid derivatives act on transcription factor and receptor of an transcription factor type, there have been reported that retino-benzoic acid derivatives which are substituted benzoic acid derivatives act on receptors of a transcription factor type such as retinoic acid receptor (RAR) or retinoic acid X receptor (RXR) resulting in agonistic action or antagonistic action (Kagechika H., Kawachi E., Hashimoto Y., Himi T., Shudo K., *J. Med. Chem.,* 1989, 31, 2182; Boehm M. F., Zhang L., Badea B. A., White S. K., Mais D. E., Suto C. M., Goldman M. E., Heyman R. A., *J. Med. Chem.,* 1994, 37, 2930; Boehm M. F., Zhang L., Zhi L. McClurg M. R., Berger E., Wagoner M., Mais D. E., Suto C. M., Davis P. J. A., Heyman R. A., Nadzan A. M., *J. Med. Chem.,* 1995, 38, 3146). However, NF-κB inhibiting activity of those retino-benzoic acid derivatives has not been reported.

On the other hand, in JP-A-7-291859, the following benzoquinone derivative (A) is disclosed as an NF-κB activiation inhibitor.

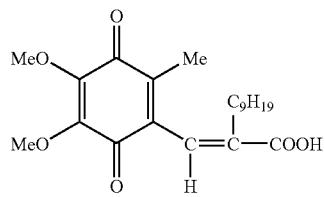

(A)

Further, in JP-A-11-266872, a novel screening method for substances which suppress the activation of NF-κB is disclosed and the following benzoquinone derivative (B) is listed as a substance which suppresses the activation of NF-κB which is able to be found by that method.

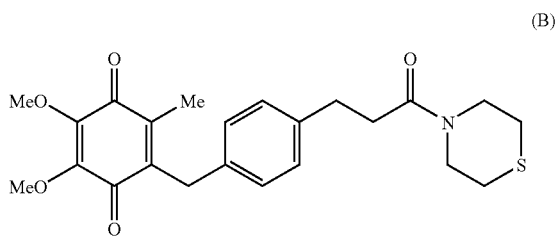

(B)

However, it cannot be said to be a compound having a sufficient effect as an NF-κB inhibiting substance and there has been a demand for investigation of substances having stronger inhibiting activity for NF-κB.

DISCLOSURE OF THE INVENTION

The present invention provides a preventive and therapeutic agent for diseases caused by the activation of NF-κB such as diseases caused by the excess increase of various inflammation mediators or proliferation of virus by inhibiting the activation of Nf-κB. To be more specific, the present invention provides a preventive and therapeutic agent for diseases where an excessive production of NO or TNF-α is believed to be a cause for onset such as septic shock, osteoarthritis, rheumatoid arthritis, cachexia, multiple organ failure, inflammatory bowel diseases, malaria, acquired immune deficiency syndrome, human T-cell leukemia, meningitis, hepatitis, myocarditis, type II diabetes, multiple sclerosis, Behqet's disease, systemic lupus erythematosus and ischemic heart diseases.

The present inventors have carried out earnest investigations for substances which suppress the activation of NF-κB and, as a result, found that novel substituted benzoic acid derivatives represented by the formula (I) or hydroquinone forms thereof or pharmacologically acceptable salts thereof strongly inhibit the activation of NF-κB whereupon the present invention has been achieved.

More specifically, the present invention provides novel substituted benzoic acid derivatives represented by the following formula (I):

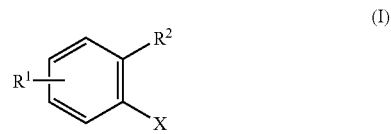

(I)

wherein, $R^1$ represents the following formula (II):

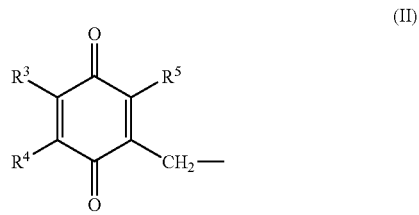

(II)

or the following formula (III):

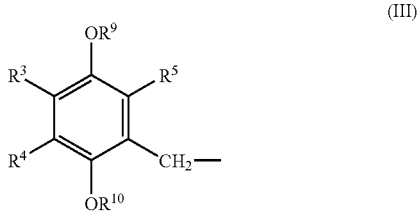

(III)

(wherein $R^3$, $R^4$ and $R^5$ each independently represents hydrogen atom, an alkyl group having 1 to 6 carbon(s) or an alkoxy group having 1 to 6 carbon(s); $R^9$ and $R^{10}$ each independently is hydrogen atom, an alkyl group having 1 to 6 carbon(s) or an acyl group having 2 to 11 carbons);

$R^2$ represents an optionally-substituted aromatic hydrocarbon group or an optionally-substituted heterocyclic group; and X represents a carboxyl group which may be esterified or amidated, NF-κB inhibitors comprising the novel substituted benzoic acid derivatives or hydroquinone forms thereof or pharmaceutically acceptable salts thereof as an active ingredients and to the use of them for a preventive or therapeutic agent for inflammatory diseases, autoimmune diseases and viral diseases and they are used as an inhibitor of gene expression of one or more substance(s) selected from the group consisting of IL-1, TNF-α, IL-2, IL-6, IL-8, iNOS, granulocyte colony-stimulating factor, interferon-γ, ICAM-1, VCAM-1, ELAM-1, major histocompatibility antigen system class I, major histocompatibility antigen system class II, β-2 microglobulin, immunoglobulin light chain, serum amyloid A, angiotensinogen, complement B, complement C4, c-myc, HIV, HTLV-1, SV-40, CMV and adenovirus.

There is also provided a preventive or therapeutic agent for diseases caused by the activation of NF-κB comprising a novel substituted benzoic acid derivative represented by the formula (I) or hydroquinone form thereof or a pharmaceutically acceptable salt thereof as an active ingredient.

When the substituted benzoic acid derivative which is an active ingredient of the present invention has a benzoquinone ring with in the molecule, it can be easily reduced to prepare the corresponding hydroquinone compound. Accordingly, in the present invention, a hydroquinone compound where a benzoquinone ring in a molecule of the substituted benzoic acid derivative of the effective ingredient of the present invention is reduced can be also used as an effective ingredient of the present invention. A hydroquinone compound means a product where the benzoquinone derivative according to the present invention is reduced either chemically using catalyst, etc. or biochemically by enzyme, etc. whereupon oxo group(s) of 1-position and/or 4-position of the benzoquinone ring are/is converted to hydroxyl group(s) or reduced in vivo having an activity equivalent to the benzoquinone derivative.

Examples of the pharmaceutically acceptable salt are salts with inorganic acid such as hydrochloric acid, nitric acid, sulfuric acid, phosphoric acid and hydrobromic acid, organic acid such as maleic acid, fumaric acid, tartaric acid, lactic acid, citric acid, acetic acid, methanesulfonic acid, p-toluenesulfonic acid, adipic acid, palmitic acid and tannic acid, inorganic metal such as alkaline metal including lithium, sodium and potassium and alkaline earth metal including calcium and magnesium and basic amino acid such as lysine.

$R^1$ is the following formula (II):

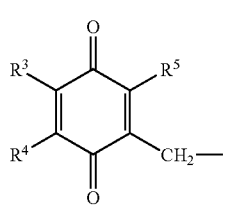

(II)

or the following formula (III):

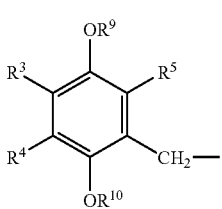

(III)

wherein, $R^3$, $R^4$ and $R^5$ each independently represents a hydrogen atom, an alkyl group having 1 to 6 carbon(s) or an alkoxy group having 1 to 6 carbon(s) and preferred examples of the alkyl group are straight or branched saturated aliphatic hydrocarbon group such as methyl, ethyl, propyl, isopropyl, n-butyl, sec-butyl, tert-butyl, pentyl, isopentyl, neopentyl, tert-pentyl and n-hexyl, saturated alicyclic hydrocarbon group such as cyclopropyl, cyclobutyl, cyclopentyl and cyclohexyl and saturated alicyclic hydrocarbon group-aliphatic hydrocarbon group such as cyclopropylmethyl, cyclopropylethyl and cyclobutylmethyl. The alkoxy group is a group where the above alkyl group is bonded to oxygen atom and preferred examples of the alkoxy group are straight-chain or branched-chain alkoxy group having 1 to 6 carbon(s) such as methoxy, ethoxy, propoxy, isopropoxy, n-butoxy, isobutoxy, sec-butoxy and tert-butoxy.

$R^9$ and $R^{10}$ each independently represents a hydrogen atom, an alkyl group having 1 to 6 carbon(s) or an acyl group having 2 to 11 carbons and preferred examples of the alkyl group are straight or branched saturated aliphatic hydrocarbon group having 1 to 6 carbon(s) such as methyl, ethyl, propyl, isopropyl, n-butyl, sec-butyl, tert-butyl, pentyl, isopentyl, neopentyl, tert-pentyl and n-hexyl, saturated alicyclic hydrocarbon group such as cyclopropyl, cyclobutyl, cyclopentyl and cyclohexyl and saturated alicyclic hydrocarbon group-aliphatic hydrocarbon group such as cyclopropylmethyl, cyclopropylethyl and cyclobutylmethyl. Preferred examples of the acyl group are the groups such as acetyl, propanoyl, butanoyl, cyclopropylcarbonyl, cyclopentylcarbonyl, cyclohexylcarbonyl, benzoyl, 2-pyridinecarbonyl, 3-pyridinecarbonyl and 4-pyridinecarbonyl.

Further, $R^2$ represents an optionally-substituted aromatic hydrocarbon group or an optionally-substituted heterocyclic group and preferred one is an optionally-substituted aryl group having 6 to 12 carbons or an optionally-substituted heteroaryl group having 4 to 11 carbons.

Preferred examples of the optionally-substituted aryl group having 6 to 12 carbons are the groups such as phenyl, 4-methoxyphenyl, 3-methoxyphenyl, 2-methoxyphenyl, 3,4-dimethoxyphenyl, 4-chlorophenyl, 3-chlorophenyl, 2-chlorophenyl, 4-nitrophenyl, 4-cyanophenyl, 4-trifluoromethylphenyl, 2,4-dimethoxyphenyl, 3,4,5-trimethoxyphenyl, 3,4-dichlorophenyl, 4-morphonylphenyl and 1-naphthyl.

Preferred examples of the optionally-substituted heteroaryl group having 4 to 11 carbons are the groups such as 4-pyridyl, 3-pyridyl, 2-pyridyl, 2-furanyl, 3-furanyl, 2-pyrimidyl, 4-pyrimidyl, 2-quinolyl and 3-isoquinolyl.

Specific examples of the substituted which is "optionally substituted" in the present invention are the substituents such as alkyl, alkoxy, aryl, heteroaryl, hydroxyl, acyl, carboxyl, alkoxycarbonyl, aryloxycarbonyl, optionally-substituted carbamoyl, optionally-substituted amino and cyano as well as halogen atom.

X represents a carboxyl group which may be esterified or amidated. Preferred examples of the carboxyl group which may be esterified or amidated include a group —COOR$^6$ (in the formula, R$^6$ represents hydrogen atom, an optionally-substituted lower alkyl group having 1 to 6 carbon(s) or an optionally-substituted aralkyl group having 7 to 14 carbons), a group —CONR$^7$R$^8$ (in the formula, R$^7$ and R$^8$ each independently represents hydrogen atom, an optionally-substituted lower alkyl group having 1 to 6 carbon(s), an optionally-substituted aryl group having 6 to 12 carbons, an optionally-substituted heteroaryl group having 4 to 11 carbons, an optionally-substituted aralkyl group having 7 to 14 carbons or an optionally-substituted heteroarylalkyl group having 5 to 13 carbons or R$^7$ and R$^8$ together with a nitrogen atom bonded thereto mean a heterocyclic group which may further contain nitrogen atom, oxygen atom or sulfur atom or may be fused) or a group —CONR$^7$R$^8$ (in the formula, R$^7$ and R$^8$ together with a nitrogen atom bonded thereto mean a five to eight-membered nitrogen-containing heterocyclic group which may contain 1 to 3 hetero atom(s) selected from nitrogen atom, oxygen atom and sulfur atom where carbon atom or sulfur atom on the ring may be in a form of an oxide).

Preferred examples of the optionally-substituted lower alkyl group having 1 to 6 carbon(s) are the groups such as methyl, ethyl, tert-butyl, hydroxyethyl, alkoxymethyl, aminoethyl, mono- or di-substituted aminoethyl (such as N-methylaminoethyl and N,N-dimethylaminoethyl), cyanomethyl, carboxymethyl, methoxycarbonylmethyl, ethoxycarbonylmethyl and carbamoylmethyl.

Preferred examples of the optionally-substituted aralkyl group are the groups such as benzyl, 4-nitrobenzyl, 3-nitrobenzyl, 4-methoxybenzyl, 3-methoxybenzyl, 4-chlorobenzyl, 2-phenethyl and 3-phenylpropyl.

Preferred examples of the optionally-substituted aryl group having 6 to 12 carbons are the groups such as phenyl, 4-methoxyphenyl, 3-methoxyphenyl, 2-methoxyphenyl, 3,4-dimethoxyphenyl, 3,4,5-trimethoxyphenyl, 4-trifluoromethylphenyl, 4-morpholinophenyl, 4-cyanophenyl, 4-chlorophenyl, 4-nitrophenyl and 1-naphthyl.

Preferred examples of the optionally-substituted heteroaryl group having 4 to 11 carbons are the groups such as 2-pyridyl, 3-pyridyl, 4-pyridyl, 2-furanyl, 2-thienyl, 2-pyrimidinyl, 2-quinolyl and 3-isoquinolyl.

Preferred examples of the optionally-substituted heteroarylalkyl group having 5 to 13 carbons are 4-pyridylmethyl, 3-pyridylmethyl, 2-pyridylmethyl, 2-(pyridin-4-yl)ethyl, 2-(pyridine-3-yl)ethyl, 2-quinolylmethyl and 3-isoquinolylmethyl.

The halogen atom includes fluorine atom, chlorine atom, bromine atom or iodine atom.

Preferred compound in the present invention is a compound represented by the following formula (I):

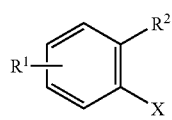

(I)

wherein $R^1$ represents the following formula (II):

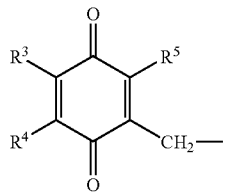

(II)

(wherein $R^3$ and $R^4$ each represents methyl group or methoxy group and $R^5$ is methyl group); $R^2$ represents phenyl group, 4-methoxyphenyl group, 3-methoxyphenyl group, 2-methoxyphenyl group, 3,4-dimethoxyphenyl group, 4-pyridyl group, 3-pyridyl group, 2-pyridyl group, 2-furanyl group or 3-furanyl group; and X represents carboxyl group which may be esterified or amidated. Particularly preferred specific compounds include the following compounds.

Methyl 5-(3,4,5,6-tetramethoxy-2-methylbenzyl)-2-(4-pyridyl)benzoate,
Methyl 5-(3,4,5,6-tetramethoxy-2-methylbenzyl)-2-(3-pyridyl)benzoate,
Methyl 5-(3,4,5,6-tetramethoxy-2-methylbenzyl)-2-phenylbenzoate,
Methyl 5-(3,4,5,6-tetramethoxy-2-methylbenzyl)-2-(4-methoxyphenyl)benzoate,
Methyl 5-(3,4,5,6-tetramethoxy-2-methylbenzyl)-2-(3-methoxyphenyl)benzoate,
Methyl 5-(3,4,5,6-tetramethoxy-2-methylbenzyl)-2-(2-methoxyphenyl)benzoate,
Methyl 3-(3,4,5,6-tetramethoxy-2-methylbenzyl)-2-(3-pyridyl)benzoate,
Methyl 3-(3,4,5,6-tetramethoxy-2-methylbenzyl)-2-(4-pyridyl)benzoate,
Methyl 4-(3,4,5,6-tetramethoxy-2-methylbenzyl)-2-(3-pyridyl)benzoate,
Methyl 4-(3,4,5,6-tetramethoxy-2-methylbenzyl)-2-phenylbenzoate,
5-(3,4,5,6-Tetramethoxy-2-methylbenzyl)-2-(4-pyridyl)benzoic acid,
5-(3,4,5,6-Tetramethoxy-2-methylbenzyl)-2-(3-pyridyl)benzoic acid,
5-(3,4,5,6-Tetramethoxy-2-methylbenzyl)-2-phenyl-benzoic acid,
5-(3,4,5,6-Tetramethoxy-2-methylbenzyl)-2-(4-methoxyphenyl)benzoic acid,
5-(3,4,5,6-Tetramethoxy-2-methylbenzyl)-2-(3-methoxyphenyl)benzoic acid,
5-(3,4,5,6-Tetramethoxy-2-methylbenzyl)-2-(2-methoxyphenyl)benzoic acid,
3-(3,4,5,6-Tetramethoxy-2-methylbenzyl)-2-(3-pyridyl)benzoic acid,
3-(3,4,5,6-Tetramethoxy-2-methylbenzyl)-2-(4-pyridyl)benzoic acid,
N-[4-(3,4,5,6-Tetramethoxy-2-methylbenzyl)-2-(3-pyridyl)benzoyl]piperidine,
N-[4-(3,4,5,6-Tetramethoxy-2-methylbenzyl)-2-(3-pyridyl)benzoyl]morpholine,
N-[4-(3,4,5,6-Tetramethoxy-2-methylbenzyl)-2-(3-pyridyl)benzoyl]-4-trifluoromethylaniline,
4-(3,4,5,6-Tetramethoxy-2-methylbenzyl)-2-(3-pyridyl)benzoic acid,
4-(3,4,5,6-Tetramethoxy-2-methylbenzyl)-2-phenyl-benzoic acid,
N-[5-(3,4,5,6-Tetramethoxy-2-methylbenzyl)-2-(4-pyridyl)benzoyl]piperidine,
N-[5-(3,4,5,6-Tetramethoxy-2-methylbenzyl)-2-(4-pyridyl)benzoyl]morpholine,
N-[5-(3,4,5,6-Tetramethoxy-2-methylbenzyl)-2-(4-pyridyl)benzoyl]-4-trifluoromethylaniline,
N-[3-(3,4,5,6-Tetramethoxy-2-methylbenzyl)-2-(3-pyridyl)benzoyl]piperidine,
(S)-N-[3-(3,4,5,6-Tetramethoxy-2-methylbenzyl)-2-(3-pyridyl)benzoyl]-1-phenylethylamine,
N-[3-(3,4,5,6-Tetramethoxy-2-methylbenzyl)-2-(4-pyridyl)benzoyl]piperidine,
(S)-N-[3-(3,4,5,6-Tetramethoxy-2-methylbenzyl)-2-(4-pyridyl)benzoyl]-1-phenylethylamine,
N-[3-(3,4,5,6-Tetramethoxy-2-methylbenzyl)-2-(4-pyridyl)benzoyl]-4-trifluoromethylaniline,
N-[5-(3,4,5,6-Tetramethoxy-2-methylbenzyl)-2-(3-pyridyl)benzoyl]piperidine,
N-[5-(3,4,5,6-Tetramethoxy-2-methylbenzyl)-2-(3-pyridyl)benzoyl]morpholine,
N-[5-(3,4,5,6-Tetramethoxy-2-methylbenzyl)-2-(3-pyridyl)benzoyl]-4-trifluoromethylaniline,
5-(5,6-Dimethoxy-3-methyl-1,4-benzoquinon-2-yl)-methyl-2-(4-pyridyl)benzoic acid,
5-(5,6-Dimethoxy-3-methyl-1,4-benzoquinon-2-yl)-methyl-2-(3-pyridyl)benzoic acid, 5-(5,6-Dimethoxy-3-methyl-1,4-benzoquinon-2-yl)-methyl-2-phenylbenzoic acid, 5-(5,6-Dimethoxy-3-methyl-1,4-benzoquinon-2-yl)-methyl-2-(4-methoxyphenyl)benzoic acid, 5-(5,6-Dimethoxy-3-methyl-1,4-benzoquinon-2-yl)-methyl-2-(3-methoxyphenyl)benzoic acid, 5-(5,6-Dimethoxy-3-methyl-1,4-benzoquinon-2-yl)-methyl-2-(2-methoxyphenyl)benzoic acid, N-[4-(5,6-Dimethoxy-3-methyl-1,4-benzoquinon-2-yl)-methyl-2-phenylbenzoyl]piperidine, N-[4-(5,6-Dimethoxy-3-methyl-1,4-benzoquinon-2-yl)-methyl-2-phenylbenzoyl]morpholine, N-[4-(5,6-Dimethoxy-3-methyl-1,4-benzoquinon-2-yl)-methyl-2-yl)-phenylbenzoyl]-4-trifluoromethylaniline, N-[4-(5,6-Dimethoxy-3-methyl-1,4-benzoquinon-2-yl)-methyl-2-(3-pyridyl)benzoyl]piperidine, 4-(5,6-Dimethoxy-3-methyl-1,4-benzoquinon-2-yl)-methyl-2-(3-pyridyl)benzoic acid, 4-(5,6-Dimethoxy-3-methyl-1,4-benzoquinon-2-yl)-methyl-2-phenylbenzoic acid, N-[5-(5,6-Dimethoxy-3-methyl-1,4-benzoquinon-2-yl)-methyl-2-(4-pyridyl)benzoyl]piperidine (methanesulfonate), N-[5-(5,6-Dimethoxy-3-methyl-1,4-benzoquinon-2-yl)-methyl-2-(4-pyridyl)benzoyl]morpholine, N-[5-(5,6-Dimethoxy-3-methyl-1,4-benzoquinon-2-yl)-methyl-2-(4-pyridyl)benzoyl]-4-methoxyaniline (hydrochloride), N-[5-(5,6-Dimethoxy-3-methyl-1,4-benzoquinon-2-yl)-methyl-2-(4-pyridyl)benzoyl]-4-trifluoromethylaniline, N-[5-(5,6-Dimethoxy-3-methyl-1,4-benzoquinon-2-yl)-methyl-2-(4-methoxyphenyl)benzoyl]piperidine, N-[5-(5,6-Dimethoxy-3-methyl-1,4-benzoquinon-2-yl)-methyl-2-(4-methoxyphenyl)benzoyl]morpholine, (S)-N-[5-(5,6-Dimethoxy-3-methyl-1,4-benzoquinon-2-yl)methyl-2-(4-pyridyl)benzoyl]-1-phenylethylamine (methanesulfonate), (R)-N-[5-(5,6-Dimethoxy-3-methyl-1,4-benzoquinon-2-yl)methyl-2-(4-pyridyl)benzoyl]-1-phenylethylamine (methanesulfonate), N-[5-(5,6-Dimethoxy-3-methyl-1,4-benzoquinon-2-yl)-methyl-2-(4-pyridyl)benzoyl]cyclohexylamine (methanesulfonate), N-[5-(5,6-Dimethoxy-3-methyl-1,4-benzoquinon-2-yl)-methyl-2-(4-pyridyl)benzoyl]cyclopentylamine (methanesulfonate), N-[5-(5,6-Dimethoxy-3-methyl-1,4-benzoquinon-2-yl)-methyl-2-(4-pyridyl)benzoyl]cyclopropylamine (methanesulfonate), N-[5-(5,6-Dimethoxy-3-methyl-1,4-benzoquinon-2-yl)-methyl-2-(4-pyridyl)benzoyl]-1-ethylpropylamine (methanesulfonate), N-[5-(5,6-Dimethoxy-3-methyl-1,4-benzoquinon-2-yl)-methyl-2-(3-pyridyl)benzoyl]piperidine, N-[5-(5,6-Dimethoxy-3-methyl-1,4-benzoquinon-2-yl)-methyl-2-(3-pyridyl)benzoyl]morpholine, N-[5-(5,6-Dimethoxy-3-methyl-1,4-benzoquinon-2-yl)-methyl-2-(3-pyridyl)benzoyl]-4-methoxyaniline, N-[5-(5,6-Dimethoxy-3-methyl-1,4-benzoquinon-2-yl)-methyl-2-(3-pyridyl)benzoyl]-4-trifluoromethylaniline, N-[5-(5,6-Dimethoxy-3-methyl-1,4-benzoquinon-2-yl)-methyl-2-phenylbenzoyl]-4-methoxyaniline, N-[5-(5,6-Dimethoxy-3-methyl-1,4-benzoquinon-2-yl)-methyl-2-(4-methoxyphenyl)benzoyl]-4-methoxyaniline, N-[5-(5,6-Dimethoxy-3-methyl-1,4-benzoquinon-2-yl)methyl-2-(3-methoxyphenyl)benzoyl]piperidin, N-[5-(5,6-Dimethoxy-3-methyl-1,4-benzoquinon-2-yl)-methyl-2-(3-methoxyphenyl)benzoyl]morpholine, N-[5-(5,6-Dimethoxy-3-methyl-1,4-benzoquinon-2-yl)-methyl-2-(3-methoxyphenyl)benzoyl]-4-methoxyaniline, N-[5-(5,6-Dimethoxy-3-methyl-1,4-benzoquinon-2-yl)-methyl-2-(2-methoxyphenyl)benzoyl]-4-methoxyaniline, N-[3-(5,6-Dimethoxy-3-methyl-1,4-benzoquinon-2-yl)-methyl-2-(3-pyridyl)benzoyl]piperidine, (S)-N-[3-(5,6-Dimethoxy-3-methyl-1,4-benzoquinon-2-yl)-methyl-2-(3-pyridyl)benzoyl]-4-phenylethylamine, N-[3-(5,6-Dimethoxy-3-methyl-1,4-benzoquinon-2-yl)-methyl-2-(4-pyridyl)benzoyl]piperidine, (S)-N-[3-(5,6-Dimethoxy-3-methyl-1,4-benzoquinon-2-yl)-methyl-2-(4-pyridyl)benzoyl]-1-phenylethylamine, N-[3-(5,6-Dimethoxy-3-methyl-1,4-benzoquinon-2-yl)-methyl-2-(4-pyridyl)benzoyl]-4-trifluoromethylaniline, N-[4-(5,6-Dimethoxy-3-methyl-1,4-benzoquinon-2-yl)-methyl-2-(3-pyridyl)benzoyl]morpholine, N-[4-(5,6-Dimethoxy-3-methyl-1,4-benzoquinon-2-yl)-methyl-2-(3-pyridyl)benzoyl]-4-trifluoromethylaniline, N-[4-(5,6-Dimethoxy-3-methyl-1,4-benzoquinon-2-yl)-methyl-2-(3-pyridyl)benzoyl]-4-methoxyaniline, N-[5-(5,6-Dimethoxy-3-methyl-1,4-benzoquinon-2-yl)-methyl-2-phenylbenzoyl]piperidine, N-[5-(5,6-Dimethoxy-3-methyl-1,4-benzoquinon-2-yl)-methyl-2-phenylbenzoyl]morpholine and N-[5-(5,6-Dimethoxy-3-methyl-1,4-benzoquinon-2-yl)-methyl-2-phenylbenzoyl]-4-trifluoroaniline.

Now, examples of a process for the production of the compound for carrying out the present invention will be described. However, the process for the production of the compound which is an active ingredient of the present invention is not limited thereto.

[General Process for Production]

The substituted benzoic acid derivative represented by the formula (I) used as an active ingredient of the present invention can be produced using a synthetic intermediate which is able to be prepared by a method known per se, i.e. a method mentioned in a paper (Suzuki, K., Tatsuoka, T., Ishihara, T., Ogino, R., Miyazaki, T., Satoh, F., Miyano, S., Sumoto, K., *Chem. Pharm. Bull.* (1997) 45, 668–674) or by a method similar to that.

To be more specific, an aldehyde compound represented by the formula (IV):

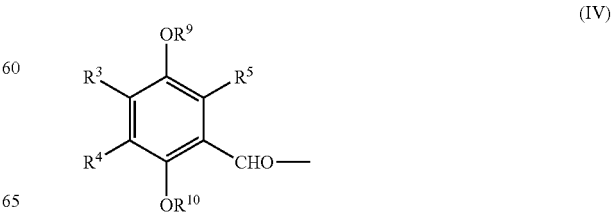

(IV)

wherein $R^3$ to $R^5$, $R^9$ and $R^{10}$ are the same those defined already is allowed to react with an organic lithium reagent or a Grignard reagent prepared from halogenated phenol derivatives to prepare a compound of the formula (V):

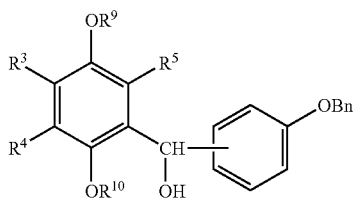

(V)

wherein $R^3$ to $R^5$, $R^9$ and $R^{10}$ are the same those defined already; and Bn is an optionally-substituted benzyl group, and the resulting compound is reduced with a reducing agent such as triethylsilane in the presence of a catalyst such as Lewis acid or trimethylsilyl trifluoromethane sulfonate (TMSOTf) and then subjected to a catalytic reduction by stirring in an atmosphere of hydrogen in the presence of a catalyst such as palladium-carbon to give a phenol derivative represented by the formula (VI):

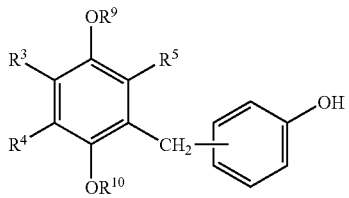

(VI)

wherein $R^3$ to $R^5$, $R^9$ and $R^{10}$ are the same those defined already.

The resulting compound is stirred with hexamethylenetetramine in a solvent such as trifluoroacetic acid at the temperature from room temperature to 100° C. and then hydrolyzed to give a compound of the formula (VIIa):

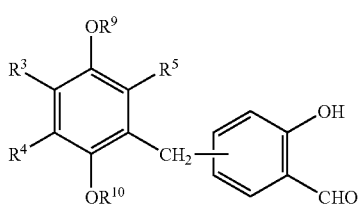

(VIIa)

wherein $R^3$ to $R^5$, $R^9$ and $R^{10}$ are the same as those defined already.

The resulting compound is then stirred at the temperature from 0° C. to refluxing temperature or, preferably, from room temperature to 50° C. with an alkylating agent such as benzyl bromide in the presence of a base such as potassium carbonate or sodium hydroxide in a solvent which does not participate in the reaction such as acetone to give a compound represented by the formula (VIIb):

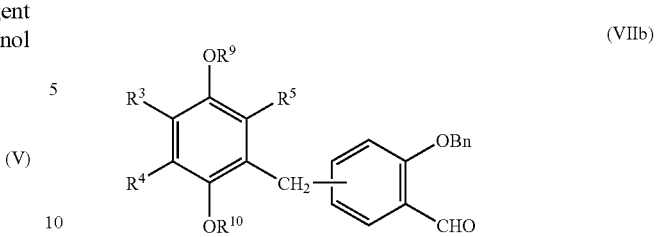

(VIIb)

wherein $R^3$ to $R^5$, $R^9$, $R^{10}$ and Bn are the same those defined already.

The resulting compound is dissolved in a solvent which does not participate in the reaction such as acetonitrile and mixed at the temperature from 0 to 50° C. in the presence of an oxidizing agent such as sodium hypochlorite and hydrogen peroxide in a mixed solution with a phosphate buffer to give a substituted benzoic acid derivative represented by the formula (VIII):

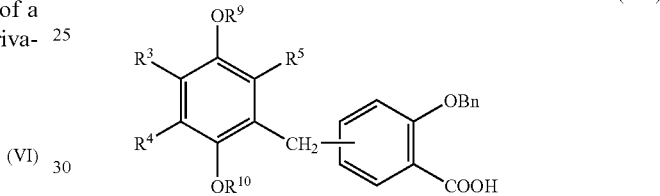

(VIII)

wherein $R^3$ to $R^5$, $R^9$, $R^{10}$ and Bn are the same as those defined already.

Then the resulting compound is treated with diazomethane, trimethylsilyl diazomethane, etc. in a solvent which does not participate in the reaction such as methanol, or treated with a dehydrating condensing agent such as 1-ethyl-3-(3-dimethylaminopropyl) carbodiimide hydrochloride (WSC-HCl) in the presence or absence of a catalyst such as 4-dimethylaminopyridine in a solvent which does not participate in the reaction such as methylene chloride or after converting into an acid chloride using oxalyl chloride, etc, and condensed with an alcohol represented by the formula (IX):

$$R^6\text{—OH} \quad \text{(IX)}$$

wherein $R^6$ is a lower alkyl group having 1 to 6 carbon(s) or an aralkyl group having 7 to 14 carbons. After that, the product is subjected to a catalytic reduction by stirring at from room temperature to 50° C. in a hydrogen atmosphere in the presence of a catalyst such as palladium-carbon in a solvent which does not participate in the reaction such as ethanol or 1,4-dioxane to give a compound represented by the formula (Xa):

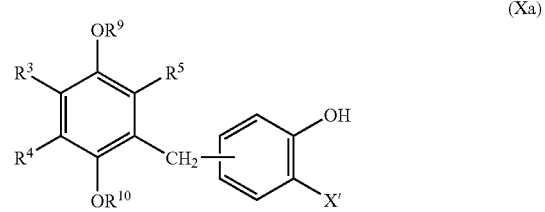

(Xa)

wherein $R^3$ to $R^5$, $R^9$ and $R^{10}$ are the same those defined already and X' represents an esterified carboxyl group.

The compound (Xa) is made to react with trifluoromethanesulfonyl chloride or anhydrous trifluoromethanesulfonic acid under the condition of the presence of a base such as triethylamine in a solvent which does not participate in the reaction such as methylene chloride to give a compound represented by the formula (Xb):

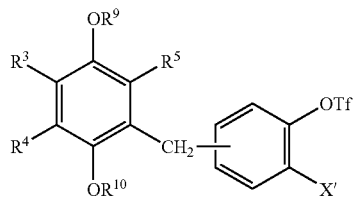

(Xb)

wherein $R^3$ to $R^5$, $R^9$, $R^{10}$ and X' are the same as those defined already.

The compound (Xb) is condensed with a boronic acid derivative represented by the formula (XI):

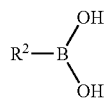

(XI)

wherein $R^2$ represents an optionally substituted aromatic hydrocarbon group or an optionally substituted heterocyclic group, under the condition of the presence of a catalyst such as tetrakis(triphenyl phosphine) palladium in the co-presence of a reagent such as lithium chloride, sodium carbonate or sodium dihydrogen phosphate in a solvent which does not participate in the reaction such as toluene, acetonitrile, 1,4-dioxane, dimethylformamide and water or a mixed solvent thereof or is condensed with an organotin reagent represented by the following formula (XII):

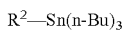

(XII)

wherein $R^2$ represents an optionally substituted aromatic hydrocarbon group or an optionally substituted heterocyclic group, to give a compound represented by the following formula (Ia):

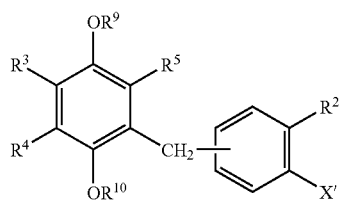

(Ia)

wherein $R^2$ represents an optionally substituted aromatic hydrocarbon group or an optionally substituted heterocyclic group; and $R^3$ to $R^5$, $R^9$, $R^{10}$ and X' are the same as those defined already.

The resulting compound is hydrolyzed by stirring in, for example, a mixed solvent of dioxane and water in the presence of a base such as sodium hydroxide to give a substituted benzoic acid derivative represented by the formula (Ib):

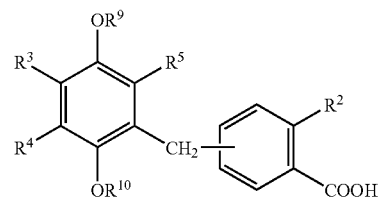

(Ib)

wherein $R^2$, $R^3$ to $R^5$, $R^9$ and $R^{10}$ are the same as those defined already.

The resulting compound is treated with diazomethane or trimethylsilyl diazomethane in a solvent which does not participate in the reaction or is condensed with an alcohol represented by the formula (XIII):

$R^6$—OH  (XIII)

wherein $R^6$ represents a lower alkyl having 1 to 6 carbon(s) or an aralkyl group having 7 to 14 carbons, or with an amine represented by the formula (XIV):

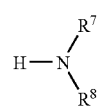

(XIV)

wherein $R^7$ and $R^8$ each independently represents hydrogen atom, an optionally substituted alkyl group having 1 to 6 carbon(s), an optionally substituted aryl group having 6 to 12 carbons, an optionally substituted heteroaryl group having 4 to 11 carbons, an optionally substituted aralkyl group having 7 to 14 carbons or an optionally substituted heteroarylalkyl group having 5 to 13 carbons, or $R^7$ and $R^8$ together with the nitrogen atom binding thereto form a heterocyclic group which may further contained nitrogen atom, oxygen atom or sulfur atom or may be further fused, using a dehydrating condensing agent such as 1-ethyl-3-(3-dimethylaminopropyl) carbodiimide hydrochloride in the presence or absence of a catalyst such as 4-dimethylaminopyridine in a solvent which does not participate in the reaction to give a compound represented by the formula (Ic):

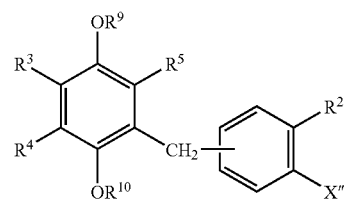

(Ic)

wherein $R^2$, $R^3$ to $R^5$, $R^9$ and $R^{10}$ are the same as those defined already.

When the above compounds (Ia), (Ib) and (Ic) are oxidized with an oxidizing agent such as cerium ammonium nitrate (CAN) in a solvent which does not participate in the reaction such as a mixed solvent of acetonitrile and water to give a benzoquinone derivative represented by the formula (I):

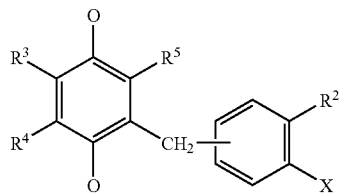

wherein $R^2$, $R^3$ to $R^5$ and X are the same as those defined already.

The compound represented by the formula (I) is able to suppress the activation of NF-κB and, therefore, it can be expected to have a usefulness as a preventive and therapeutic agent for diseases caused by activation of NF-κB such as diseases caused by an excessive production of various inflammatory mediators and proliferation of virus. To be more specific, it is useful as a preventive and therapeutic agent for diseases where an excessive production of NO or TNF-α is believed to be a cause for the onset such as septic shock, osteoarthritis, rheumatoid arthritis, cachexia, multiple organ failure, inflammatory bowel diseases, malaria, acquired immune deficiency syndrome, human T-cell leukemia, meningitis, hepatitis, myocarditis, type II diabetes, multiple sclerosis, Behqet's disease, systemic lupus erythematosus and ischemic heart diseases.

When the compound according to the present invention is used as the above-mentioned medicinal composition, it can be used per os in a dosage form of, for example, tablets, capsules, elixir and microcapsules or used parenterally in a form of an injection agent such as a solution in water or in other pharmaceutically acceptable liquid or as a suspension. For example, it can be manufactured by mixing the compound with physiologically acceptable carriers, flavors, fillers, stabilizers, etc. in a commonly recognized form. With regard to an additive which is able to be mixed with tablets, there may be used a binder such as gelatin, an swelling agent such as corn starch, a filler such as crystalline cellulose, a lubricant such as magnesium stearate, etc. In the case of a dosage form of capsules, the above-mentioned composition may further contain a liquid carrier. In an aseptic composition for injection, common formulations may be adopted as well.

With regard to an aqueous solution for injection, an isotonic solution containing glucose may be exemplified and that may be used together with an appropriate solubilizing aid such as polyethylene glycol. Also, a buffer, a stabilizer, a preservative, an antioxidant and a soothing agent may be mixed. The preparation thus obtained can be administered, for example, to mammals including human being. Although the dosage may vary depending upon symptom, etc., it is usually from about 0.01 to 500 mg, preferably from about 0.1 to 50 mg or, more preferably, from about 1.0 to 25 mg per day for adults in the case of oral administration. When it is administered parenterally, it is usually preferred, in the case of injection for example, to administer from about 0.001 to 50 mg, preferably from about 0.01 to 25 mg or, more preferably, from about 0.1 to 10 mg per day for adults by means of intravenous injection.

The NF-κB inhibiting effect can be examined by measuring the expression of genes regulated by activation of NF-κB either directly or indirectly.

Further, an effect of inhibiting the excessive production of inflammatory proteins can be examined by a direct or indirect measurement of the amount of the inflammatory protein ascending to a culture medium or body fluid by stimulation of cells or animals with cytokines such as IL-1 or TNF-α or lipopolysaccharide. As for a method of confirmating the conventional anti-inflammatory effect in a wide sense, it can be examined by the effect of suppressing the edema induced by carrageenan or dextran.

In those models, it has been confirmed that suppression of production of NO or TNF-α is effective (Filion, M. C. and Phillips, N.C. (1997) *Br. J. Pharmacol.* 122, 551–557; Tsao, P. W., Suzuki, T., Totsuka, R., Murata, T., Takagi, T., Ohmachi, Y., Fujiwara, H., and Takata, I. (1997) *Clin. Immunol. Immunopathol.* (1997) 83, 173–178; Cuzzocrea, S., Zingarelli, B., Hake, P., Salzman, A. L. and Szabo, C. *Free Radic. Biol. Med.* (1998) 24, 450–459).

With regard to more specific diseases, the effect as a therapeutic agent for sepsis can be evaluated by the measurement of the effect for improving the survival rate or the amount of inflammatory cytokine in blood by administration of lipopolysaccharide to animal such as mice. With regard to the effect as a therapeutic agent for rheumatoid arthritis, the pharmaceutical effect can be judged by model animals suffering from arthritis induced by adjuvant or collagen (Y. Iigo, et al., *J. Immunol.,* (1991) 147, 4167.

With regard to the effect as a therapeutic agent for intractable inflammation such as Crohn's disease, hepatitis or nephritis, the pharmaceutical effect can be presumed by animal models prepared by a method which is known per se or by a method similar thereto (K. Nishikawa, et al., *J. Exp. Med.,* (1994) 180, 95; K. Kawasaki, et al., *J. Immunol.,* (1992) 150, 1074). Further, with regard to the effect as a suppressor for rejection by organ transplantation, the pharmaceutical effect can be evaluated by GVH (graft-versus-host) disease or various model animals to which organ is transplanted (A. B. Cosimi, et al., *J. Immunol.,* (1990) 142, 2617; M. Isobe, et al., *Science,* (1992) 255, 1125).

As such, the effect of the NF-κB inhibitor as a therapeutic agent for the disease can be confirmed by various kinds of model animals which are able to be prepared by a known method or a method similar thereto.

The present invention will now be further illustrated by the following Examples and Experimental Examples although the present invention is not limited to those Examples and Experimental Examples.

Reference Example 1

3-(Benzyloxy)bromobenzene

3-Bromophenol (50 g, 0.289 mol) was dissolved in acetone (500 ml), anhydrous potassium carbonate (80 g, 0.580 mmol) and benzyl bromide (59 g, 0.345 mol) were successively added thereto and the mixture was heated to reflux for 3 hours. The reaction mixture was filtered and the filtrate was concentrated under reduced pressure. The resulting crude reaction product was recrystallized (hexane was used as a solvent and the recrystallization operation was carried out twice) to give the title compound (45.0 g, 0.171 mol, 59%).

Reference Example 2

4-(Benzyloxy)bromobenzene

4-Bromophenol (100 g, 0.587 mol) was dissolved in acetone (1100 ml), anhydrous potassium carbonate (159.53 g, 1.156 mmol) and benzyl bromide (103.78 g, 0.607 mol) were successively added thereto and the mixture was heated to reflux for 3 hours. The reaction mixture was filtered and the filtrate was concentrated under reduced pressure. The resulting crude product was recrystallized from hexane to give the title compound (120.76 g, 0.459 mol, 79%).

Reference Example 3

2-(Benzyloxy)bromobenzene

2-Bromophenol (50.0 g, 0.289 mol) was dissolved in acetone (400 ml), anhydrous potassium carbonate (79.89 g, 0.578 mmol) and benzyl bromide (59.32 g, 0.347 mol) were successively added thereto and the mixture was heated to reflux for 3 hours. The reaction mixture was filtered and the filtrate was concentrated under reduced pressure. The resulting crude product was purified by silica gel column chromatography (hexane:AcOEt=95:5) to give the title compound (30.0 g, 0.114 mol, 40%).

Reference Example 4

1-(3,4,5,6-Tetramethoxy-2-methylphenyl)-1-(3-benzyloxyyhenyl)methanol

Under ice-cooling, into a Grignard reagent (150 ml, a tetrahydrofuran solution) prepared from 3-(benzyloxy)bromobenzene (18.4 g, 0.070 mol) and magnesium (1.87 g, 0.077 mol) was dropped a solution of 3,4,5,6-tetramethoxy-2-methylbenzaldehyde (14 g, 0.058 mol) in anhydrous tetrahydrofuran (50 ml) and the mixture was stirred for 2 hours more. The reaction solution was poured into a saturated aqueous solution of ammonium chloride followed by extracting with ether. The extract was washed with a saturated saline and dried. The reaction solution was filtered and the crude product obtained by concentrating the filtrate was purified by silica gel column chromatography (hexane:ethyl acetate=4:1) to give the title compound (23.5 g, 0.055 mol, 95%).

Reference Example 5

1-(3,4,5,6-Tetramethoxy-2-methylphenyl-1-(4-benzoyloxyphenyl)methanol

Under ice-cooling, into a Grignard reagent (30 ml, a tetrahydrofuran solution) prepared from 4-(benzyloxy)bromobenzene (8.00 g, 0.030 mol) and magnesium (0.81 g, 0.033 mol) was dropped a solution of 3,4,5,6-tetramethoxy-2-methylbenzaldehyde (3.65 g, 0.015 mol) in anhydrous tetrahydrofuran (20 ml) and the mixture was stirred for 2 hours more. The reaction solution was poured into a saturated aqueous solution of ammonium chloride followed by extracting with ether. The extract was washed with a saturated saline and dried. The reaction solution was filtered and the crude product obtained by concentrating the filtrate was purified by silica gel column chromatography (hexane:ethyl acetate=4:1) to give the title compound (5.93 g, 0.014 mol, 92%).

Reference Example 6

1-(3,4,5,6-Tetramethoxy-2-methylphenyl)-1-(2-benzyloxyphenyl)methanol

Under ice-cooling, into a Grignard reagent (35 ml, a tetrahydrofuran solution) prepared from 2-(benzyloxy)bromobenzene (11.50 g, 0.044 mol) and magnesium (1.16 g, 0.048 mol) was dropped a solution of 3,4,5,6-tetramethoxy-2-methylbenzaldehyde (5.00 g, 0.021 mol) in anhydrous tetrahydrofuran (30 ml) and the mixture was stirred for 2 hours more. The reaction solution was poured into a saturated aqueous solution of ammonium chloride followed by extracting with ether. The extract was washed with a saturated saline and dried. The reaction solution was filtered and the crude product obtained by concentrating the filtrate was purified by silica gel column chromatography (hexane:ethyl acetate=4:1) to give the title compound (8.80 g, 0.021 mol, 99%).

Reference Example 7

3-13,4,5,6-Tetramethoxy-2-methylbenzyl)phenol

Into a methylene chloride solution (1000 ml) of triethylsilane (8.33 g, 71.64 mmol) and TMSOTf (2.65 g, 11.92 mmol) was dropped a solution of the compound obtained in Reference Example 4 (25.3 g, 59.67 mmol) in methylene chloride followed by stirring at room temperature for 1 hour. The reaction solution was washed with water and dried and the solvent was evaporated therefrom. The residue was dissolved in ethanol (100 ml) and dioxane (150 ml) and added to an ethanolic suspension (50 ml) of 5% Pd—C (3 g) followed by stirring at room temperature for 16 hours in a hydrogen atmosphere. The reaction solution was filtered, the filtrate was concentrated and the resulting residue was purified by silica gel column chromatography (hexane:ethyl acetate=3:1) to give the title compound (18.4 g, 57.9 mmol, 97%).

Reference Example 8

4-(3,4,5,6-Tetramethoxy-2-methylbenzyl)phenol

Into a methylene chloride solution (80 ml) of triethylsilane (0.99 g, 8.52 mmol) and TMSOTf (0.31 g, 1.39 mmol) was dropped a solution of the compound obtained in Reference Example 5 (3.00 g, 7.08 mmol) in methylene chloride (70 ml) followed by stirring at room temperature for 1 hour. The reaction solution was washed with water and dried and the solvent was evaporated therefrom. The residue was dissolved in ethanol (50 ml) and added to an ethanolic suspension (250 ml) of 5% Pd—C (500 mg) followed by stirring at room temperature for 16 hours in a hydrogen atmosphere (In that case, the reaction may be carried out using a mixed solvent of ethanol and dioxane). The reaction solution was filtered, the filtrate was concentrated and the resulting residue was purified by silica gel column chromatography (hexane:ethyl acetate=4:1) to give the title compound (1.96 g, 6.15 mmol, 87%).

Reference Example 9

2-(3,4,5,6-Tetramethoxy-2-methylbenzyl)phenol

Into a methylene chloride solution (150 ml) of triethylsilane (2.95 g, 25.43 mmol) and TMSOTf (0.94 g, 4.23 mmol)

was dropped a solution of the compound obtained in Reference Example 6 (9.00 g, 21.23 mmol) in methylene chloride (130 ml) followed by stirring at room temperature for 1 hour. The reaction solution was washed with water and dried and the solvent was evaporated therefrom. The residue was dissolved in ethanol (50 ml) and added to an ethanolic suspension (350 ml) of 5% Pd—C (1.5 g) followed by stirring at room temperature for 16 hours in a hydrogen atmosphere (In that case, the reaction may be carried out using a mixed solvent of ethanol and dioxane). The reaction solution was filtered, the filtrate was concentrated and the resulting residue was purified by silica gel column chromatography (hexane:ethyl acetate=4:1) to give the title compound (5.67 g, 17.83 mmol, 84%).

Reference Example 10

4-(3,4,5,6-Tetramethoxy-2-methylbenzyl)-2-hydroxybenzaldehyde (10a) and 6-(3,4,5,6-Tetramethoxy-2-methylbenzyl)-2-hydroxybenzaldehyde (10b)

3-(3,4,5,6-Tetramethoxy-2-methylbenzyl)phenol (11.17 g, 35.13 mmol) and hexamethylenetetramine (6.39 g, 0.046 mol) were dissolved in trifluoroacetic acid followed by heating at 80° C. with stirring for 4 hours. After completion of the reaction, the solvent was evaporated therefrom, water was added to the resulting residue and the mixture was stirred for 30 minutes and extracted with methylene chloride. The extract was washed with water and dried, the solvent was evaporated therefrom and the resulting residue was purified by silica gel column chromatography (hexane:ethyl acetate=9:1) to give the title compound 10a (3.35 g, 9.68 mmol, 28%) and 10b (2.03 g, 18%).

Reference Example 11

5-(3,4,5,6-Tetramethoxy-2-methylbenzyl)-2-hydroxybenzaldehyde 4-(3,4,5,6-Tetramethoxy-2-methylbenzyl)phenol (14.5 g, 45.60 mmol) and hexamethylenetetramine (8.30 g, 59.29 mmol) were dissolved in trifluoroacetic acid (100 ml) followed by heating at 80° C. with stirring for 4 hours. After completion of the reaction, the solvent was evaporated therefrom, water (100 ml) was added to the resulting residue and the mixture was stirred for 30 minutes and extracted with methylene chloride. The extract was washed with water and dried, the solvent was evaporated therefrom and the resulting residue was purified by silica gel column chromatography (hexane:ethyl acetate=4:1) to give the title compound (12.20 g, 35.26 mmol, 78%).

Reference Example 12

3-(3,4,5,6-Tetramethoxy-2-methylbenzyl)-2-hydroxybenzaldehyde 2-(3,4,5,6-Tetramethoxy-2-methylbenzyl)phenol (8.64 g, 27.17 mmol) and hexamethylenetetramine (5.00 g, 35.67 mmol) were dissolved in trifluoroacetic acid (100 ml) followed by heating at 80° C. with stirring for 4 hours. After completion of the reaction, the solvent was evaporated therefrom, water (100 ml) was added to the resulting residue and the mixture was stirred for 30 minutes and extracted with methylene chloride. The extract was washed with water and dried, the solvent was evaporated therefrom and the resulting residue was purified by silica gel column chromatography (hexane:ethyl acetate=4:1) to give the title compound (2.50 g, 7.23 mmol, 27%).

Reference Example 13

4-(3,4,5,6-Tetramethoxy-2-methylbenzyl)-2-benzyloxybenzaldehyde 4-(3,4,5,6-Tetramethoxy-2-methylbenzyl)-2-hydroxybenzaldehyde (743 mg, 2.14 mmol) was dissolved in acetone (50 ml) and, after addition of anhydrous sodium carbonate (593 mg, 4.30 mmol) and benzyl bromide (477 mg, 2.79 mmol), the mixture was stirred at room temperature for 16 hours. The reaction solution was filtered and the residue obtained by concentration of the filtrate was purified by silica gel column chromatography (hexane:ethyl acetate=3:1) to give the title compound (864 mg, 1.98 mmol, 93%).

Reference Example 14

5-(3,4,5,6-Tetramethoxy-2-methylbenzyl)-2-benzyloxybenzaldehyde 5-(3,4,5,6-Tetramethoxy-2-methylbenzyl)-2-hydroxybenzaldehyde (0.100 g, 0.290 mol) was dissolved in acetone (10 ml) and, after addition of anhydrous sodium carbonate (0.080 g, 0.579 mmol) and benzyl bromide (0.059 g, 0.347 mmol), the mixture was heated to reflux for 3 hours. The reaction solution was filtered and the residue obtained by concentration of the filtrate was purified by silica gel column chromatography (hexane:ethyl acetate=4:1) to give the title compound (0.114 g, 0.261 mmol, 90%).

Reference Example 15

3-(3,4,5,6-Tetramethoxy-2-methylbenzyl)-2-benzyloxybenzaldehyde 3-(3,4,5,6-Tetramethoxy-2-methylbenzyl)-2-hydroxybenzaldehyde (1.16 g, 3.35 mol) was dissolved in acetone (5.0 ml) and, after addition of anhydrous sodium carbonate (1.02 g, 7.38 mmol) and benzyl bromide (0.69 g, 4.02 mmol), the mixture was heated to reflux for 3 hours. The reaction solution was filtered and the residue obtained by concentration of the filtrate was purified by silica gel column chromatography (hexane:ethyl acetate=2:1) to give the title compound (1.45 g, 3.32 mmol, 99%).

Reference Example 16

4-(3.4.5.6-Tetramethoxy-2-methylbenzyl)-2-benzyloxybenzoic acid

To a solution of 4-(3,4,5,6-tetramethoxy-2-methylbenzyl)-2-benzyloxybenzaldehyde (735 mg, 1.69 mmol) in acetonitrile (5 ml) were added an aqueous solution (2 ml) of sodium dihydrogen phosphate (157 mg, 1.31 mmol), an aqueous solution (7 ml) of sodium hypochlorite (795 mg, 80%, 7.07 mmol) and an aqueous hydrogen peroxide (0.5 ml, 30%) and the mixture was stirred at room temperature for 16 hours. The reaction solution was diluted with water and extracted with ethyl acetate. The extract was washed with a 10% aqueous solution of sodium hydrosulfite ($Na_2S_2O_4$) and a saturated saline, dried and concentrated to give the title compound (603 mg, 1.33 mmol, 79%).

Reference Example 17

5-(3,4,5,6-Tetramethoxy-2-methylbenzyl)-2-benzyloxybenzoic acid

To a solution of 5-(3,4,5,6-tetramethoxy-2-methylbenzyl)-2-benzyloxybenzaldehyde (5.60 g, 0.0128 mol) in acetonitrile (30.0 ml) were added an aqueous solution (10.0 ml) of sodium dihydrogen phosphate (12.0 g, 0.100 mol), an aqueous solution (30.0 ml) of sodium hypochlorite (5.19 g, 0.0577 mol) and an aqueous hydrogen peroxide (1.701 ml, 30%) and the mixture was stirred at room temperature for 5 hours. The reaction solution was diluted with water and extracted with ethyl acetate. The extract was washed with a saturated aqueous solution of sodium hydrosulfite ($Na_2S_2O_4$) and a saturated saline, dried and concentrated to give the title compound (5.20 g, 0.0115 mol, 90%).

Reference Example 18

3-(3,4,5,6-Tetramethoxy-2-methylbenzyl)-2-benzyloxybenzoic acid

To a solution of 3-(3,4,5,6-tetramethoxy-2-methylbenzyl)-2-benzyloxybenzaldehyde (1.87 g, 4.28 mmol) in acetonitrile (12.0 ml) were added an aqueous solution (7.0 ml) of sodium dihydrogen phosphate (4.01 g, 33.42 mmol), an aqueous solution (7.0 ml) of sodium hypochlorite (1.74 g, 19.33 mmol) and an aqueous hydrogen peroxide (1.89 ml, 30%) and the mixture was stirred at room temperature for 5 hours. The reaction solution was diluted with water and extracted with ethyl acetate. The extract was washed with a saturated aqueous solution of sodium hydrosulfite ($Na_2S_2O_4$) and a saturated saline, dried and concentrated to give the title compound (1.90 g, 4.20 mmol, 98%).

Reference Example 19

Methyl 4-(3,4,5,6-tetramethoxy-2-methylbenzyl)-2-benzyloxybenzoate 4-(3,4,5,6-Tetramethoxy-2-methylbenzyl)-2-benzyloxybenzoic acid (525 mg, 1.1615 mmol) was dissolved in methanol (20 ml), trimethylsilyl diazomethane (15.9 g, 10% solution in hexane, 13.9473 mmol) was added thereto under cooling with ice and the mixture was stirred at room temperature for 2 hours. To the reaction solution was added acetic acid (2 ml) and the mixture was allowed to stand so as to decompose an excessive reagent. The reaction solution was concentrated to give the title compound (530 mg, 1.1373 mmol, 98%).

Reference Example 20

Methyl 5-(3,4,5,6-tetramethoxy-2-methylbenzyl)-2-benzyloxybenzoate 5-(3,4,5,6-Tetramethoxy-2-methylbenzyl)-2-benzyloxybenzoic acid (1.22 g, 2.6548 mmol) was dissolved in methanol (100 ml), trimethylsilyl diazomethane (36.3 g, 10% solution in hexane, 31.8421 mmol) was added thereto under cooling with ice and the mixture was stirred at room temperature for 2 hours. To the reaction solution was added acetic acid (0.5 ml) and the mixture was allowed to stand at room temperature for 16 hours so as to decompose an excessive reagent. The residue obtained by concentration of the reaction solution was purified by silica gel column chromatography (hexane:ethyl acetate=4:1) to give the title compound (1.18 g, 2.5321 mmol, 95%).

Reference Example 21

Methyl 3-(3,4,5,6-tetramethoxy-2-methylbenzyl)-2-benzyloxybenzoate 3-(3,4,5,6-Tetramethoxy-2-methylbenzyl)-2-benzyloxybenzoic acid (652 mg, 1.4424 mmol) was dissolved in methylene chloride (20 ml), then anhydrous methanol (231 mg, 7.2187 mmol), 4-dimethylaminopyridine (264 mg, 2.1639 mmol) and WSC-HCl (830 mg, 4.3296 mmol) were added thereto and the mixture was stirred at room temperature for 16 hours. The reaction solution was washed with water and dried and the solvent was evaporated therefrom. The residue was purified by silica gel column chromatography (hexane:ethyl acetate=4:1) to give the title compound (490 mg, 1.0515 mmol, 73%).

Reference Example 22

Methyl 4-(3,4,5,6-tetramethoxy-2-methylbenzyl)-2-hydroxybenzoate

Methyl 4-(3,4,5,6-tetramethoxy-2-methylbenzyl)-2-benzyloxybenzoate (530 mg, 1.1373 mmol) was dissolved in methanol (20 ml), added to a methanolic suspension (20 ml) of 10% palladium-carbon (100 mg) and stirred for 16 hours at room temperature in a hydrogen atmosphere. The reaction solution was filtered and the filtrate was concentrated under reduced pressure to give the title compound (414 mg, 1.101 mmol, 97%).

Reference Example 23

Methyl 5-(3,4,5,6-tetramethoxy-2-methylbenzyl)-2-hydroxybenzoate

Methyl 5-(3,4,5,6-tetramethoxy-2-methylbenzyl)-2-benzyloxybenzoate (15.0 g, 32.1459 mmol) was dissolved in methanol (200 ml), added to a methanolic suspension (200 ml) of 10% palladium-carbon (1.0 g) and stirred for 16 hours at room temperature in a hydrogen atmosphere. The reaction solution was filtered and the filtrate was concentrated under reduced pressure to give the title compound (11.2 g, 29.7340 mmol, 92%).

Reference Example 24

Methyl 3-(3,4,5,6-tetramethoxy-2-methylbenzyl)-2-hydroxybenzoate

Methyl 3-(3,4,5,6-tetramethoxy-2-methylbenzyl)-2-benzyloxybenzoate (343 mg, 0.7360 mmol) was dissolved in methanol (10 ml), added to a methanolic suspension (40 ml) of 10% palladium-carbon (100 mg) and stirred for 16 hours at room temperature in a hydrogen atmosphere. The reaction solution was filtered and the filtrate was concentrated under reduced pressure to give the title compound (223 mg, 0.5930 mmol, 81%).

Reference Example 25

Methyl 4-(3,4,5,6-tetramethoxy-2-methylbenzyl)-2-(trifluoromethanesulfonyl)oxybenzoate To a solution of methyl 4-(3,4,5,6-tetramethoxy-2-methylbenzyl)-2-hydroxybenzoate (175 mg, 0.4654 mmol) in anhydrous methylene chloride (10 ml) were added 4-dimethylaminopyridine (77 mg, 0.6311 mmol), triethylamine (85 mg, 0.8415 mmol) and trifluoromethanesulfonic acid anhydride (177 mg, 0.6276 mmol) and the mixture was stirred for 3 hours under cooling with ice. The reaction solution was washed with water and dried and the solvent was evaporated therefrom. The residue was purified by silica gel column chromatography (hexane:ethyl acetate=6:1) to give the title compound (160 mg, 0.3149 mmol, 68%).

Reference Example 26

Methyl 5-(3,4,5,6-tetramethoxy-2-methylbenzyl)-2-(trifluoromethanesulfonyl)oxybenzoate To a solution of methyl 5-(3,4,5,6-tetramethoxy-2-methylbenzyl)-2-hydroxybenzoate (3.10 g, 8.2446 mmol) in anhydrous methylene chloride (200 ml) were added 4-dimethylaminopyridine (1.51 g, 12.377 mmol), triethylamine (1.67 g, 16.5346 mmol) and trifluoromethanesulfonic acid anhydride (3.49 g, 12.3758 mmol) and the mixture was stirred for 3 hours under cooling with ice. The reaction solution was washed with water and dried and the solvent was evaporated therefrom. The residue was purified by silica gel column chromatography (hexane:ethyl acetate=6:1) to give the title compound (4.06 g, 7.9921 mmol, 97%).

Reference Example 27

Methyl 3-(3,4,5,6-tetramethoxy-2-methylbenzyl)-2-(trifluoromethanesulfonyl)oxybenzoate To a solution of methyl 3-(3,4,5,6-tetramethoxy-2-methylbenzyl)-2-hydroxybenzoate (540 mg, 1.4361 mmol) in anhydrous methylene chloride (30 ml) were added 4-dimethylaminopyridine (263 mg, 2.1557 mmol), triethylamine (290 mg, 2.8712 mmol) and trifluoromethanesulfonic acid anhydride (607 mg, 2.1524 mmol) and the mixture was stirred for 3 hours under cooling with ice. The reaction solution was washed with water and dried and the solvent was evaporated therefrom. The residue was purified by silica gel column chromatography (hexane:ethyl acetate=6:1) to give the title compound (701 mg, 1.3799 mmol, 96%).

EXAMPLE 1

Methyl 4-(3,4,5,6-tetramethoxy-2-methylbenzyl)-2-phenylbenzoate

To a solution of methyl 4-(3,4,5,6-tetramethoxy-2-methylbenzyl)-2-(trifluoromethanesulfonyl)oxybenzoate (102 mg, 0.2007 mmol) in toluene (2.3 ml) were added tetrakistriphenylphosphine palladium (4.6 mg, 0.0039 mmol), aqueous solution of sodium carbonate (2M aqueous solution, 0.35 ml), lithium chloride (17 mg, 0.4010 mmol) and ethanolic solution (1.0 ml) of benzene boronic acid (27 mg, 0.2214 mmol) and the mixture was heated with stirring at 95° C. for 16 hours. The reaction solution was diluted with ethyl acetate (100 ml), washed with water and dried and the solvent was evaporated therefrom. The residue was purified by silica gel column chromatography (hexane:ethyl acetate=6:1) to give the title compound (84 mg, 0.1926 mmol, 96%).

EXAMPLE 2

Methyl 4-(3,4,5,6-tetramethoxy-2-methylbenzyl)-2-(3-pyridyl)benzoate

To a solution of methyl 4-(3,4,5,6-tetramethoxy-2-methylbenzyl)-2-(trifluoromethanesulfonyl)oxybenzoate (333 mg, 0.6555 mmol) in toluene (6 ml) were added tetrakistriphenylphosphine palladium (23 mg, 0.0199 mmol), aqueous solution of sodium carbonate (2M aqueous solution, 1.00 ml), lithium chloride (56 mg, 1.3241 mmol) and ethanolic solution (1.3 ml) of pyridine-3-boronic acid 1,3-propanediol cyclic ester (159 mg, 0.9814 mmol) and the mixture was heated with stirring at 95° C. for 16 hours. The reaction solution was diluted with ethyl acetate (100 ml), washed with water and dried and the solvent was evaporated therefrom. The residue was purified by silica gel column chromatography (hexane:ethyl acetate=1:1) to give the title compound (284 mg, 0.6498 mmol, 99%).

EXAMPLE 3

Methyl 5-(3,4,5,6-tetramethoxy-2-methylbenzyl)-2-phenylbenzoate

To a solution of methyl 5-(3,4,5,6-tetramethoxy-2-methylbenzyl)-3-(trifluoromethanesulfonyl)oxybenzoate (444 mg, 0.8740 mmol) in toluene (12 ml) were added tetrakistriphenylphosphine palladium (60 mg, 0.0519 mmol), aqueous solution of sodium carbonate (2M aqueous solution, 1.35 ml), lithium chloride (89 mg, 2.0995 mmol) and ethanolic solution (2.1 ml) of benzeneboronic acid (320 mg, 2.6244 mmol) and the mixture was heated with stirring at 95° C. for 16 hours. The reaction solution was diluted with ethyl acetate (100 ml), washed with water and dried and the solvent was evaporated therefrom. The residue was purified by silica gel column chromatography (hexane:ethyl acetate=5:1) to give the title compound (349 mg, 0.8004 mmol, 68%).

EXAMPLE 4

Methyl 5-(3,4,5,6-tetramethoxy-2-methylbenzyl)-2-(3-pyridyl)benzoate

To a solution of methyl 5-(3,4,5,6-tetramethoxy-2-methylbenzyl)-2-(trifluoromethanesulfonyl)oxybenzoate (1.43 g, 2.8149 mmol) in toluene (32 ml) were added tetrakistriphenylphosphine palladium (98 mg, 0.0848 mmol), aqueous solution of sodium carbonate (2M aqueous solution, 3.66 ml), lithium chloride (239 mg, 5.6381 mmol) and ethanolic solution (5.9 ml) of pyridine-3-boronic acid 1,3-propanediol cyclic ester (684 mg, 4.2222 mmol) and the mixture was heated with stirring at 95° C. for 16 hours. The reaction solution was diluted with ethyl acetate (200 ml), washed with water and dried and the solvent was evaporated therefrom. The residue was purified by silica gel column chromatography (hexane:ethyl acetate=1:1) to give the title compound (1.20 g, 2.7459 mmol, 98%).

EXAMPLE 5

Methyl 5-(3,4,5,6-tetramethoxy-2-methylbenzyl)-2-(4-pyridyl)benzoate

To a solution of methyl 5-(3,4,5,6-tetramethoxy-2-methylbenzyl)-2-(trifluoromethanesulfonyl)oxybenzoate (1.43 g, 2.8149 mmol) in toluene (32 ml) were added tetrakistriphenylphosphine palladium (98 mg, 0.0848 mmol), aqueous solution of sodium carbonate (2M aqueous solution, 3.66 ml), lithium chloride (239 mg, 5.6381 mmol) and ethanolic solution (5.9 ml) of pyridine-4-boronic acid pinacol cyclic ester (866 mg, 4.2243 mmol) and the mixture was heated with stirring at 95° C. for 16 hours. The reaction solution was diluted with ethyl acetate (200 ml), washed with water and dried and the solvent was evaporated therefrom. The residue was purified by silica gel column chromatography (hexane:ethyl acetate=1:1) to give the title compound (910 mg, 2.0823 mmol, 74%).

EXAMPLE 6

Methyl 5-(3,4,5,6-tetramethoxy-2-methylbenzyl)-2-(4-methoxyphenyl)benzoate

To a solution of methyl 5-(3,4,5,6-tetramethoxy-2-methylbenzyl)-2-(trifluoromethanesulfonyl)oxybenzoate (411 mg, 0.8090 mmol) in toluene (12 ml) were added tetrakistriphenylphosphine palladium (60 mg, 0.0519 mmol), aqueous solution of sodium carbonate (2M aqueous solution, 1.35 ml), lithium chloride (89 mg, 2.0995 mmol) and ethanolic solution (2.0 ml) of 4-methoxybenzene boronic acid (369 mg, 2.4282 mmol) and the mixture was heated with stirring at 95° C. for 16 hours. The reaction solution was diluted with ethyl acetate (100 ml), washed with water and dried and the solvent was evaporated therefrom. The residue was purified by silica gel column chromatography (hexane:ethyl acetate=5:1) to give the title compound (351 mg, 0.7532 mmol, 93%).

EXAMPLE 7

Methyl 5-(3,4,5,6-tetramethoxy-2-methylbenzyl)-2-(3-methoxyphenyl)benzoate

To a solution of methyl 5-(3,4,5,6-tetramethoxy-2-methylbenzyl)-2-(trifluoromethanesulfonyl)oxybenzoate (1.50 g, 2.9527 mmol) in toluene (40 ml) were added tetrakistriphenylphosphine palladium (205 mg, 0.1774 mmol), aqueous solution of sodium carbonate (2M aqueous solution, 4.58 ml), lithium chloride (300 mg, 7.0771 mmol) and ethanolic solution (7.2 ml) of 3-methoxybenzene boronic acid (1.34 g, 8.8186 mmol) and the mixture was heated with stirring at 95° C. for 16 hours. The reaction solution was diluted with ethyl acetate (100 ml), washed with water and dried and the solvent was evaporated therefrom. The residue was purified by silica gel column chromatography (hexane:ethyl acetate=5:1) to give the title compound (1.23 g, 2.6394 mmol, 89%).

EXAMPLE 8

Methyl 5-(3,4,5,6-tetramethoxy-2-methylbenzyl)-2-(2-methoxyphenyl)benzoate

To a solution of methyl 5-(3,4,5,6-tetramethoxy-2-methylbenzyl)-2-(trifluoromethanesulfonyl)oxybenzoate (1.50 g, 2.9527 mmol) in toluene (40 ml) were added tetrakistriphenylphosphine palladium (205 mg, 0.1774 mmol), aqueous solution of sodium carbonate (2M aqueous solution, 4.58 ml), lithium chloride (300 mg, 7.0771 mmol) and ethanolic solution (7.2 ml) of 2-methoxybenzene boronic acid (1.34 g, 8.8186 mmol) and the mixture was heated with stirring at 95° C. for 16 hours. The reaction solution was diluted with ethyl acetate (100 ml), washed with water and dried and the solvent was evaporated therefrom. The residue was purified by silica gel column chromatography (hexane:ethyl acetate=5:1) to give the title compound (1.34 g, 2.8755 mmol, 97%).

EXAMPLE 9

Methyl 3-(3,4,5,6-tetramethoxy-2-methylbenzyl)-2-(3-pyridyl)benzoate

To a solution of methyl 3-(3,4,5,6-tetramethoxy-2-methylbenzyl)-2-(trifluoromethanesulfonyl)oxybenzoate (316 mg, 0.6220 mmol) in toluene (7.1 ml) were added tetrakistriphenylphosphine palladium (22 mg, 0.0190 mmol), aqueous solution of sodium carbonate (2M aqueous solution, 0.81 ml), lithium chloride (53 mg, 1.2502 mmol) and ethanolic solution (1.3 ml) of pyridine-3-boronic acid 1,3-propanediol cyclic ester (151 mg, 0.9320 mmol) and the mixture was heated with stirring at 95° C. for 16 hours. The reaction solution was diluted with ethyl acetate (100 ml), washed with water and dried and the solvent was evaporated therefrom. The residue was purified by silica gel column chromatography (hexane:ethyl acetate=1:1) to give the title compound (231 mg, 0.5286 mmol, 85%).

EXAMPLE 10

Methyl 3-(3,4,5,6-tetramethoxy-2-methylbenzyl)-2-(4-pyridyl)benzoate

To a solution of methyl 3-(3,4,5,6-tetramethoxy-2-methylbenzyl)-2-(trifluoromethanesulfonyl)oxybenzoate (385 mg, 0.7578 mmol) in toluene (8.6 ml) were added tetrakistriphenylphosphine palladium (26 mg, 0.0224 mmol), aqueous solution of sodium carbonate (2M aqueous solution, 0.99 ml), lithium chloride (64 mg, 1.5097 mmol) and ethanolic solution (1.59 ml) of pyridine-4-boronic acid pinacol cyclic ester (233 mg, 1.1365 mmol) and the mixture was heated with stirring at 95° C. for 16 hours. The reaction solution was diluted with ethyl acetate (100 ml), washed with water and dried and the solvent was evaporated therefrom. The residue was purified by silica gel column chromatography (hexane:ethyl acetate=1:1) to give the title compound (301 mg, 0.6887 mmol, 91%).

EXAMPLE 11

4-(3,4,5,6-Tetramethoxy-2-methylbenzyl)-2-phenylbenzoic acid

Methyl 4-(3,4,5,6-tetramethoxy-2-methylbenzyl)-2-phenylbenzoate (84 mg, 0.1926 mmol) was dissolved in a mixed solution of a 1N aqueous solution of sodium hydroxide (5 ml) and 1,4-dioxane (5 ml) followed by stirring at room temperature for 16 hours. The reaction solution was diluted with water (20 ml), washed with ether, acidified with concentrated hydrochloric acid and extracted with ether. The extract was washed with water and dried and the solvent was evaporated therefrom to give the title compound (45 mg, 0.1800 mmol, 93%).

EXAMPLE 12

4-(3,4,5,6-Tetramethoxy-2-methylbenzyl)-2-(3-pyridyl) benzoic acid

Methyl 4-(3,4,5,6-tetramethoxy-2-methylbenzyl)-2-(3-pyridyl)benzoate (70 mg, 0.1601 mmol) was dissolved in a mixed solution of a 1N aqueous solution of sodium hydroxide (5 ml) and 1,4-dioxane (5 ml) followed by stirring at room temperature for 16 hours. The reaction solution was diluted with water (20 ml), washed with ether, acidified with concentrated hydrochloric acid and extracted with ether. The extract was washed with water and dried and the solvent was evaporated therefrom to give the title compound (45 mg, 0.1063 mmol, 66%).

EXAMPLE 13

5-(3,4,5,6-Tetramethoxy-2-methylbenzyl)-2-phenylbenzoic acid

Methyl 5-(3,4,5,6-tetramethoxy-2-methylbenzyl)-2-phenylbenzoate (349 mg, 0.8004 mmol) was dissolved in a mixed solution of a 1N aqueous solution of sodium hydroxide (10 ml) and 1,4-dioxane (20 ml) followed by stirring at room temperature for 16 hours. The reaction solution was diluted with water (100 ml), washed with ether, acidified with concentrated hydrochloric acid and extracted with ether. The extract was washed with water and dried and the solvent was evaporated therefrom to give the title compound (340 mg, 0.7819 mmol, 98%).

EXAMPLE 14

5-(3,4,5,6-Tetramethoxy-2-methylbenzyl)-2-(3-pyridyl)benzoic acid

Methyl 5-(3,4,5,6-tetramethoxy-2-methylbenzyl)-2-(3-pyridyl)benzoate (1.20 g, 2.7459 mmol) was dissolved in a mixed solution of a 1N aqueous solution of sodium hydroxide (13.7 ml) and 1,4-dioxane (30 ml) followed by stirring at room temperature for 16 hours. The reaction solution was diluted with water (200 ml), washed with ether, acidified with concentrated hydrochloric acid and extracted with ether. The extract was washed with water and dried and the solvent was evaporated therefrom to give the title compound (1.02 g, 2.4113 mmol, 88%).

EXAMPLE 15

5-(3,4,5,6-Tetramethoxy-2-methylbenzyl)-2-(4-pyridyl)benzoic acid

Methyl 5-(3,4,5,6-tetramethoxy-2-methylbenzyl)-2-(4-pyridyl)benzoate (910 mg, 2.0823 nmol) was dissolved in a mixed solution of a 1N aqueous solution of sodium hydroxide (10.4 ml) and 1,4-dioxane (25 ml) followed by stirring at room temperature for 16 hours. The reaction solution was diluted with water (200 ml), washed with ether, acidified with concentrated hydrochloric acid and extracted with ether. The extract was washed with water and dried and the solvent was evaporated therefrom to give the title compound (655 mg, 1.5484 mmol, 74%).

EXAMPLE 16

5-(3,4,5,6-Tetramethoxy-2-methylbenzyl)-2-(4-methoxyphenyl)benzoic acid

Methyl 5-(3,4,5,6-tetramethoxy-2-methylbenzyl)-2-(4-methoxyphenyl)benzoate (472 mg, 1.0128 mmol) was dissolved in a mixed solution of a 1N aqueous solution of sodium hydroxide (10 ml) and 1,4-dioxane (20 ml) followed by stirring at room temperature for 16 hours. The reaction solution was diluted with water (100 ml), washed with ether, acidified with concentrated hydrochloric acid and extracted with ether. The extract was washed with water and dried and the solvent was evaporated therefrom to give the title compound (440 mg, 0.9734 mmol, 96%).

EXAMPLE 17

5-(3,4,5,6-Tetramethoxy-2-methylbenzyl)-2-(3-methoxyphenyl)benzoic acid

Methyl 5-(3,4,5,6-tetramethoxy-2-methylbenzyl)-2-(3-methoxyphenyl)benzoate (1.23 g, 2.6394 mmol) was dissolved in a mixed solution of a 1N aqueous solution of sodium hydroxide (20 ml) and 1,4-dioxane (40 ml) followed by stirring at room temperature for 16 hours. The reaction solution was diluted with water (200 ml), washed with ether, acidified with concentrated hydrochloric acid and extracted with ether. The extract was washed with water and dried and the solvent was evaporated therefrom to give the title compound (1.03 g, 2.2787 mmol, 85%).

EXAMPLE 18

5-(3,4,5,6-Tetramethoxy-2-methylbenzyl)-2-(2-methoxyphenyl)benzoic acid

Methyl 5-(3,4,5,6-tetramethoxy-2-methylbenzyl)-2-(2-methoxyphenyl)benzoate (1.34 g, 2.8755 mmol) was dissolved in a mixed solution of a 1N aqueous solution of sodium hydroxide (20 ml) and 1,4-dioxane (40 ml) followed by stirring at room temperature for 16 hours. The reaction solution was diluted with water (200 ml), washed with ether, acidified with concentrated hydrochloric acid and extracted with ether. The extract was washed with water and dried and the solvent was evaporated therefrom to give the title compound (1.21 g, 2.6769 mmol, 93%).

EXAMPLE 19

3-(3,4,5,6-Tetramethoxy-2-methylbenzyl)-2-(3-pyridyl)benzoic acid

Methyl 3-(3,4,5,6-tetramethoxy-2-methylbenzyl)-2-(3-pyridyl)benzoate (231 mg, 0.5286 mmol) was dissolved in a mixed solution of a 1N aqueous solution of sodium hydroxide (10 ml) and 1,4-dioxane (10 ml) followed by stirring at room temperature for 16 hours. The reaction solution was diluted with water (200 ml), washed with ether, acidified with concentrated hydrochloric acid and extracted with ether. The extract was washed with water and dried and the solvent was evaporated therefrom to give the title compound (170 mg, 0.4018 mmol, 76%).

EXAMPLE 20

3-(3,4,5,6-Tetramethoxy-2-methylbenzyl)-2-(4-pyridyl)benzoic acid

Methyl 3-(3,4,5,6-tetramethoxy-2-methylbenzyl)-2-(4-pyridyl)benzoate (301 mg, 0.5508 mmol) was dissolved in a mixed solution of a 1N aqueous solution of sodium hydroxide (10 ml) and 1,4-dioxane (10 ml) followed by stirring at room temperature for 16 hours. The reaction solution was diluted with water (100 ml), washed with ether, acidified with concentrated hydrochloric acid and extracted with ether. The extract was washed with water and dried and the solvent was evaporated therefrom to give the title compound (233 mg, 0.5508 mmol, 80%).

EXAMPLE 21

N-[4-(3,4,5,6-Tetramethoxy-2-methylbenzyl)-2-(3-pyridyl)benzoyl]piperidine 4-(3,4,5,6-Tetramethoxy-2-methylbenzyl)-2-(3-pyridyl)benzoic acid (60 mg, 0.1415 mmol), 4-dimethylaminopyridine (8.6 mg, 0.0704 mmol) and piperidine (24 mg, 0.2823 mmol) were dissolved in methylene chloride (5 ml), WSC-HCl (81 mg, 0.4225 mmol) was added thereto and the mixture was stirred at room temperature for 16 hours. The reaction solution was washed with water and dried and the solvent was evaporated therefrom. The residue was purified by preparative thin layer chromatography (methylene chloride:methanol=95:5) to give the title compound (62 mg, 0.1265 mmol, 89%).

EXAMPLE 22

N-[4-(3,4,5,6-Tetramethoxy-2-methylbenzyl)-2-(3-pyridyl)benzoyl]morpholine 4-(3,4,5,6-Tetramethoxy-2-methylbenzyl)-2-(3-pyridyl)benzoic acid (7 mg, 0.0165 mmol), 4-dimethylaminopyridine (1.0 mg, 0.0081 mmol) and morpholine (2.9 mg, 0.0333 mmol) were dissolved in methylene chloride (2 ml), WSC-HCl (9.5 mg, 0.0495 mmol) was added thereto and the mixture was stirred at room temperature for 6 hours. The reaction solution was washed with water and dried and the solvent was evaporated therefrom. The residue was purified by preparative thin layer chromatography (methylene chloride:methanol=95:5) to give the title compound (8.0 mg, 0.0162 mmol, 98%).

EXAMPLE 23

N-[4-(3,4,5,6-Tetramethoxy-2-methylbenzyl)-2-(3-pyridyl)benzoyl]-4-trifluoromethylaniline To a solution of 4-(3,4,5,6-Tetramethoxy-2-methylbenzyl)-2-(3-pyridyl)benzoic acid (82 mg, 0.1933 mmol) in methylene chloride (10 ml) were added 4-trifluoromethylaniline (47 mg, 0.2919 mmol), triethylamine (39 mg, 0.3861 mmol) and 2-chloro-1,3-dimethylimidazolinium chloride (98 mg, 0.5798 mmol) followed by stirring at room temperature for 16 hours. The reaction solution was washed with water and dried and the solvent was evaporated therefrom. The residue was purified by preparative thin layer chromatography (methylene chloride:methanol=95:5) to give the title compound (58 mg, 0.1024 mmol, 53%).

EXAMPLE 24

N-[5-(3,4,5,6-Tetramethoxy-2-methylbenzyl)-2-(3-pyridyl)benzoyl]piperidine 5-(3,4,5,6-Tetramethoxy-2-methylbenzyl)-2-(3-pyridyl)benzoic acid (80 mg, 0.1886 mmol), 4-dimethylaminopyridine (12 mg, 0.0983 mmol) and piperidine (32 mg, 0.3764 mmol) were dissolved in methylene chloride (10 ml), WSC-HCl (109 mg, 0.5685 mmol) was added thereto and the mixture was stirred at room temperature for 16 hours. The reaction solution was washed with water and dried and the solvent was evaporated therefrom. The residue was purified by preparative thin layer chromatography (methylene chloride:methanol=95:5) to give the title compound (45 mg, 0.0918 mmol, 49%).

EXAMPLE 25

N-[5-(3,4,5,6-Tetramethoxy-2-methylbenzyl)-2-(3-pyridyl)benzoyl]morpholine 5-(3,4,5,6-Tetramethoxy-2-methylbenzyl)-2-(3-pyridyl)benzoic acid (80 mg, 0.1886 mmol), 4-dimethylaminopyridine (12 mg, 0.0983 mmol) and morpholine (33 mg, 0.3793 mmol) were dissolved in methylene chloride (10 ml), WSC-HCl (109 mg, 0.5685 mmol) was added thereto and the mixture was stirred at room temperature for 16 hours. The reaction solution was washed with water and dried and the solvent was evaporated therefrom. The residue was purified by preparative thin layer chromatography (methylene chloride:methanol=95:5) to give the title compound (51 mg, 0.1036 mmol, 55%).

EXAMPLE 26

N-[5-(3,4,5,6-Tetramethoxy-2-methylbenzyl)-2-(3-pyridyl)benzoyl]-4-trifluoromethylaniline To a solution of 5-(3,4,5,6-Tetramethoxy-2-methylbenzyl)-2-(3-pyridyl)benzoic acid (85 mg, 0.2004 mmol) in methylene chloride (5 ml) were added 4-trifluoromethylaniline (48 mg, 0.2981 mmol), triethylamine (41 mg, 0.4059 mmol) and 2-chloro-1,3-dimethylimidazolinium chloride (102 mg, 0.6035 mmol) followed by stirring at room temperature for 3 hours. The reaction solution was washed with water and dried and the solvent was evaporated therefrom. The residue was purified by preparative thin layer chromatography (methylene chloride:methanol=95:5) to give the title compound (60 mg, 0.1060 mmol, 53%).

EXAMPLE 27

N-[5-(3,4,5,6-Tetramethoxy-2-methylbenzyl)-2-(4-pyridyl)benzoyl]piperidine 5-(3,4,5,6-Tetramethoxy-2-methylbenzyl)-2-(4-pyridyl)benzoic acid (430 mg, 1.0165 mmol) and piperidine (173 mg, 2.0352 mmol) were dissolved in methylene chloride (30 ml), then 4-dimethylaminopyridine (62 mg, 0.5081 mmol) and WSC-HCl (487 mg, 2.5404 mmol) were added thereto and the mixture was stirred at room temperature for 6 hours. The reaction solution was washed with water and dried and the solvent was evaporated therefrom. The residue was purified by silica gel column chromatography (5% methanol-methylene chloride) to give the title compound (334 mg, 0.6816 mmol, 67%).

EXAMPLE 28

N-[5-(3,4,5,6-Tetramethoxy-2-methylbenzyl)-2-(4-pyridyl)benzoyl]morpholine 5-(3,4,5,6-Tetramethoxy-2-methylbenzyl)-2-(4-pyridyl)benzoic acid (100 mg, 0.2364 mmol) and morpholine (44 mg, 0.5057 mmol) were dissolved in methylene chloride (20 ml), then WSC-HCl (122 mg, 0.6364 mmol) was added thereto and the mixture was stirred at room temperature for 6 hours. The reaction solution was washed with water and dried and the solvent was evaporated therefrom. The residue was purified by silica gel column chromatography (5% methanol-methylene chloride) to give the title compound (102 mg, 0.2073 mmol, 88%).

EXAMPLE 29

N-[5-(3,4,5,6-Tetramethoxy-2-methylbenzyl)-2-(4-pyridyl)benzoyl]-4-trifluoromethylaniline To a solution of 5-(3,4,5,6-Tetramethoxy-2-methylbenzyl)-2-(4-pyridyl)benzoic acid (200 mg, 0.4716 mmol) in methylene chloride (10 ml) were added 4-trifluoromethylaniline (114 mg, 0.7080 mmol), triethylamine (95 mg, 0.9405 mmol) and 2-chloro-1,3-dimethylimidazolinium chloride (239 mg, 1.4142 mmol) followed by stirring at room temperature for 16 hours. The reaction solution was washed with water and dried and the solvent was evaporated therefrom. The residue was purified by preparative thin layer chromatography (methylene chloride:methanol=95:5) to give the title compound (166 mg, 0.2932 mmol, 62%).

EXAMPLE 30

N-[3-(3,4,5,6-Tetramethoxy-2-methylbenzyl)-2-(3-pyridyl)benzoyl]piperidine 3-(3,4,5,6-Tetramethoxy-2-methylbenzyl)-2-(3-pyridyl)benzoic acid (21 mg, 0.0496 mmol) and piperidine (8.4 mg, 0.0988 mmol) were dissolved in methylene chloride (3 ml), then WSC-HCl (29 mg, 0.1512 mmol) was added thereto and the mixture was stirred at room temperature for 16 hours. The reaction solution was washed with water and dried and the solvent was evaporated therefrom. The residue was purified by preparative thin layer chromatography (methylene chloride:methanol=95:5) to give the title compound (11 mg, 0.0224 mmol, 45%).

EXAMPLE 31

(S)-N-[3-(3,4,5,6-Tetramethoxy-2-methylbenzyl)-2-(3-pyridyl)benzoyl]-1-phenylethylamine 3-(3,4,5,6-Tetramethoxy-2-methylbenzyl)-2-(3-pyridyl)benzoic acid (17 mg, 0.0401 mmol) and (S)-phenethylamine (9.7 mg, 0.0801 mmol) were dissolved in methylene chloride (5 ml), then WSC-HCl (23 mg, 0.1199 mmol) was added thereto and the mixture was stirred at room temperature for 6 hours. The reaction solution was washed with water and dried and the solvent was evaporated therefrom. The residue was purified by preparative thin layer chromatography (methylene chloride:methanol=95:5) to give the title compound (10 mg, 0.0190 mmol, 47%).

EXAMPLE 32

N-[3-(3,4,5,6-Tetramethoxy-2-methylbenzyl)-2-(4-pyridyl)benzoyl]piperidine 3-(3,4,5,6-Tetramethoxy-2-methylbenzyl)-2-(4-pyridyl)benzoic acid (21 mg, 0.0496 mmol) and piperidine (8.4 mg, 0.0988 mmol) were dissolved in methylene chloride (3 ml), then WSC-HCl (29 mg, 0.1512 mmol) was added thereto and the mixture was stirred at room temperature for 16 hours. The reaction solution was washed with water and dried and the solvent was evaporated therefrom. The residue was purified by preparative thin layer chromatography (methylene chloride:methanol=95:5) to give the title compound (8.2 mg, 0.0167 mmol, 34%).

EXAMPLE 33

(S)-N-[3-(3,4,5,6-Tetramethoxy-2-methylbenzyl)-2-(4-pyridyl)benzoyl]-1-phenylethylamine 3-(3,4,5,6-Tetramethoxy-2-methylbenzyl)-2-(4-pyridyl)benzoic acid (24 mg, 0.0567 mmol) and (S)-phenethylamine (14 mg, 0.1157 mmol) were dissolved in methylene chloride (5 ml), then WSC-HCl (33 mg, 0.1721 mmol) was added thereto and the mixture was stirred at room temperature for 16 hours. The reaction solution was washed with water and dried and the solvent was evaporated therefrom. The residue was purified by preparative thin layer chromatography (methylene chloride:methanol=95:5) to give the title compound (15.9 mg, 0.0302 mmol, 53%).

EXAMPLE 34

N-[3-(3.4,5,6-Tetramethoxy-2-methylbenzyl)-2-(4-pyridyl)benzoyl]-4-trifluoromethylaniline To a solution of 3-(3,4,5,6-Tetramethoxy-2-methylbenzyl)-2-(4-pyridyl)benzoic acid (18 mg, 0.0424 mmol) in methylene chloride (3 ml) were added 4-trifluoromethylaniline (10.2 mg, 0.0633 mmol), triethylamine (8.6 mg, 0.0851 mmol) and 2-chloro-1,3-dimethylimidazolinium chloride (21.5 mg, 0.1272 mmol) followed by stirring at room temperature for 16 hours. The reaction solution was washed with water and dried and the solvent was evaporated therefrom. The residue was purified by preparative thin layer chromatography (methylene chloride:methanol=95:5) to give the title compound (17 mg, 0.0300 mmol, 71%).

EXAMPLE 35

4-(5,6-Dimethoxy-3-methyl-1,4-benzoquinon-2-yl)methyl-2-phenylbenzoic acid 4-(3,4,5,6-Tetramethoxy-2-methylbenzyl)-2-phenylbenzoic acid (76 mg, 1.1800 mmol) was dissolved in a mixed solvent of acetonitrile (3 ml) and water (1 ml), then CAN (247 mg, 0.4507 mmol) was added thereto at room temperature and the mixture was stirred for 1 hour. The reaction solution was poured into water and extracted with ethyl acetate. The extract was washed with water and dried and the solvent was evaporated therefrom. The residue was purified by silica gel column chromatography (5% methanol-methylene chloride) to give the title compound (54 mg, 0.1377 mmol, 77%).

EXAMPLE 36

4-(5,6-Dimethoxy-3-methyl-1,4-benzoquinon-2-yl) methyl-2-(3-pyridyl)benzoic acid 4-(3,4,5,6-Tetramethoxy-2-methylbenzyl)-2-(3-pyridyl) benzoic acid (30 mg, 1.1820 mmol) was dissolved in a mixed solvent of acetonitrile (6 ml) and water (2 ml), then CAN (97 mg, 0.1770 mmol) was added thereto at room temperature and the mixture was stirred for 3 hour. The reaction solution was poured into water, neutralized with a saturated aqueous solution of sodium hydrogen carbonate and extracted with ethyl acetate. The extract was washed with water and dried and the solvent was evaporated therefrom. The residue was purified by silica gel column chromatography (10% methanol-methylene chloride) to give the title compound (10 mg, 0.0254 mmol, 36%).

EXAMPLE 37

5-(5,6-Dimethoxy-3-methyl-1,4-benzoquinon-2-yl) methyl-2-phenylbenzoic acid 5-(3,4,5,6-Tetramethoxy-2-methylbenzyl)-2-phenylbenzoic acid (340 mg, 0.7819 mmol) was dissolved in a mixed solvent of acetonitrile (30 ml) and water (10 ml), then CAN (1.10 g, 2.0072 mmol) was added thereto at room temperature and the mixture was stirred for 3 hour. The reaction solution was poured into water and extracted with ether. The extract was washed with water and dried and the solvent was evaporated therefrom. The residue was purified by silica gel column chromatography (5% methanol-methylene chloride) to give the title compound (234 mg, 0.5969 mmol, 76%).

EXAMPLE 38

5-(5,6-Dimethoxy-3-methyl-1,4-benzoquinon-2-yl) methyl-2-(3-pyridyl)benzoic acid 5-(3,4,5,6-Tetramethoxy-2-methylbenzyl)-2-(3-pyridyl) benzoic acid (500 mg, 1.1820 mmol) was dissolved in a mixed solvent of acetonitrile (30 ml) and water (10 ml), then CAN (1.62 g, 2.9562 mmol) was added thereto at room temperature and the mixture was stirred for 3 hour. The reaction solution was poured into water, neutralized with a 1N aqueous solution of sodium hydroxide and extracted with ethyl acetate. The extract was washed with water and dried and the solvent was evaporated therefrom. The residue was purified by silica gel column chromatography (10% methanol-methylene chloride) to give the title compound (270 mg, 0.6870 mmol, 58%).

EXAMPLE 39

5-(5,6-Dimethoxy-3-methyl-1,4-benzoquinon-2-yl) methyl-2-(4-pyridyl)benzoic acid To a solution of 5-(3,4,5,6-tetramethoxy-2-methylbenzyl)-2-(4-pyridyl) benzoic acid (500 mg, 1.1820 mmol) in tetrahydrofuran (THF) (20 ml) was added 2-tert-butyl-1,3-diisopropylurea (2.36 g, 11.8 mmol) followed by stirring at room temperature for 16 hours. The reaction solution was concentrated and the residue was purified by silica gel column chromatography (hexane:ethyl acetate=2:1) to give tert-butyl 5-(3,4,5,6-tetramethoxy-2-methylbenzyl)-2-(4-pyridyl) benzoate (400 mg, 0.8350 mmol, 70%). The compound was dissolved in a mixed solvent of acetonitrile (30 ml) and water (10 ml), then CAN (1.12 g, 2.0437 mmol) was added thereto and the mixture was stirred for 3 hours.

The reaction solution was poured into water, neutralized with a 1N aqueous solution of sodium hydroxide and extracted with ethyl acetate. The extract was washed with water and dried and the solvent was evaporated therefrom. The residue was purified by silica gel column chromatography (methylene chloride:methanol=95:5) to give tert-butyl 5-(5,6-dimethoxy-3-methyl-1,4-benzoquinon-2-yl)-2-(4-pyridyl)benzoate (251 mg, 0.5590 mmol, 67%). The compound (251 mg, 0.5590 mmol) was dissolved in formic acid (10 ml) and stirred at room temperature for 6 hours. The residue obtained by evaporation of the solvent was washed with ether to give the title compound (202 mg, 0.5139 mmol, 92%). (The overall yield: 43%)

EXAMPLE 40

5-(5,6-Dimethoxy-3-methyl-1,4-benzoquinon-2-yl) methyl-2-(4-methoxyphenyl)benzoic acid 5-(3,4,5,6-Tetramethoxy-2-methylbenzyl)-2-(4-methoxyphenyl)benzoic acid (440 mg, 0.9734 mmol) was dissolved in a mixed solvent of acetonitrile (30 ml) and water (10 ml), then CAN (1.10 g, 2.0072 mmol) was added thereto at room temperature and the mixture was stirred for 3 hour. The reaction solution was poured into water and extracted with ether. The extract was washed with water and dried and the solvent was evaporated therefrom. The residue was purified by silica gel column chromatography (5% methanol-methylene chloride) to give the title compound (259 mg, 0.6137 mmol, 63%).

EXAMPLE 41

5-(5,6-Dimethoxy-3-methyl-1,4-benzoquinon-2-yl) methyl-2-(3-methoxyphenyl)benzoic acid 5-(3,4,5,6-Tetramethoxy-2-methylbenzyl)-2-(3-methoxyphenyl)benzoic acid (1.03 g, 2.2787 mmol) was dissolved in a mixed solvent of acetonitrile (30 ml) and water (10 ml), then CAN (3.12 g, 5.6934 mmol) was added thereto at room temperature and the mixture was stirred for 3 hour. The reaction solution was poured into water and extracted with ether. The extract was washed with water and dried and the solvent was evaporated therefrom. The residue was purified by silica gel column chromatography (5% methanol-methylene chloride) to give the title compound (817 mg, 1.9360 mmol, 85%).

EXAMPLE 42

5-(5,6-Dimethoxy-3-methyl-1,4-benzoquinon-2-yl) methyl-2-(2-methoxyphenyl)benzoic acid 5-(3,4,5,6-Tetramethoxy-2-methylbenzyl)-2-(2-methoxyphenyl)benzoic acid (1.21 g, 2.6769 mmol) was dissolved in a mixed solvent of acetonitrile (30 ml) and water (10 ml), then CAN (3.60 g, 6.6914 mmol) was added thereto at room temperature and the mixture was stirred for 3 hour. The reaction solution was poured into water and extracted with ether. The extract was washed with water and dried and the solvent was evaporated therefrom. The residue was purified by silica gel column chromatography (5% methanol-methylene chloride) to give the title compound (859 mg, 2.0355 mmol, 76%).

EXAMPLE 43

N-[4-(5,6-Dimethoxy-3-methyl-1,4-benzoquinon-2-yl)methyl-2-phenylbenzoyl]piperidine 4-(5,6-Dimethoxy-3-methyl-1,4-benzoquinon-2-yl)methyl-2-phenylbenzoic acid (18 mg, 0.0459 mmol) and piperidine (5.9 mg, 0.0692 mmol) were dissolved in methylene chloride (3 ml), then WSC-HCl (22 mg, 0.1147 mmol) was added thereto and the mixture was stirred at room temperature for 6 hours. The reaction solution was washed with water and dried and the solvent was evaporated therefrom. The residue was purified by preparative thin layer chromatography (hexane:ethyl acetate=1:1) to give the title compound (12 mg, 0.0261 mmol, 57%).

EXAMPLE 44

N-[4-(5,6-Dimethoxy-3-methyl-1,4-benzoquinon-2-yl)methyl-2-phenylbenzoyl]morpholine 4-(5,6-Dimethoxy-3-methyl-1,4-benzoquinon-2-yl)methyl-2-phenylbenzoic acid (18 mg, 0.0459 mmol) and morpholine (6 mg, 0.0689 mmol) were dissolved in methylene chloride (3 ml), then WSC-HCl (22 mg, 0.1147 mmol) was added thereto and the mixture was stirred at room temperature for 6 hours. The reaction solution was washed with water and dried and the solvent was evaporated therefrom. The residue was purified by preparative thin layer chromatography (hexane:ethyl acetate=1:1) to give the title compound (10 mg, 0.0216 mmol, 47%).

EXAMPLE 45

N-[4-(5,6-Dimethoxy-3-methyl-1,4-benzoquinon-2-yl)methyl-2-phenylbenzoyl]-4-trifluoromethyl-aniline 4-(5,6-Dimethoxy-3-methyl-1,4-benzoquinon-2-yl)methyl-2-phenylbenzoic acid (16 mg, 0.0408 mmol) was dissolved in methylene chloride (3 ml), then 4-trifluoromethylaniline (13 mg, 0.0807 mmol), triethylamine (8.2 mg, 0.0811 mmol) and 2-chloro-1,3-dimethylimidazolinium chloride (21 mg, 0.1242 mmol) were added thereto and the mixture was stirred for 16 hours. The reaction solution was poured into water and extracted with ethyl acetate. The extract was washed with water and the solvent was evaporated therefrom. The residue was purified by preparative thin layer chromatography (hexane:ethyl acetate=1:1) to give the title compound (8 mg, 0.0149 mmol, 37%).

EXAMPLE 46

N-[4-(5,6-Dimethoxy-3-methyl-1,4-benzoquinon-2-yl)methyl-2-(3-pyridyl)benzoyl]piperidine N-[4-(3,4,5,6-Tetramethoxy-2-methylbenzyl)-2-(3-pyridyl)benzoyl]piperidine (70 mg, 0.1428 mmol) was dissolved in a mixed solvent of acetonitrile (6 ml) and water (2 ml), then CAN (231 mg, 0.4293 mmol) was added thereto at room temperature and the mixture was stirred for 3 hours. The reaction solution was poured into water and extracted with ethyl acetate. The extract was washed with water and dried and the solvent was evaporated therefrom. The residue was purified by preparative thin layer chromatography (methylene chloride:methanol=95:5) to give the title compound (26 mg, 0.0565 mmol, 40%).

EXAMPLE 47

N-[4-(5,6-Dimethoxy-3-methyl-1,4-benzoquinon-2-yl)methyl-2-(3-pyridyl)benzoyl]morpholine N-[4-(3,4,5,6-Tetramethoxy-2-methylbenzyl)-2-(3-pyridyl)benzoyl]morpholine (8 mg, 0.0162 mmol) was dissolved in a mixed solvent of acetonitrile (3 ml) and water (1 ml), then CAN (26 mg, 0.0483 mmol) was added thereto at room temperature and the mixture was stirred for 3 hours. The reaction solution was poured into water and extracted with ethyl acetate. The extract was washed with water and dried and the solvent was evaporated therefrom. The residue was purified by preparative thin layer chromatography (methylene chloride:methanol=95:5) to give the title compound (4.5 mg, 0.0097 mmol, 60%).

EXAMPLE 48

N-[4-(5,6-Dimethoxy-3-methyl-1,4-benzoquinon-2-yl)methyl-2-(3-pyridyl)benzoyl]-4-trifluoromethylaniline N-[4-(3,4,5,6-Tetramethoxy-2-methylbenzyl)-2-(3-pyridyl)benzoyl]-4-trifluoromethylaniline (55 mg, 0.0971 mmol) was dissolved in a mixed solvent of acetonitrile (3 ml) and water (1 ml), then CAN (157 mg, 0.2918 mmol) was added thereto at room temperature and the mixture was stirred for 2 hours. The reaction solution was poured into water and extracted with ethyl acetate. The extract was washed with water and dried and the solvent was evaporated therefrom. The residue was purified by preparative thin layer chromatography (methylene chloride:methanol=95:5) to give the title compound (10 mg, 0.0186 mmol, 19%).

EXAMPLE 49

N-[4-(5,6-Dimethoxy-3-methyl-1,4-benzoquinon-2-yl)methyl-2-(3-pyridyl)benzoyl]-4-methoxy-aniline 4-(5,6-Dimethoxy-3-methyl-1,4-benzoquinon-2-yl)methyl-2-(3-pyridyl)benzoic acid (44 mg, 0.1119 mmol) was dissolved in methylene chloride (10 ml), then p-anisidine (28 mg, 0.2276 mmol), triethylamine (23 mg, 0.2277 mmol) and 2-chloro-1,3-dimethylimidazolinium chloride (38 mg, 0.1982 mmol) were added thereto at room temperature and the mixture was stirred for 16 hours. The reaction solution was poured into water and extracted with ethyl acetate. The extract was washed with water and dried and the solvent was evaporated therefrom. The residue was purified by preparative thin layer chromatography (methylene chloride:methanol=95:5) to give the title compound (33 mg, 0.0662 mmol, 59%).

EXAMPLE 50

N-[5-(5,6-Dimethoxy-3-methyl-1,4-benzoquinon-2-yl)methyl-2-phenylbenzoyl]piperidine 5-(5,6-Dimethoxy-3-methyl-1,4-benzoquinon-2-yl)methyl-2-phenylbenzoic acid (40 mg, 0.1020 mmol), 4-dimethylaminopyridine (6.2 mg, 0.0508 mmol) and piperidine (17 mg, 0.2000 mmol) were dissolved in methylene chloride (5 ml), then WSC-HCl (59 mg, 0.3077 mmol) was added thereto and the mixture was stirred at room temperature for 16 hours. The reaction solution was washed with water and dried and the solvent was evaporated therefrom. The residue was purified by preparative thin layer chromatography (hexane:ethyl acetate=2:1) to give the title compound (16 mg, 0.0348 mmol, 34%).

EXAMPLE 51

N-[5-(5,6-Dimethoxy-3-methyl-1,4-benzoquinon-2-yl)methyl-2-phenylbenzoyl]morpholine 5-(5,6-Dimethoxy-3-methyl-1,4-benzoquinon-2-yl)methyl-2-phenylbenzoic acid (40 mg, 0.1020 mmol), 4-dimethylaminopyridine (6.2 mg, 0.0508 mmol) and morpholine (18 mg, 0.2068 mmol) were dissolved in methylene chloride (5 ml), then WSC-HCl (59 mg, 0.3077 mmol) was added thereto and the mixture was stirred at room temperature for 16 hours. The reaction solution was washed with water and dried and the solvent was evaporated therefrom. The residue was purified by preparative thin layer chromatography (hexane:ethyl acetate=1:1) to give the title compound (13 mg, 0.0281 mmol, 28%).

EXAMPLE 52

N-[5-(5,6-Dimethoxy-3-methyl-1,4-benzoquinon-2-yl)methyl-2-phenylbenzoyl]-4-methoxyaniline 5-(5,6-Dimethoxy-3-methyl-1,4-benzoquinon-2-yl)methyl-2-phenylbenzoic acid (33 mg, 0.0841 mmol) was dissolved in methylene chloride (3 ml), then p-anisidine (21 mg, 0.1707 mmol), triethylamine (34 mg, 0.3366 mmol) and 2-chloro-1,3-dimethylimidazolinium chloride (57 mg, 0.3372 mmol) were added thereto and the mixture was stirred at room temperature for 16 hours. The reaction solution was poured into water and extracted with ethyl acetate. The extract was washed with water and dried and the solvent was evaporated therefrom. The residue was purified by preparative thin layer silica gel (hexane:ethyl acetate=1:1) to give the title compound (28 mg, 0.0563 mmol, 67%).

EXAMPLE 53

N-[5-(5,6-Dimethoxy-3-methyl-1,4-benzoquinon-2-yl)methyl-2-phenylbenzoyl]-4-trifluoromethylaniline 5-(5,6-Dimethoxy-3-methyl-1,4-benzoquinon-2-yl)methyl-2-phenylbenzoic acid (40 mg, 0.1020 mmol) was dissolved in methylene chloride (5 ml), then 4-trifluoromethylaniline (25 mg, 0.1552 mmol), triethylamine (21 mg, 0.2079 mmol) and 2-chloro-1,3-dimethylimidazolinium chloride (52 mg, 0.3076 mmol) were added thereto and the mixture was stirred for 16 hours. The reaction solution was poured into water and extracted with ethyl acetate. The extract was washed with water and dried and the solvent was evaporated therefrom. The residue was purified by preparative thin layer chromatography (hexane:ethyl acetate=3:1) to give the title compound (5 mg, 0.0093 mmol, 9%).

EXAMPLE 54

N-[5-(5,6-Dimethoxy-3-methyl-1,4-benzoquinon-2-yl)methyl-2-(3-pyridyl)benzoyl]piperidine N-[5-(3,4,5,6-Tetramethoxy-2-methylbenzyl)-2-(3-pyridyl)benzoyl]piperidine (33 mg, 0.0673 mmol) was dissolved in a mixed solvent of acetonitrile (6 ml) and water (2 ml), then CAN (92 mg, 0.1678 mmol) was added thereto at room temperature and the mixture was stirred for 1 hour. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (methylene chloride:methanol=95:5) to give the title compound (20 mg, 0.0434 mmol, 64%).

EXAMPLE 55

N-[5-(5,6-Dimethoxy-3-methyl-1,4-benzoquinon-2-yl)methyl-2-(3-pyridyl)benzoyl]morpholine 5-(5,6-Dimethoxy-3-methyl-1,4-benzoquinon-2-yl)methyl-2-(3-pyridyl)benzoic acid (40 mg, 0.1017 mmol) and morpholine (18 mg, 0.2608 mmol) were dissolved in methylene chloride (3 ml), then WSC-HCl (49 mg, 0.2556 mmol) was added thereto and the mixture was stirred at room temperature for 6 hours. The reaction solution was washed with water and dried and the solvent was evaporated therefrom. The residue was purified by silica gel column chromatography (methylene chloride:methanol=95:5) to give the title compound (32 mg, 0.0692 mmol, 68%).

EXAMPLE 56

N-[5-(5,6-Dimethoxy-3-methyl-1,4-benzoquinon-2-yl)methyl-2-(3-pyridyl)benzoyl]-4-methoxy-aniline 5-(5,6-Dimethoxy-3-methyl-1,4-benzoquinon-2-yl)methyl-2-(3-pyridyl) benzoic acid (73 mg, 0.1857 mmol) was dissolved in methylene chloride (5 ml), then p-anisidine (46 mg, 0.3739 mmol), triethylamine (75 mg, 0.7425 mmol) and 2-chloro-1,3-dimethylimidazolinium chloride (126 mg, 0.7455 mmol) were added thereto at room temperature and the mixture was stirred at room temperature for 16 hours. The reaction solution was poured into water and extracted with ethyl acetate. The extract was washed with water and dried and the solvent was evaporated therefrom. The residue was purified by preparative thin layer silica gel (hexane:ethyl acetate=1:4) to give the title compound (33 mg, 0.0662 mmol, 36%).

EXAMPLE 57

N-[5-(5,6-Dimethoxy-3-methyl-1,4-benzoquinon-2-yl)methyl-2-(3-pyridyl)benzoyl]-4-trifluoromethylaniline N-[5-(3,4,5,6-Tetramethoxy-2-methylbenzyl)-2-(3-pyridyl)benzoyl]-4-trifluoromethylaniline (60 mg, 0.1060 mmol) was dissolved in a mixed solvent of acetonitrile (9 ml) and water (3 ml), then CAN (228 mg, 0.4237 mmol) was added thereto at room temperature and the mixture was stirred for 3 hours. The reaction solution was poured into water and extracted with ethyl acetate. The extract was washed with water and dried and the solvent was evaporated therefrom. The residue was purified by preparative thin layer chromatography (methylene chloride:methanol=95:5) to give the title compound (18 mg, 0.0335 mmol, 32%).

EXAMPLE 58

N-[5-(5,6-Dimethoxy-3-methyl-1,4-benzoquinon-2-yl)methyl-2-(4-pyridyl)benzoyl]piperidine (methanesulfonate)

N-[5-(3,4,5,6-Tetramethoxy-2-methylbenzyl)-2-(4-pyridyl)benzoyl]piperidine (630 mg, 1.2857 mmol) was dis solved in a mixed solvent of acetonitrile (30 ml) and water (10 ml), then CAN (1.73 g, 3.1569 mmol) was added thereto at room temperature and the mixture was stirred for 1 hour. The reaction solution was poured into water, neutralized with a saturated aqueous solution of sodium hydrogen carbonate and extracted with ethyl acetate. The extract was washed with water and dried and the solvent was evaporated therefrom. The residue was purified by silica gel column chromatography (methylene chloride:methanol=95:5) to give the title compound (470 mg, 0.1217 mmol, 79%). The compound (470 mg, 0.1217 mmol) was dissolved in anhydrous methylene chloride, treated with 1 equivalent of methanesulfonic acid and concentrated. The residue was recrystallized from a mixed solvent of ethyl acetate, toluene and ether to give a methanesulfonate of the title compound (450 mg).

EXAMPLE 59

N-[5-(5,6-Dimethoxy-3-methyl-1,4-benzoquinon-2-yl)methyl-2-(4-pyridyl)benzoyl]morpholine N-[5-(3,4,5,6-Tetramethoxy-2-methylbenzyl)-2-(4-pyridyl)benzoyl]morpholine (102 mg, 0.2037 mmol) was dissolved in a mixed solvent of acetonitrile (15 ml) and water (5 ml), then CAN (279 mg, 0.5091 mmol) was added thereto at room temperature and the mixture was stirred for 3 hours. The reaction solution was poured into water, neutralized with 1N aqueous solution of sodium hydroxide and extracted with ethyl acetate. The extract was washed with water and dried and the solvent was evaporated therefrom. The residue was purified by silica gel column chromatography (methylene chloride:methanol=95:5) to give the title compound (60 mg, 0.1298 mmol, 63%).

EXAMPLE 60

N-[5-(5,6-Dimethoxy-3-methyl-1,4-benzoquinon-2-yl)methyl-2-(4-pyridyl)benzoyl]-4-methoxyaniline 5-(5,6-Dimethoxy-3-methyl-1,4-benzoquinon-2-yl)methyl-2-(4-pyridyl) benzoic acid (100 mg, 0.2544 mmol) was dissolved in methylene chloride (30 ml), then p-anisidine (56 mg, 0.4552 mmol), triethylamine (75 mg, 0.7425 mmol) and 2-chloro-1,3-dimethylimidazolinium chloride (126 mg, 1.3663 mmol) were added thereto at room temperature and the mixture was stirred at room temperature for 16 hours. The reaction solution was poured into water and extracted with ethyl acetate. The extract was washed with water and dried and the solvent was evaporated therefrom. The residue was purified by preparative thin layer silica gel (hexane:ethyl acetate=1:4) to give the title compound (33 mg, 0.0963 mmol, 38%).

EXAMPLE 61

N-[5-(5,6-Dimethoxy-3-methyl-1,4-benzoquinon-2-yl)methyl-2-(4-pyridyl)benzoyl]-4-trifluoromethylaniline N-[5-(3,4,5,6-Tetramethoxy-2-methylbenzyl)-2-(4-pyridyl)benzoyl]-4-trifluoromethylaniline (140 mg, 0.2473 mmol) was dissolved in a mixed solvent of acetonitrile (9 ml) and water (3 ml), then CAN (399 mg, 0.7416 mmol) was added thereto at room temperature and the mixture was stirred for 3 hours. The reaction solution was poured into water and extracted with ethyl acetate. The extract was washed with water and dried and the solvent was evaporated therefrom. The residue was purified by preparative thin layer chromatography (methylene chloride:methanol=95:5) to give the title compound (60 mg, 0.1119 mmol, 45%).

EXAMPLE 62

N-[5-(5,6-Dimethoxy-3-methyl-1,4-benzoquinon-2-yl)methyl-2-(4-methoxyphenyl)benzol]-piperidine 5-(5,6-Dimethoxy-3-methyl-1,4-benzoquinon-2-yl)methyl-2-(4-methoxyphenyl)benzoic acid (50 mg, 0.1184 mmol) and piperidine (20 mg, 0.2351 mmol) were dissolved in methylene chloride (30 ml), then WSC-HCl (68 mg, 0.3547 mmol) was added thereto at room temperature and the mixture was stirred for 16 hour. The reaction solution was washed with water and dried and the solvent was evaporated therefrom. The residue was purified by preparative thin layer chromatography (hexane:ethyl acetate=1:1) to give the title compound (23 mg, 0.0468 mmol, 40%).

EXAMPLE 63

N-[5-(5,6-Dimethoxy-3-methyl-1,4-benzoquinon-2-yl)methyl-2-(4-methoxyphenyl)benzoyl]-morpholine 5-(5,6-Dimethoxy-3-methyl-1,4-benzoquinon-2-yl)methyl-2-(4-methoxyphenyl)benzoic acid (50 mg, 0.1184 mmol) and morpholine (21 mg, 0.2413 mmol) were dissolved in methylene chloride (30 ml), then WSC-HCl (68 mg, 0.3547 mmol) was added thereto and the mixture was stirred for 16 hours at room temperature. The reaction solution was washed with water and dried and the solvent was evaporated therefrom. The residue was purified by preparative thin layer chromatography (hexane:ethyl acetate=1:1) to give the title compound (30 mg, 0.0613 mmol, 52%).

EXAMPLE 64

N-[5-(5,6-Dimethoxy-3-methyl-1,4-benzoquinon-2-yl)methyl-2-(4-methoxyphenyl]benzoyl)-4-methoxyaniline 5-(5,6-Dimethoxy-3-methyl-1,4-benzoquinon-2-yl)methyl-2-(4-methoxyphenyl) benzoic acid (100 mg, 0.2369 mmol) was dissolved in methylene chloride (20 ml), then p-anisidine (58 mg, 0.4715 mmol), triethylamine (48 mg, 0.4752 mmol) and 2-chloro-1,3-dimethylimidazolinium chloride (80 mg, 0.4733 mmol) were added thereto at room temperature and the mixture was stirred at room temperature for 16 hours. The reaction solution was poured into water and extracted with ethyl acetate. The extract was washed with water and dried and the solvent was evaporated therefrom. The residue was purified by preparative thin layer silica gel (hexane:ethyl acetate=1:1) to give the title compound (78 mg, 0.1480 mmol, 62%).

EXAMPLE 65

N-[5-(5,6-Dimethoxy-3-methyl-1,4-benzoquinon-2-yl)methyl-2-(3-methoxyphenyl)benzoyl]-piperidine 5-(5,6-Dimethoxy-3-methyl-1,4-benzoquinon-2-yl)methyl-2-(3-methoxyphenyl)benzoic acid (100 mg, 0.2369 mmol) and piperidine (40 mg, 0.4705 mmol) were dissolved in methylene chloride (20 ml), then 4-dimethylaminopyridine (6 mg, 0.0491 mmol) and WSC-HCl (136 mg, 0.7094 mmol) were added thereto and the mixture was stirred for 6 hours at room temperature. The reaction solution was washed with water and dried and the solvent was evaporated therefrom. The residue was purified by silica gel column chromatography (hexane:ethyl acetate=1:1) to give the title compound (58 mg, 0.1186 mmol, 50%).

EXAMPLE 66

N-[5-(5,6-Dimethoxy-3-methyl-1,4-benzoquinon-2-yl)methyl-2-(3-methoxyphenyl)benzoyl]-morpholine 5-(5,6-Dimethoxy-3-methyl-1,4-benzoquinon-2-yl)methyl-2-(3-methoxyphenyl)benzoic acid (100 mg, 0.2369 mmol) and morpholine (41 mg, 0.4712 mmol) were dissolved in methylene chloride (20 ml), then 4-dimethylaminopyridine (6 mg, 0.0491 mmol) and WSC-HCl (136 mg, 0.7094 mmol) were added thereto and the mixture was stirred for 6 hours at room temperature. The reaction solution was washed with water and dried and the solvent was evaporated therefrom. The residue was purified by silica gel column chromatography (hexane:ethyl acetate=1:3) to give the title compound (80 mg, 0.1629 mmol, 69%).

EXAMPLE 67

N-[5-(5,6-Dimethoxy-3-methyl-1,4-benzoquinon-2-yl)methyl-2-(3-methoxyphenyl)benzoyl]-4-methoxyaniline 5-(5,6-Dimethoxy-3-methyl-1,4-benzoquinon-2-yl)methyl-2-(3-methoxyphenyl) benzoic acid (100 mg, 0.2369 mmol) was dissolved in methylene chloride (20 ml), then p-anisidine (58 mg, 0.4715 mmol), triethylamine (48 mg, 0.4752 mmol) and 2-chloro-1,3-dimethylimidazolinium chloride (80 mg, 0.4733 mmol) were added thereto at room temperature and the mixture was stirred at room temperature for 16 hours. The reaction solution was poured into water and extracted with ethyl acetate. The extract was washed with water and dried and the solvent was evaporated therefrom. The residue was purified by preparative thin layer silica gel (hexane:ethyl acetate=1:1) to give the title compound (68 mg, 0.1290 mmol, 54%).

EXAMPLE 68

N-[5-(5,6-Dimethoxy-3-methyl-1,4-benzoquinon-2-yl)methyl-2-(2-methoxyphenyl)benzoyl]-4-methoxyaniline 5-(5,6-Dimethoxy-3-methyl-1,4-benzoquinon-2-yl)methyl-2-(2-methoxyphenyl) benzoic acid (66 mg, 0.1563 mmol) was dissolved in methylene chloride (5 ml), then p-anisidine (38 mg, 0.3089 mmol), triethylamine (47 mg, 0.4653 mmol) and 2-chloro-1,3-dimethylimidazolinium chloride (53 mg, 0.3136 mmol) were added thereto at room temperature and the mixture was stirred at room temperature for 16 hours. The reaction solution was poured into water and extracted with ethyl acetate. The extract was washed with water and dried and the solvent was evaporated therefrom. The residue was purified by preparative thin layer silica gel (hexane:ethyl acetate=1:1) to give the title compound (38 mg, 0.0721 mmol, 46%).

EXAMPLE 69

N-[3-(5,6-Dimethoxy-3-methyl-1,4-benzoquinon-2-yl)methyl-2-(3-pyridyl)benzoyl]piperidine N-[3-(3,4,5,6-Tetramethoxy-2-methylbenzyl)-2-(3-pyridyl)benzoyl]piperidine (80 mg, 0.1632 mmol) was dissolved in a mixed solvent of acetonitrile (9 ml) and water (3 ml), then CAN (128 mg, 0.2335 mmol) was added thereto at room temperature and the mixture was stirred for 1 hour. The reaction solution poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (hexane:ethyl acetate=1:3) to give the title compound (51 mg, 0.1108 mmol, 68%). This compound was converted to a methanesulfonate by the method according to Example 58.

EXAMPLE 70

(S)-N-[3-(5,6-Dimethoxy-3-methyl-1,4-benzoquinon-2-yl)methyl-2-(3-pyridyl)benzoyl]-1-phenylethylamine (S)-N-[3-(3,4,5,6-Tetramethoxy-2-methylbenzyl)-2-(3-pyridyl)benzoyl]-1-phenylethylamine (69 mg, 0.1311 mmol) was dissolved in a mixed solvent of acetonitrile (9 ml) and water (3 ml), then CAN (180 mg, 0.3284 mmol) was added thereto at room temperature and the mixture was stirred for 3 hours. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (hexane:ethyl acetate=1:3) to give the title compound (48 mg, 0.0967 mmol, 74%).

EXAMPLE 71

N-[3-(5.6-Dimethoxy-3-methyl-1,4-benzoquinon-2-yl)methyl-2-(4-pyridyl)benzoyl]piperidine N-[3-(3,4,5,6-Tetramethoxy-2-methylbenzyl)-2-(4-pyridyl)benzoyl]piperidine (74 mg, 0.1510 mmol) was dissolved in a mixed solvent of acetonitrile (9 ml) and water (3 ml), then CAN (206 mg, 0.3759 mmol) was added thereto at room temperature and the mixture was stirred for 1 hour. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (hexane:ethyl acetate=1:5) to give the title compound (32 mg, 0.0695 mmol, 46%).

EXAMPLE 72

(S)-N-[3-(5,6-Dimethoxy-3-methyl-1,4-benzoquinon-2-yl)methyl-2-(4-pyridyl)benzoyl]-1-phenylethylamine (S)-N-[3-(3,4,5,6-Tetramethoxy-2-methylbenzyl)-2-(4-pyridyl)benzoyl]-1-phenylethylamine (64 mg, 0.1216 mmol) was dissolved in a mixed solvent of acetonitrile (9 ml) and water (3 ml), then CAN (166 mg, 0.3029 mmol) was added thereto at room temperature and the mixture was stirred for 3 hours. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (hexane:ethyl acetate=1:3) to give the title compound (30 mg, 0.0604 mmol, 50%).

EXAMPLE 73

N-[3-(45,6-Dimethoxy-3-methyl-1,4-benzoquinon-2-yl)methyl-2-(4-pyridyl)benzoyl]-4-trifluoromethylaniline N-[3-(3,4,5,6-Tetramethoxy-2-methylbenzyl)-2-(4-pyridyl)benzoyl]-4-trifluoromethylaniline (17 mg, 0.0300 mmol) was dissolved in a mixed solvent of acetonitrile (6 ml) and water (2 ml), then CAN (48 mg, 0.0892 mmol) was added thereto at room temperature and the mixture was stirred for 3 hours. The reaction solution was poured into water and extracted with ethyl acetate. The extract was washed with water and dried and the solvent was evaporated therefrom. The residue was purified by preparative thin layer chromatography (methylene chloride:methanol=95:5) to give the title compound (6 mg, 0.0111 mmol, 37%).

EXAMPLE 74

(S)-N-[5-(5,6-Dimethoxy-3-methyl-1,4-benzoquinon-2-yl)methyl-2-(4-pyridyl)benzoyl]-1-phenylethylamine (methanesulfonate)

5-(3,4,5,6-Tetramethoxy-2-methylbenzyl)-2-(4-pyridyl)benzoic acid (100 mg, 0.2364 mmol) and (S)-1-phenylethylamine (93 mg, 0.7674 mmol) were dissolved in methylene chloride (10 ml), then 4-dimethylaminopyridine (6 mg, 0.0491 mmol) and WSC-HCl (146 mg, 0.7616 mmol) were added thereto and the mixture was stirred for 6 hours at room temperature. The reaction solution was washed with water and dried and the solvent was evaporated.

The residue was purified by silica gel column chromatography (methylene chloride:methanol=95:5) to give (S)-N-[5-(3,4,5,6-tetramethoxy-2-methylbenzyl)-2-(4-pyridyl)benzoyl]-1-phenylethylamine (90 mg, 0.1711 mmol, 72%). The compound (102 mg, 0.2073 mmol) was dissolved in a mixed solvent of acetonitrile (15 ml) and water (5 ml), then CAN (279 mg, 0.5091 mmol) was added thereto at room temperature and the mixture was stirred for 3 hours. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (hexane:ethyl acetate=1:5) to give the title compound (55 mg, 0.1298 mmol, 63%). The compound was converted to a methanesulfonate by a method according to Example 58.

EXAMPLE 75

(R)-N-[5-(5,6-Dimethoxy-3-methyl-1,4-benzoquinon-2-yl)methyl-2-(4-pyridyl)benzoyl]-1-phenylethylamine (methanesulfonate)

5-(3,4,5,6-Tetramethoxy-2-methylbenzyl)-2-(4-pyridyl)benzoic acid (100 mg, 0.2364 mmol) and (R)-1-phenylethylamine (93 mg, 0.7674 mmol) were dissolved in methylene chloride (10 ml), then 4-dimethylaminopyridine (6 mg, 0.0491 mmol) and WSC-HCl (146 mg, 0.7616 mmol) were added thereto and the mixture was stirred for 6 hours at room temperature. The reaction solution was washed with water and dried and the solvent was evaporated.

The residue was purified by silica gel column chromatography (methylene chloride:methanol=95:5) to give (R)-N-[5-(3,4,5,6-tetramethoxy-2-methylbenzyl)-2-(4-pyridyl)benzoyl]-1-phenylethylamine (98 mg, 0.1863 mmol, 79%). The compound (98 mg, 0.1863 mmol) was dissolved in a mixed solvent of acetonitrile (15 ml) and water (5 ml), then CAN (251 mg, 0.4580 mmol) was added thereto at room temperature and the mixture was stirred for 3 hours. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (hexane:ethyl acetate=1:5) to give the title compound (60 mg, 0.1209 mmol, 65%). The compound was converted to a methanesulfonate by a method according to Example 58.

EXAMPLE 76

N-[5-(5,6-Dimethoxy-3-methyl-1,4-benzoquinon-2-yl)methyl-2-(4-pyridyl)benzoyl]cyclohexyl-amine (methanesulfonate)

5-(3,4,5,6-Tetramethoxy-2-methylbenzyl)-2-(4-pyridyl)benzoic acid (100 mg, 0.2364 mmol) and cyclohexylamine (76 mg, 0.7663 mmol) were dissolved in methylene chloride (10 ml), then 4-dimethylaminopyridine (6 mg, 0.0491 mmol) and WSC-HCl (146 mg, 0.7616 mmol) were added thereto and the mixture was stirred for 6 hours at room temperature. The reaction solution was washed with water and dried and the solvent was evaporated.

The residue was purified by silica gel column chromatography (hexane:ethyl acetate=1:5) to give N-[5-(3,4,5,6-tetramethoxy-2-methylbenzyl)-2-(4-pyridyl)-benzoyl]cyclohexylamine (58 mg, 0.1149 mmol, 49%). The compound (58 mg, 0.1150 mmol) was dissolved in a mixed solvent of acetonitrile (9 ml) and water (3 ml), then CAN (155 mg, 0.2828 mmol) was added thereto at room temperature and the mixture was stirred for 1 hour. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (methylene chloride:methanol=95:5) to give the title compound (35 mg, 0.0738 mmol, 64%). The compound was converted to a methanesulfonate by a method according to Example 58.

EXAMPLE 77

N-[5-(5,6-Dimethoxy-3-methyl-1,4-benzoquinon-2-yl)methyl-2-(4-pyridyl)benzoyl]cyclopentylamine (methanesulfonate)

5-(3,4,5,6-Tetramethoxy-2-methylbenzyl)-2-(4-pyridyl)benzoic acid (100 mg, 0.2364 mmol) and cyclopentylamine (65 mg, 0.7633 mmol) were dissolved in methylene chloride (10 ml), then 4-dimethylaminopyridine (6 mg, 0.0491 mmol) and WSC-HCl (146 mg, 0.7616 mmol) were added thereto and the mixture was stirred for 6 hours at room temperature. The reaction solution was washed with water and dried and the solvent was evaporated.

The residue was purified by silica gel column chromatography (hexane:ethyl acetate=1:5) to give N-[5(3,4,5,6-tetramethoxy-2-methylbenzyl)-2-(4-pyridyl)-benzoyl]cyclopentylamine (58 mg, 0.1182 mmol, 50%). The compound (58 mg, 0.1183 mmol) was dissolved in a mixed solvent of acetonitrile (9 ml) and water (3 ml), then CAN (155 mg, 0.2901 mmol) was added thereto at room temperature and the mixture was stirred for 1 hour. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (5% methanol-methylene chloride) to give the title compound (28 mg, 0.0608 mmol, 51%). The compound was converted to a methanesulfonate by a method according to Example 58.

EXAMPLE 78

N-[5-(5,6-Dimethoxy-3-methyl-1,4-benzoquinon-2-yl)methyl-2-(4-pyridyl)benzoyl]cyclopropyl-amine (methanesulfonate)

5-(3,4,5,6-Tetramethoxy-2-methylbenzyl)-2-(4-pyridyl) benzoic acid (100 mg, 0.2364 mmol) and cyclopropylamine (44 mg, 0.7719 mmol) were dissolved in methylene chloride (5 ml), then 4-dimethylaminopyridine (6 mg, 0.0491 mmol) and WSC-HCl (146 mg, 0.7616 mmol) were added thereto and the mixture was stirred for 6 hours at room temperature. The reaction solution was washed with water and dried and the solvent was evaporated. The residue was purified by silica gel column chromatography (hexane:ethyl acetate=1:5) to give N-[5-(3,4,5,6-tetramethoxy-2-methylbenzyl)-2-(4-pyridyl)benzoyl]cyclopropylamine (71 mg, 0.1536 mmol, 65%).

The compound (71 mg, 0.1536 mmol) was dissolved in a mixed solvent of acetonitrile (9 ml) and water (3 ml), then CAN (207 mg, 0.3777 mmol) was added thereto at room temperature and the mixture was stirred for 1 hour. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (methylene chloride:methanol=95:5) to give the title compound (51 mg, 0.1180 mmol, 77%). The compound was converted to a methanesulfonate by a method according to Example 58.

EXAMPLE 79

N-[5-(5,6-Dimethoxy-3-methyl-1,4-benzoquinon-2-yl)methyl-2-(4-pyridyl)benzoyl]-1-ethylpropylamine (methanesulfonate)

5-(3,4,5,6-Tetramethoxy-2-methylbenzyl)-2-(4-pyridyl) benzoic acid (100 mg, 0.2364 mmol) and 1-ethylpropylamine (66 mg, 0.7586 mmol) were dissolved in methylene chloride (5 ml), then 4-dimethylaminopyridine (6 mg, 0.0491 mmol) and WSC-HCl (146 mg, 0.7616 mmol) were added thereto and the mixture was stirred for 6 hours at room temperature. The reaction solution was washed with water and dried and the solvent was evaporated. The residue was purified by silica gel column chromatography (hexane:ethyl acetate=1:5) to give N-[5-(3,4,5,6-tetramethoxy-2-methylbenzyl)-2-(4-pyridyl)benzoyl]-1-ethylpropylamine (63 mg, 0.1280 mmol, 54%).

The compound (63 mg, 0.1280 mmol) was dissolved in a mixed solvent of acetonitrile (9 ml) and water (3 ml), then CAN (172 mg, 0.3777 mmol) was added thereto at room temperature and the mixture was stirred for 1 hour. The reaction solution was poured into water, neutralized with a saturated aqueous solution of sodium hydrogen carbonate and extracted with ethyl acetate. The extract was washed with water and dried and the solvent was evaporated therefrom. The residue was purified by preparative thin layer silica gel (methylene chloride:methanol=95:5) to give the title compound (46 mg, 0.0995 mmol, 78%). The compound was converted to a methanesulfonate by a method according to Example 58.

TABLE 1

| Ref. Ex. No. | Structure | Property | FABMS (m/z) | NMR(CDCl$_3$, δ) | IR (cm$^{-1}$) |
|---|---|---|---|---|---|
| 4 | (structure: tetramethoxy-methylbenzyl diphenylmethanol with benzyloxy group at meta position) | Colorless power 80–82° C. | 42(M$^+$) 90 (100) | 2.23 (3H, s), 3.27 (3H, s), 3.81 (3H, s), 3.85 (3H, s), 3.94 (3H, s), 4.03 (1H, d, J = 10.8 Hz), 5.05 (2H, s), 5.93 (1H, d, J = 10.8 Hz), 6.80–7.00 (3H, m), 7.15–7.40 (6H, m) | 3514, 1610, 1582 (KBr) |
| 5 | (structure: tetramethoxy-methylbenzyl diphenylmethanol with benzyloxy group at para position) | Colorless power 54–56° C. | 424(M$^+$) 90 (100) | 2.23 (3H, s), 3.35 (3H, s), 3.80 (3H, s), 3.86 (3H, s), 3.94 (3H, s), 4.07 (1H, d, J = 10.8 Hz), 5.05 (2H, s), 5.93 (1H, d, J = 10.8 Hz), 6.93 (2H, d, J = 8.69 Hz), 7.19 (2H, d, J = 8.60 Hz), 7.25–7.45 (5H, m) | 3568, 2933, 1509 (KBr) |

TABLE 1-continued

| Ref. Ex. No. | Structure | Property | FABMS (m/z) | NMR(CDCl₃, δ) | IR (cm⁻¹) |
|---|---|---|---|---|---|
| 6 | (structure: tetramethoxymethylbenzene with CH(OH)-phenyl-OBn) | Colorless oil | 424(M⁺) 91 (100) | 2.16 (3H, s), 3.38 (3H, s), 3.72 (3H, s), 3.75–3.79 (1H, m), 3.86 (3H, s), 3.93 (3H, s), 5.03 (1H, d, J = 12.40 Hz), 5.09 (1H, d, J = 12.36 Hz), 6.31 (1H, d, J = 8.32 Hz), 6.83 (1H, d, J = 8.12 Hz), 6.94 (1H, t, J = 7.52 Hz), 7.11–7.18 (3H, m), 7.23–7.30 (3H, m), 7.36 (1H, d, J = 7.52 Hz) | 3500, 2937, 1599, 1464 (KBr) |
| 7 | (structure: tetramethoxymethylbenzene with CH₂-phenyl-3-OH) | Colorless oil | 318 (M⁺, 100) | 2.07 (3H, s), 3.70 (3H, s), 3.78 (3H, s), 3.91 (3H, s), 3.93 (3H, s), 3.96 (2H, s), 4.76 (1H, s), 6.54 (1H, s), 6.60 (1H, d), 6.68 (1H, d), 7.09 (1H, t) | 3387, 1589 (NaCl) |

TABLE 2

| Ref. Ex. No. | Structure | Property | FABMS (m/z) | NMR(CDCl₃, δ) | IR (cm⁻¹) |
|---|---|---|---|---|---|
| 8 | (structure: tetramethoxymethylbenzene with CH₂-phenyl-4-OH) | Colorless power 80–81° C. | 318 (M⁺, 100) | 2.08 (3H, s), 3.69 (3H, s), 3.78 (3H, s), 3.92 (3H, s), 3.93 (5H, s), 6.68 (2H, d, J = 8.52 Hz), 6.94 (2H, d, J = 8.45 Hz) | 3372, 1468, 1407 (KBr) |
| 9 | (structure: tetramethoxymethylbenzene with CH₂-phenyl-2-OH) | Colorless power 72.5–74.5° C. | 318 (M⁺, 100) | 2.25 (3H, s), 3.74 (3H, s), 3.87 (2H, s), 3.90 (6H, s), 3.96 (3H, s), 6.79–6.85 (2H, m), 7.10 (1H, t, J = 6.60 Hz), 7.21 (1H, d, J = 7.48 Hz), 7.63 (1H, br s) | 3348, 1466, 1407 (KBr) |
| 10a | (structure: tetramethoxymethylbenzene with CH₂-phenyl-CHO,OH) | Colorless oil | 346 (M⁺, 100) | 2.06 (3H, s), 3.72 (3H, s), 3.79 (3H, s), 3.92 (3H, s), 3.95 (3H, s), 4.02 (2H, s), 6.68 (1H, s), 6.81 (1H, d, J = 7.83 Hz), 7.43 (1H, d, J = 7.97 Hz), 9.82 (1H, s), 11.04 (1H, s) | 3200, 1659, 1627 (KBr) |
| 10b | (structure: tetramethoxymethylbenzene with CH₂-phenyl-OH,CHO) | Colorless power 95–98° C. | 346 (M⁺, 100) | 2.06 (3H, s), 3.67 (3H, s), 3.81 (3H, s), 3.91 (3H, s), 3.96 (3H, s), 4.35 (2H, s), 6.28 (1H, d, J = 7.6 Hz), 6.80 (1H, d, J = 8.4 Hz), 7.31 (1H, t, J = 8.0 Hz), 10.59 (1H, s) | 3400, 1655 (KBr) |

TABLE 3

| Ex. No. | Structure | Property | FABMS (m/z) | NMR(CDCl$_3$, δ) | IR (cm$^{-1}$) |
|---|---|---|---|---|---|
| 11 | (structure with OMe, MeO, Me, OH, CHO groups) | Colorless power 72–73.5 | 346 (M$^+$, 100) | 2.10 (3H, s), 3.73 (3H, s), 3.79 (3H, s), 3.93 (3H, s), 3.94 (3H, s), 3.96 (2H, s), 6.89 (1H, d, J = 8.53 Hz), 7.24 (1H, s-like), 7.32 (1H, d-like), 9.81 (1H, s), 10.84 (1H, br s) | 3232, 1664, 1486 (KBr) |
| 12 | (structure with OMe, MeO, Me, CHO, OH groups) | Colorless power 93–95° C. | 346 (M$^+$, 100) | 2.03 (3H, s), 3.72 (3H, s), 3.80 (3H, s), 3.93 (3H, s), 3.96 (3H, s), 4.00 (2H, s), 6.86 (1H, t, J = 7.56 Hz), 6.93 (1H, d, J = 7.08 Hz), 7.39 (1H, d, J = 7.28 Hz), 9.91 (1H, s), 11.46 (1H, s) | 3446, 1661, 1468 (KBr) |
| 13 | (structure with OMe, MeO, Me, CHO, OBn groups) | Colorless power 95–98° C. | 436 (M$^+$) 154 (100) | 2.03 (3H, s), 3.64 (3H, s), 3.79 (3H, s), 3.91 (3H, s), 3.96 (3H, s), 4.01 (2H, s), 5.10 (2H, s), 6.79 (1H, d, J = 8.1 Hz), 7.20–7.50 (5H, m), 7.73 (1H, d, J = 7.9 Hz), 10.47 (1H, s) | 1688, 1605 (KBr) |
| 14 | (structure with OMe, MeO, Me, CHO, CH$_2$CH$_2$Ph groups) | Colorless oil | 436 (M$^+$ + 1) 91 (100) | 2.07 (3H, s), 3.71 (3H, s), 3.78 (3H, s), 3.92 (3H, s), 3.94 (3H, s), 3.95 (2H, s), 5.15 (2H, s), 6.93 (1H, d, J = 8.60 Hz), 7.15–7.50 (6H, m), 7.64 (1H, d, J = 2.23 Hz), 10.52 (1H, s) | 2936, 1682, 1608 (KBr) |

TABLE 4

| Ref. Ex. No. | Structure | Property | FABMS (m/z) | NMR(CDCl$_3$, δ) | IR (cm$^{-1}$) |
|---|---|---|---|---|---|
| 15 | (structure with OMe, MeO, Me, CHO, OBn groups) | Colorless oil | 436 (M$^+$) 91 (100) | 2.03 (3H, s), 3.69 (3H, s), 3.79 (3H, s), 3.92 (3H, s), 3.95 (3H, s), 4.06 (2H, s), 5.11 (2H, s), 7.00 (1H, d, J = 7.26 Hz), 7.09 (1H, t, J = 7.64 Hz), 7.37–7.49 (5H, m), 7.69 (1H, d, J = 7.60 Hz), 10.33 (1H, s) | 2935, 1687, 1467 (NaCl) |
| 16 | (structure with OMe, MeO, Me, COOH, OBn groups) | Colorless power 104–105° C. | 452(M$^+$) 154 (100) | 2.04 (3H, s), 3.67 (3H, s), 3.80 (3H, s), 3.92 (3H, s), 3.96 (3H, s), 4.02 (2H, s), 5.20 (2H, s), 6.84 (1H, s), 6.90 (1H, d, J = 8.1 Hz), 7.20–7.45 (5H, m), 8.06 (1H, d, J = 8.0 Hz) | 3428, 1698, 1609 (KBr) |

TABLE 4-continued

| Ref. Ex. No. | Structure | Property | FABMS (m/z) | NMR(CDCl$_3$, δ) | IR (cm$^{-1}$) |
|---|---|---|---|---|---|
| 17 | 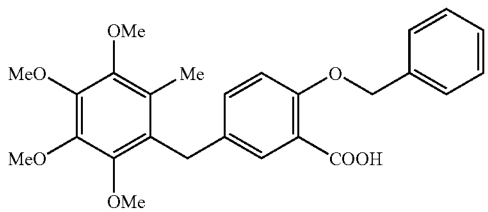 | Powder 70–71.5° C. | 459 (M$^+$) 91 (100) | 2.07 (3H, s), 3.73 (3H, s), 3.78 (3H, s), 3.92 (3H, s), 3.94 (3H, s), 3.98 (2H, s), 5.24 (2H, s) 7.00 (1H, d, J = 8.60 Hz), 7.23 (1H, d, J = 8.52 Hz), 7.41 (5H, s), 8.03 (1H, s), 10.52–10.87 (1H, br) | 3300, 1736, 1466 (NaCl) |
| 18 | 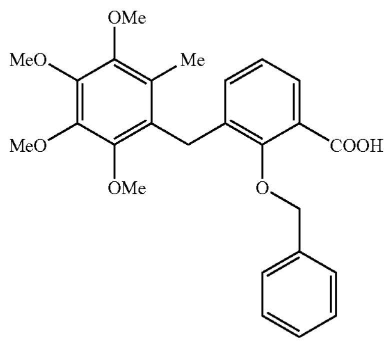 | Colorless oil | 452 (M$^+$) 91 (100) | 1.98 (3H, s), 3.69 (3H, s), 3.79 (3H, s), 3.93 (3H, s), 3.95 (3H, s), 4.08 (2H, s), 5.14 (2H, s), 6.97 (1H, d, J = 7.52 Hz), 7.09 (1H, t, J = 7.68 Hz), 7.35–7.43 (3H, m), 7.55 (2H, d, J = 7.20 Hz), 7.91 (1H, d, J = 7.64 Hz) | 3064, 1694, 1469 (NaCl) |

TABLE 5

| Ref. Ex. No. | Structure | Property | FABMS (m/z) | NMR(CDCl$_3$, δ) | IR (cm$^{-1}$) |
|---|---|---|---|---|---|
| 19 | 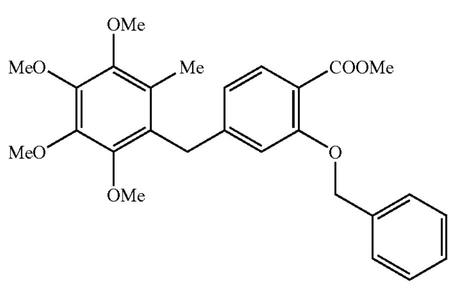 | Colorless oil | 466 (M$^+$) 91 (100) | 2.03 (3H, s), 3.67 (3H, s), 3.78 (3H, s), 3.91 (3H, s), 3.92 (3H, s), 3.94 (3H, s), 3.97 (2H, s), 5.11 (2H, s), 6.37 (1H, d, J = 7.8 Hz), 6.78 (1H, d, J = 8.3 Hz), 7.00–7.40 (6H, m) | 1732, 1581 (NaCl) |
| 20 | 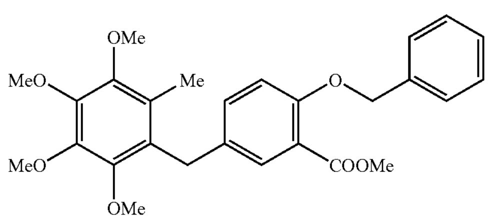 | Colorless oil | 466 (M$^+$) 154 (100) | 2.08 (3H, s), 3.70 (3H, s), 3.78 (3H, s), 3.87 (3H, s), 3.91 (3H, s), 3.93 (3H, s), 3.94 (2H, s), 5.12 (2H, s), 6.88 (1H, d, J = 8.58 Hz), 7.10 (1H, dd-like), 7.20–7.55 (5H, m), 7.61 (1H, d-like) | 2937, 1732, 1469 (NaCl) |

TABLE 5-continued

| Ref. Ex. No. | Structure | Property | FABMS (m/z) | NMR(CDCl$_3$, δ) | IR (cm$^{-1}$) |
|---|---|---|---|---|---|
| 21 | 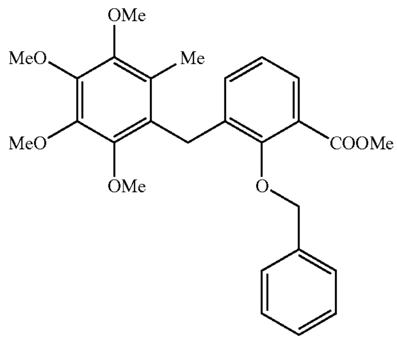 | Colorless oil | 466 (M$^+$) 91 (100) | 2.01 (3H, s), 3.66 (3H, s), 3.78 (3H, s), 3.79 (3H, s), 3.92 (3H, s), 3.97 (3H, s), 4.03 (2H, s), 5.22 (2H, s), 6.93 (2H, d, J = 8.5 Hz), 7.25–7.50 (6H, m), 7.85 (1H, d-like) | 1728, 1467 (NaCl) |
| 22 | 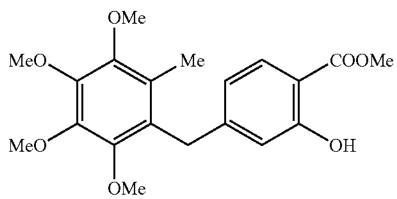 | Colorless oil | 376 (M$^+$ + 1, 100) | 2.06 (3H, s), 3.70 (3H, s), 3.78 (3H, s), 3.91 (6H, s), 3.94 (3H, s), 3.99 (2H, s), 6.60–6.75 (2H, m), 7.70 (1H, d, J = 8.0 Hz), 10.70 (1H, s) | 3178, 1674, 1622 (KBr) |

TABLE 6

| Ref. Ex. No. | Structure | Property | FABMS(m/z) | NMR(CDCl$_3$, δ) | IR (cm$^{-1}$) |
|---|---|---|---|---|---|
| 23 | 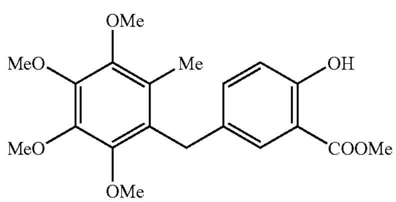 | Colorless oil | 376(M$^+$ + 1, 100) | 2.09 (3H, s), 3.71 (3H, s), 3.78 (3H, s), 3.91 (3H, s), 3.92 (5H, s), 3.94 (3H, s), 6.86 (1H, d, J = 8.55 Hz), 7.19 (1H, dd, J = 8.51 and 2.11 Hz), 7.59 (1H, d, J = 1.98 Hz), 10.57 (1H, s) | 3200, 1678, 1615 (NaCl) |
| 24 | 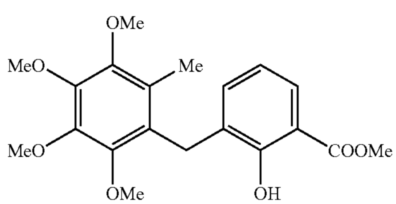 | Colorless crystals 105–107° C. | 376 (M$^+$ + 1) 154 (100) | 2.02 (3H, s), 3.71 (3H, s), 3.80 (3H, s), 3.93 (3H, s), 3.92 (3H, s), 3.96 (6H, s), 4.00 (2H, s), 6.71 (1H, t, J = 7.7 Hz), 6.82 (1H, d, J = 7.0 Hz), 7.67 (1H, d, J = 7.7 Hz), 11.20 (1H, s) | 3400, 1677, 1612 (KBr) |
| 25 | 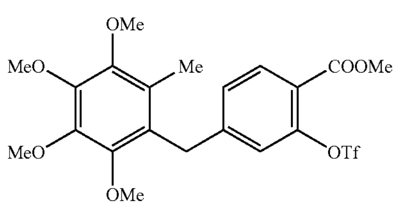 | Colorless oil | 508 (M$^+$ + 1, 100) | 2.05 (3H, s), 3.71 (3H, s), 3.78 (3H, s), 3.91 (3H, s), 3.93 (3H, s), 3.94(3H, s), 4.06 (2H, s), 6.98 (1H, s), 7.24 (1H, d-like), 7.97 (1H, d, J = 8.0 Hz) | 1736 (NaCl) |
| 26 | 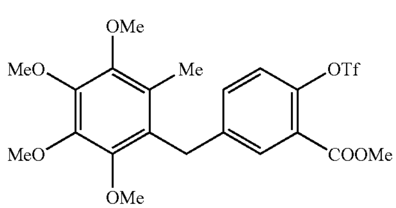 | Colorless oil | 508 (M$^+$ + 1, 100) | 2.17 (3H, s), 3.73 (3H, s), 3.79 (3H, s), 3.92 (3H, s), 3.94 (6H, s), 4.03 (2H, s), 7.15 (1H, d, J = 8.46 Hz), 7.30 (1H, d, J = 8.41 Hz), 7.87 (1H, s) | 1732, 1488 (NaCl) |

TABLE 7

| Ref. Ex. No. | Structure | Property | FABMS(m/z) | NMR(CDCl$_3$, δ) | IR (cm$^{-1}$) |
|---|---|---|---|---|---|
| 27 | (structure: trimethoxy-methyl-benzyl linked to benzene ring with COOMe and OTf) | Colorless oil | 508 (M$^+$ + 1, 100) | 2.01 (3H, s), 3.70 (3H, s), 3.79 (3H, s), 3.92 (3H, s), 3.95 (3H, s), 3.96 (3H, s), 4.10 (2H, s), 6.99 (1H, d-like), 7.26 (1H, t), 7.79 (1H, d-like) | 1735 (NaCl) |

TABLE 8

| Ex. No. | Structure | Property | FABMS(m/z) | NMR(CDCl$_3$, δ) | IR (cm$^{-1}$) |
|---|---|---|---|---|---|
| 1 | (structure: trimethoxy-methyl-benzyl linked to biphenyl-COOMe) | Colorless oil | 436 (M$^+$ + 1, 100) | 2.09 (3H, s), 3.60 (3H, s), 3.71 (3H, s), 3.75 (3H, s), 3.91 (3H, s), 3.94 (3H, s), 4.07 (2H, s), 7.11 (1H, d, J = 8.0 Hz), 7.15 (1H, s), 7.20–7.45 (5H, m), 7.72 (1H, d, J = 8.0 Hz) | 1720, 1605 (NaCl) |
| 2 | (structure: trimethoxy-methyl-benzyl linked to pyridinyl-benzene-COOMe) | Colorless oil | 438 (M$^+$ + 1, 100) | 2.09 (3H, s), 3.65 (3H, s), 3.72 (3H, s), 3.78 (3H, s), 3.91 (3H, s), 3.94 (3H, s), 4.08 (2H, s), 7.11 (1H, s), 7.17 (1H, d, J = 8.1 Hz), 7.25–7.35 (1H, m), 7.50–7.65 (1H, m), 7.84 (1H, d, J = 8.1 Hz), 8.40–8.65 (2H, m) | 1724, 1605 (NaCl) |
| 3 | (structure: trimethoxy-methyl-benzyl linked to biphenyl-COOMe isomer) | Colorless oil | 436 (M$^+$, 100) | 2.12 (3H, s), 3.60 (3H, s), 3.74 (3H, s), 3.80 (3H, s), 3.93 (3H, s), 3.95 (3H, s), 4.07 (2H, s), 7.10–7.30 (7H, m), 7.60 (1H, s) | 1737, 1732, 1716 (NaCl) |
| 4 | (structure: trimethoxy-methyl-benzyl linked to pyridinyl-benzene-COOMe isomer) | Colorless oil | 438 (M$^+$ + 1, 100) | 2.12 (3H, s), 3.64 (3H, s), 3.76 (3H, s), 3.80 (3H, s), 3.93 (3H, s), 3.95 (3H, s), 4.08 (2H, s), 7.21 (1H, d, J = 7.90 Hz), 7.25–7.35 (2H, m), 7.55–7.65 (1H, m), 7.73 (1H, s), 8.52 (1H, s), 8.56 (1H, d-like) | 1714, 1466, 1406 (KBr) |

TABLE 9

| Ex. No. | Structure | Property | FABMS (m/z) | NMR(CDCl₃, δ) | IR (cm⁻¹) |
|---|---|---|---|---|---|
| 5 | 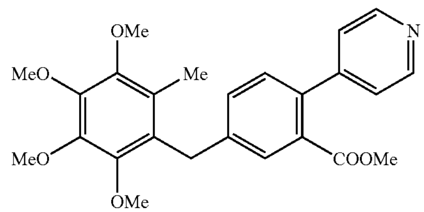 | Colorless crystals 53–54° C. | 438 (M⁺ + 1) 154 (100) | 1.91 (3H, s), 2.11 (3H, s), 3.62 (3H, s), 3.76 (3H, s), 3.80 (3H, s), 3.93 (3H, s), 3.95 (3H, s), 4.08 (2H, s), 7.15–7.25 (3H, m), 7.25–7.30 (1H, m), 7.70 (1H, s), 8.60 (2H, d-like) | 1714, 1599 (KBr) |
| 6 | 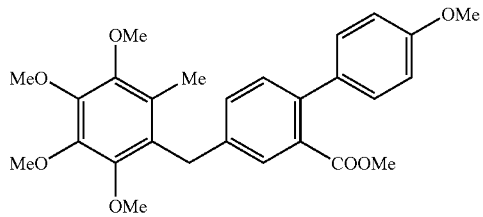 | Colorless oil | 466 (M⁺, 100) | 2.11 (3H, s), 3.63 (3H, s), 3.74 (3H, s), 3.79 (3H, s), 3.83 (3H, s), 3.93 (3H, s), 3.94 (3H, s), 4.05 (2H, s), 6.90 (2H, d, J = 8.68 Hz), 7.15–7.40 (4H, m), 7.56 (1H, s) | 1732, 1716, 1469 (NaCl) |
| 7 | 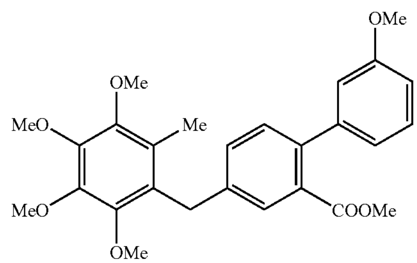 | Colorless oil | 466 (M⁺, 100) | 2.11 (3H, s), 3.62 (3H, s), 3.75 (3H, s), 3.80 (3H, s), 3.81 (3H, s), 3.93 (3H, s), 3.95 (3H, s), 4.06 (2H, s), 6.80–6.90 (3H, m), 7.15–7.30 (2H, m), 7.58 (1H, m) | 1736, 1600, 1469 (NaCl) |
| 8 | 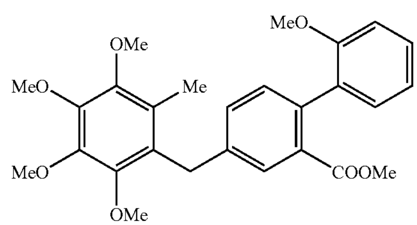 | Colorless oil | 466 (M⁺, 100) | 2.12 (3H, s), 3.62 (3H, s), 3.70 (3H, s), 3.75 (3H, s), 3.79 (3H, s), 3.93 (3H, s), 3.95 (3H, s), 4.06 (2H, s), 6.80–7.10 (2H, m), 7.15–7.35 (4H, m), 7.87 (1H, s), | 1720, 1602, 1465 (KBr) |

TABLE 10

| Ex. No. | Structure | Property | FABMS(m/z) | NMR(CDCl₃, δ) | IR (cm⁻¹) |
|---|---|---|---|---|---|
| 9 | 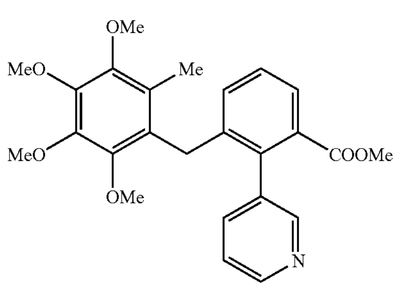 | Colorless oil | 438 (M⁺ + 1, 100) | 1.91 (3H, s), 3.60 (3H, s), 3.62 (5H, s), 3.76 (3H, s), 3.89 (3H, s), 3.93 (3H, s), 6.95 (1H, d, J = 7.6 Hz), 7.30 (1H, t, J = 7.8 Hz), 7.55–7.70 (1H, d-like), 7.77 (1H, d), 8.53 (1H, s-like), 8.64 (1H, d-like) | 1728 (NaCl) |

TABLE 10-continued

| Ex. No. | Structure | Property | FABMS(m/z) | NMR(CDCl$_3$, δ) | IR (cm$^{-1}$) |
|---|---|---|---|---|---|
| 10 | (structure) | Colorless oil | 438 (M$^+$ + 1, 100) | 1.91 (3H, s), 3.59 (3H, s), 3.60 (3H, s), 3.62 (2H, s), 3.77 (3H, s), 3.89 (3H, s), 3.97 (3H, s), 6.94 (1H, d, J = 7.8 Hz), 7.24 (2H, d, J = 5.8 Hz), 7.30 (1H, t, J = 7.8 Hz), 7.77 (1H, d, J = 7.7 Hz), 8.70 (2H, d, J = 5.8 Hz) | 1732 (KBr) |
| 11 | (structure) | Colorless crystals 118–120° C. | 422 (M$^+$, 100) | 2.08 (3H, s), 3.71 (3H, s), 3.78 (3H, s), 3.91 (3H, s), 3.93 (3H, s), 4.07 (2H, s), 7.05–7.20 (2H, m), 7.20–7.40 (5H, m), 7.82 (1H, d, J = 8.0 Hz) | 3488, 1699, 1604 (KBr) |
| 12 | (structure) | Colorless crystals 150–151° C. | 424 (M$^+$ + 1) 154 (100) | 2.09 (3H, s), 3.72 (3H, s), 3.78 (3H, s), 3.91 (3H, s), 3.94 (3H, s), 4.08 (2H, s), 7.10 (1H, s), 7.17 (1H, d, J = 8.1 Hz), 7.25–7.45 (1H, m), 7.74 (1H, d, J = 7.7 Hz), 7.87 (1H, d, J = 8.0 Hz), 8.40–8.60 (2H, m) | 3430, 1700, 1604 (KBr) |

TABLE 11

| Ex. No. | Structure | Property | FABMS(m/z) | NMR(CDCl$_3$, δ) | IR (cm$^{-1}$) |
|---|---|---|---|---|---|
| 13 | (structure) | Colorless power 145–146° C. | 422 (M$^+$) 154 (100) | 2.11 (3H, s), 3.75 (3H, s), 3.79 (3H, s), 3.93 (3H, s), 3.95 (3H, s), 4.06 (2H, s), 7.15–7.40 (2H, m), 7.72 (1H, s) | 345, 1685 (KBr) |
| 14 | (structure) | Colorless power 150–151° C. | 424 (M$^+$ + 1, 100) | 2.12 (3H, s), 3.76 (3H, s), 3.79 (3H, s), 3.93 (3H, s), 3.95 (3H, s), 4.09 (2H, s), 7.15–7.30 (2H, m), 7.30–7.45 (1H, m), 7.70–7.85 (2H, m), 8.47 (1H, d, J = 4.90 Hz), 8.58 (1H, s) | 3434, 1712, 1469 (KBr) |
| 15 | (structure) | Colorless power 199–200° C. | 424 (M$^+$ + 1) 154 (100) | 2.12 (3H, s), 3.76 (3H, s), 3.79 (3H, s), 3.93 (3H, s), 3.95 (3H, s), 4.10 (2H, s), 7.15–7.30 (2H, m), 7.38 (1H, d, J = 5.3 Hz), 7.79 (1H, s), 8.52 (2H, d, J = 4.82 Hz) | 3440, 1711, 1468 (KBr) |

TABLE 11-continued

| Ex. No. | Structure | Property | FABMS(m/z) | NMR(CDCl₃, δ) | IR (cm⁻¹) |
|---|---|---|---|---|---|
| 16 | (structure) | Colorless power 176–177° C. | 452 (M⁺) 154 (100) | 2.11 (3H, s), 3.75 (3H, s), 3.79 (3H, s), 3.83 (3H, s), 3.93 (3H, s), 3.95 (3H, s), 4.06 (2H, s), 6.89 (2H, d, J = 8.6 Hz), 7.10–7.30 (4H, m), 7.71 (1H, s) | 3432, 1691, 1613 (KBr) |

TABLE 12

| Ex. No. | Structure | Property | FABMS(m/z) | NMR(CDCl₃, 67 ) | IR (cm⁻¹) |
|---|---|---|---|---|---|
| 17 | (structure) | Colorless power 115–117° C. | 452 (M⁺, 100) | 2.12 (3H, s), 3.76 (3H, s), 3.79 (3H, s), 3.93 (3H, s), 3.95 (3H, s), 4.06 (2H, s), 6.80–6.90 (3H, m), 7.20–7.40 (3H, m), 7.71 (1H, s) | 3438, 1701, 1612 (KBr) |
| 18 | (structure) | Colorless power 57–60° C. | 452 (M⁺, 100) | 2.12 (3H, s), 3.68 (3H, s), 3.75 (3H, s), 3.79 (3H, s), 3.92 (3H, s), 3.94 (3H, s), 4.06 (2H, s), 6.85 (1H, d, J = 8.15 Hz), 7.00 (1H, t, J = 7.55 Hz), 7.15–7.35 (4H, m), 7.73 (1H, s) | 3450, 1694, 1600 (KBr) |
| 19 | (structure) | Colorless crystals 157–159° C. | 424 (M⁺+ 1) 154 (100) | 1.91 (3H, s), 3.53 (1H, d, J = 16 Hz), 3.61 (3H, s), 3.69 (1H, d, J = 16 Hz), 3.77 (3H, s), 3.88 (1H, s), 3.93 (3H, s), 6.94 (1H, d, J = 7.8 Hz), 7.31 (1H, t, J = 7.8 Hz), 7.35–7.40 (1H, m), 7.75–7.85 (1H, m), 8.44 (1H, s-like), 8.51 (1H, d-like) | 3443, 1717 (KBr) |
| 20 | (structure) | Colorless crystals >200° C. | 424 (M⁺+ 1) 154 (100) | 1.92 (3H, s), 3.59 (2H, s), 3.62 (3H, s), 3.77 (3H, s), 3.89 93H, s), 3.94 (3H, s), 6.91 91H, d, J = 7.8 Hz), 7.31 91H, t, J = 7.8 Hz), 7.43 (2H, d, J = 5.9 hz), 7.83 91H, d, J = 7.6 Hz), 8.61 (2H, d, J = 5.7 Hz) | 3432, 1706, 1610 (KBr) |

TABLE 13

| Ex. No. | Structure | Property | FABMS(m/z) | NMR(CDCl$_3$, δ) | IR (cm$^{-1}$) |
|---|---|---|---|---|---|
| 21 | 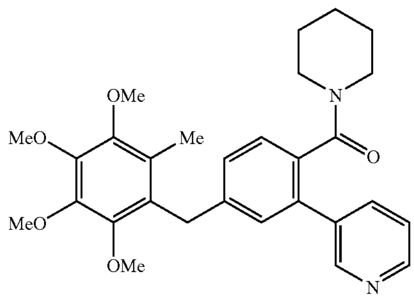 | Colorless oil | 491 (M$^+$ + 1, 100) | 0.60–0.80 (1H, m), 1.10–1.60 (5H, m), 2.10 (3H, s), 2.65–2.80 (1H, m), 2.85–3.05 (1H, m), 3.40–3.60 (2H, m), 3.76 (3H, s), 3.78 (3H, s), 3.92 (3H, s), 3.94 (3H, s), 4.08 (2H, s), 7.10–7.40 (4H, m), 7.75–7.90 (1H, m), 8.50–8.70 (2H, m) | 1634 (NaCl) |
| 22 | 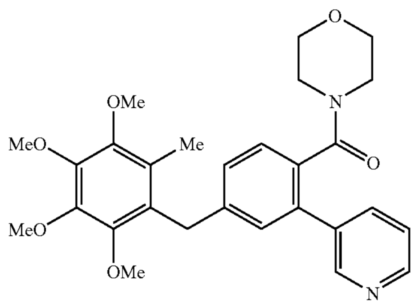 | Colorless oil | 493 (M$^+$+ 1, 100) | 2.09 (3H, s), 2.60–2.80 (2H, m), 2.90–3.05 (1H, m), 3.20–3.40 (2H, m), 3.50–3.65 (3H, m), 3.76 (3H, s), 3.76 (3H, s), 3.78 (3H, s), 3.92 (3H, s), 3.94 (3H, s), 4.08 (2H, s), 7.10–7.25 (2H, m), 7.25–7.40 (2H, m), 7.70–7.85 (1H, m), 8.55–8.70 (2H, m) | 1634, 1606 (NaCl) |
| 23 | 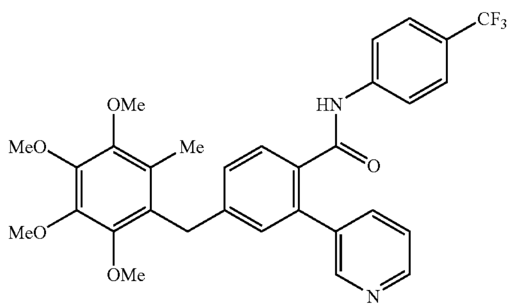 | Colorless crystals 64–67° C. | 567 (M$^+$ + 1) 154 (100) | 2.10 (3H, s), 3.76 (3H, s), 3.79 (3H, s), 3.92 (3H, s), 3.94 (3H, s), 4.10 92H, s), 7.10–7.55 (8H, m), 7.60–7.80 (2H, m), 8.45–8.70 (2H, m) | 1684, 1654, 1604 (KBr) |
| 24 | 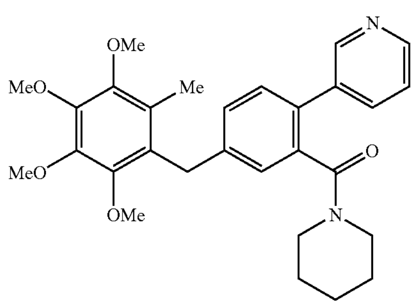 | Colorless oil | 491 (M$^+$ + 1, 100) | 0.60–0.75 (1H, m), 1.10–1.60 (5H, m), 2.10 (3H, s), 2.65–2.80 (1H, m), 2.85–3.00 (1H, m), 3.40–3.55 (2H, m), 3.75 (3H, s), 3.79 (3H, s), 3.93 (3H, s), 3.95 (3H, s), 4.06 (2H, s), 7.17 (1H, s), 7.20 (1H, d, J = 8 Hz), 7.75–7.85 (1H, m), 8.57 (1H, dd, J = 5 and 1 Hz), 8.65 91H, d, J = 2 Hz) | 1630 (NaCl) |

TABLE 14

| Ex. No. | Structure | Property | FABMS(m/z) | NMR(CDCl$_3$, δ) | IR (cm$^{-1}$) |
|---|---|---|---|---|---|
| 25 | 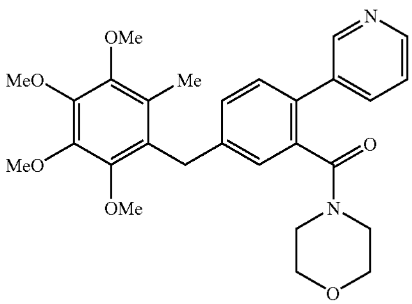 | Colorless oil | 493 (M$^+$ + 1, 100) | 2.10 (3H, s), 2.60–2.85 (2H, m), 2.90–3.05 (1H, m), 3.20–3.40 (2H, m), 3.45–3.70 (3H, m), 3.75 (3H, s), 3.80 (3H, s), 3.93 (3H, s), 3.95 (3H, s), 4.07 (2H, s), 7.15–7.40 (4H, m), 7.70–7.85 (1H, m), 8.61 (1H, dd, J = 5 and 1 Hz), 8.66 (1H, d, J = 2 Hz) | 1632 (Na$_2$Cl) |
| 26 | 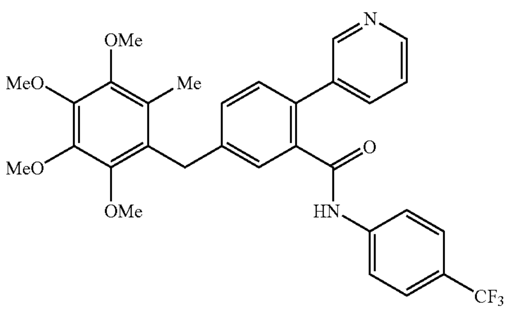 | Colorless crystals 206–208° C. | 567 (M$^+$ + 1, 100) | 2.13 93H, s), 3.79 (3H, s), 3.80 (3H, s), 3.93 (3H, s), 3.95 (3H, s), 4.10 (2H, s), 7.20–7.55 (8H, m), 7.58 (1H, s), 7.74 (1H, d, J = 7.4 Hz), 8.51 (1H, d-like), 8.60 (1H, s) | 1684, 1609 (KBr) |
| 27 | 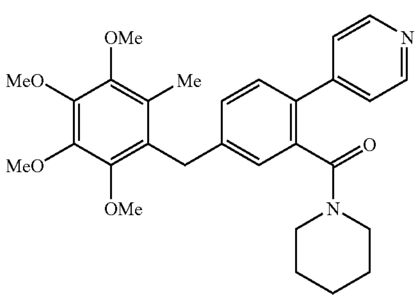 | Colorless oil | 491 (M$^+$ + 1, 100) | 0.60–0.80 (1H, m), 1.05–1.60 (5H, m), 2.10 (3H, s), 2.60–2.80 (1H, m), 2.80–3.00 (1H, m), 3.40–3.60 (2H, m), 3.74 (3H, s), 3.79 (3H, s), 3.93 (3H, s), 3.95 (3H, s), 4.06 (2H, s), 7.17 (1H, s), 7.20 (1H, d, J = 8.0 Hz), 7.31 (1H, d, J = 8.0 Hz), 7.35–7.45 (2H, m), 8.50–8.70 (2H, m) | 1634 (NaCl) |
| 28 | 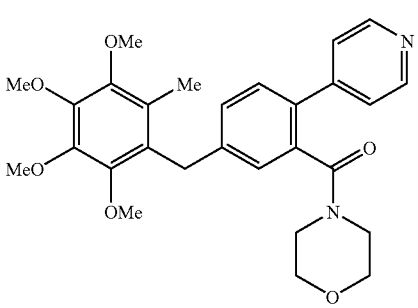 | Colorless crystals 53–55° C. | 493 (M$^+$ + 1, 100) | 2.10 (3H, s), 2.60–2.85 (2H, m), 2.90–3.05 (1H, m), 3.20–3.40 (2H, m), 3.50–3.70 (3H, m), 3.75 (3H, s), 3.80 (3H, s), 3.93 (3H, s), 3.95 (3H, s), 4.07 (2H, s), 7.15–7.35 (3H, m), 7.35–7.40 (2H, m), 8.55–8.70 (2H, m) | 1636 (KBr) |

TABLE 15

| Ex. No. | Structure | Property | FABMS(m/z) | NMR(CDCl$_3$, δ) | IR (cm$^{-1}$) |
|---|---|---|---|---|---|
| 29 | 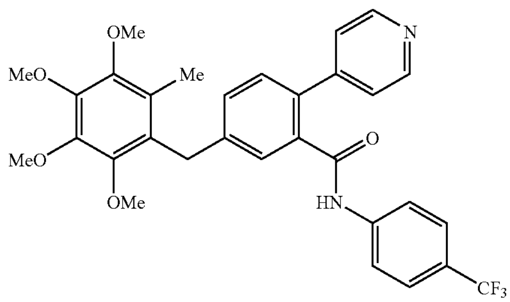 | Colorless oil | 567 (M$^+$, 100) | 2.13 (3H, s), 3.79 (3H, s), 3.80 (3H, s), 3.93 (3H, s), 3.95 (3H, s), 4.10 (2H, s), 7.15–7.40 (7H, m), 7.45–7.65 (2H, m), 8.55–8.65 (2H, m) | 3438, 1710, 1612 (KBr) |
| 30 | 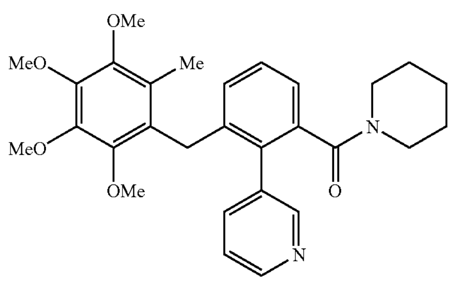 | Colorless oil | 491 (M$^+$ + 1) 154 (100) | 1.10–1.80 (6H, m), 1.90 (3H, s), 2.85–3.00 (1H, m), 3.05–3.30 (2H, m), 3.48 (3H, s), 3.40–3.60 (2H, m), 3.65 (3H, s), 3.76 (3H, s), 3.89 (3H, s), 3.93 (3H, s), 3.85–4.00 (1H, m), 6.84 (1H, d, J = 7.6 Hz), 7.10–7.45 (3H, m), 7.55–7.90 (1H, m), 8.55–8.80 (2H, m) | 1615 (CHCl3) |
| 31 | 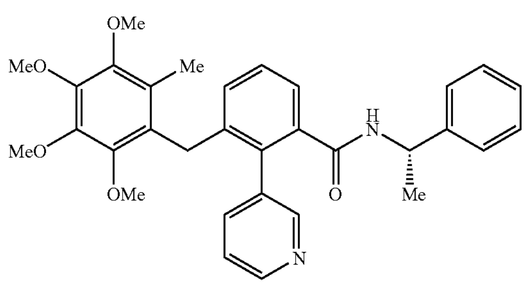 | Colorless oil | 527 (M$^+$ + 1) 154 (100) | 1.16, 1.27 (3H, each d, J = 6.9 Hz), 1,88, 1.89 (3H, each s), 3.50–3.80 (2H, m), 3.62 (3H, s), 3.75 (3H, s), 3.88 (3H, s), 3.93 (3H, s), 4.90–5.10 (1H, m), 5.45–5.60 (1H, m), 6.80–7.40 (9H, m), 7.70 (1H, t-like), 8.50–8.70 (2H, m) | 1651 (CHCl3) |
| 32 | 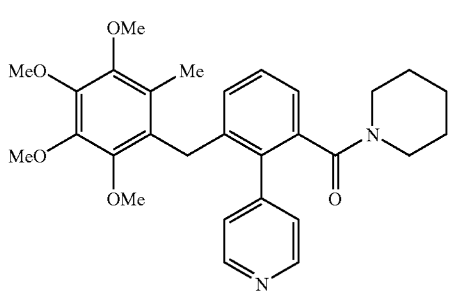 | Colorless oil | 491 (M$^+$ + 1) 154 (100) | 1.00–1.75 (6H, m), 1.89 (3H, s), 2.75–2.95 (1H, m), 3.05–3.25 (2H, m), 3.48 (3H, s), 3.40–3.70 (2H, m), 3.66 (3H, s), 3.76 (3H, s), 3.93 (3H, s), 3.85–4.00 (1H, m), 6.84 (1H, d, J = 7.9 Hz), 7.10–7.35 (3H, m), 7.46 (1H, br s), 8.69 (2H, br s) | 1615 (CHCl3) |

TABLE 16

| Ex. No. | Structure | Property | FABMS(m/z) | NMR(CDCl₃, δ) | IR (cm⁻¹) |
|---|---|---|---|---|---|
| 33 | (structure: 2,3,4-trimethoxy-6-methylbenzyl attached to benzamide with N-(1-phenylethyl) group and 4-pyridyl substituent) | Colorless oil | 527 ($M^+ + 1$) 154 (100) | 1.23 (3H, d, J = 6.8 Hz), 1.88 (3H, s), 3.55–3.70 (2H, m), 3.62 (3H, s), 3.76 (3H, s), 3.88 (3H, s), 3.93 (3H, s), 4.90–5.05 (1H, m), 5.49 (1H, d, J = 7.9 Hz), 6.85 (1H, d, J = 8.0 Hz), 7.03 (2H, d, J = 6.4 Hz), 7.20–7.35 (6H, m), 7.43 (1H, d, J = 7.6 Hz), 8.60–8.70 (2H, m) | 1652 (CHCl3) |
| 34 | (structure: 2,3,4-trimethoxy-6-methylbenzyl attached to benzamide with N-(4-trifluoromethylphenyl) group and 4-pyridyl substituent) | Colorless power 194–195° C. | 567 ($M^+ + 1$, 100) | 1.92 (3H, s), 3.65 (3H, s), 3.40–3.70 (2H, m), 3.70 (2H, s), 3.65 (3H, s), 3.90 (3H, s), 3.94 (3H, s), 6.97 (1H, d, J = 7.8 Hz), 7.20–7.30 (1H, m), 7.30–7.60 (8H, m), 8.71 (2H, d, J = 5.8 Hz) | 1660, 1604 (KBr) |
| 35 | (structure: 2,3-dimethoxy-5-methyl-1,4-benzoquinone with CH₂ linker to biphenyl-2-carboxylic acid) | Yellow crystals 184–185° C. | 393 ($M^+ + 1$) 154 (100) | 2.08 (3H, s), 3.91 (2H, s), 3.99 (6H, s), 7.15 (1H, m), 7.21 (1H, d-like), 7.25–7.45 (5H, m), 7.84 (1H, d, J = 8.0 Hz) | 344, 1648, 1608 (KBr) |
| 36 | (structure: 2,3-dimethoxy-5-methyl-1,4-benzoquinone with CH₂ linker to phenyl with COOH and 3-pyridyl substituent) | Yello crystals 108–110° C. | 393 ($M^+ + 1$) 154 (100) | 2.10 (3H, s), 3.92 (2H, s), 3.99 (6H, s), 7.10–7.45 (3H, m), 7.76 (1H, d, J = 7.8 Hz), 7.88 (1H, d, J = 8.0 Hz), 8.40–8.60 (2H, m) | 3430, 1648, 1612 (KBr) |

TABLE 17

| Ex. No. | Structure | Property | FABMS(m/z) | NMR(CDCl₃, δ) | IR (cm⁻¹) |
|---|---|---|---|---|---|
| 37 | (structure: 2,3-dimethoxy-5-methyl-1,4-benzoquinone with CH₂ linker to biphenyl-carboxylic acid) | Colorless crystals 150–152° C. | 393 ($M^+ + 1$) 154 (100) | 2.12 (3H, s), 3.90 (2H, s), 4.00 (6H, s), 7.20–7.35 (7H, m), 7.72 (1H, s) | 3447, 1652, 1612 (KBr) |

TABLE 17-continued

| Ex. No. | Structure | Property | FABMS(m/z) | NMR(CDCl$_3$, δ) | IR (cm$^{-1}$) |
|---|---|---|---|---|---|
| 38 | 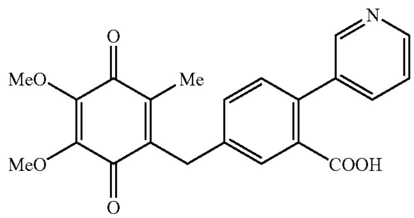 | Colorless crystals >200° C. | 394 (M$^+$ + 1) 154 (100) | 2.11 (3H, s), 3.95 (2H, s), 3.98 (3H, s), 3.99 (3H, s), 7.20–7.45 (3H, m), 7.62 (1H, s), 7.83 (1H, d, J = 7.65 Hz), 8.45 (1H, d, J = 4.46 Hz), 8.52 (1H, s) (CD3OD + CDCl3) | 3388, 1651, 1610 (KBr) |
| 39 | 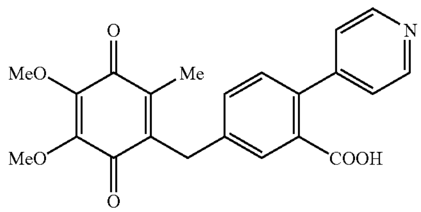 | Yellow crystals 186–188° C. | 394 (M$^+$ + 1) 154 (100) | 2.12 (3H, s), 3.91 (2H, s), 3.99 (6H, s), 7.21 (2H, d, J = 7.86 Hz), 7.25–7.40 (3H, m), 7.74 (1H, s), 8.47 (2H, d, J = 4.82 Hz) | 3447, 1652, 1612 (KBr) |
| 40 | 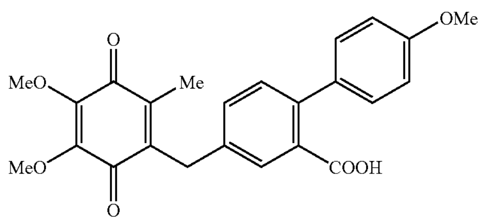 | Yello crystals 164–166° C. | 423 (M$^+$ 1) 154 (100) | 2.12 (3H, s), 3.82 (3H, s), 3.90 (2H, s,), 4.00 (6H, s), 6.89 (2H, d-like), 7.15–7.30 (3H, m), 7.34 (1H, d, J = 7.7 Hz), 7.69 (1H, s) | 3437, 1672, 1612 (KBr) |

TABLE 18

| Ex. No. | Structure | Property | FABMS(m/z) | NMR(CDCl$_3$, δ) | IR (cm$^{-1}$) |
|---|---|---|---|---|---|
| 41 | 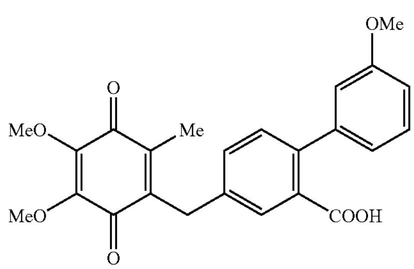 | Yellow crystals 141–142° C. | 423 (M$^+$ + 1) 154 (100) | 2.13 (3H, s), 3.80 (3H, s), 3.91 (2H, s), 4.00 (6H, s), 4.00 (6H, s), 6.80–6.95 (3H, m), 7.20–7.40 (3H, m), 7.71 (1H, s) | 1676, 1652, 1612 (KBr) |
| 42 | 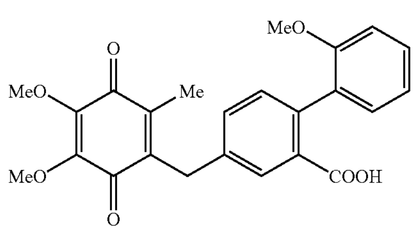 | Yellow crystals 77–79° C. | 422 (M$^+$) 154 (100) | 2.13 (3H, s), 3.69 (3H, s), 3.91 (2H, s), 4.00 (6H, s) 6.87 (1H, d, J = 8.3 Hz), 7.02 (1H, t, J = 7.4 Hz), 7.15–7.45 (4H, m), 7.72 (1H, s) | 1649, 1612 (KBr) |

TABLE 18-continued

| Ex. No. | Structure | Property | FABMS(m/z) | NMR(CDCl₃, δ) | IR (cm⁻¹) |
|---|---|---|---|---|---|
| 43 | 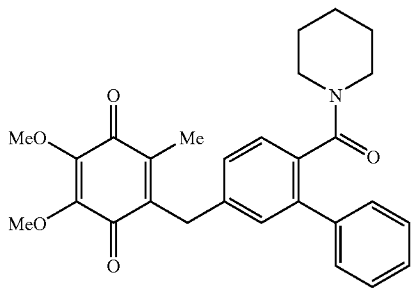 | Yellow oil | 460 (M⁺ + 1) 154 (100) | 0.45–0.60 (1H, m), 1.00–1.65 (5H, m), 2.09 (3H, s), 2.60–2.75 (1H, m), 2.80–2.95 (1H, m), 3.30–3.45 (1H, m), 3.50–3.65 (1H, m), 3.88 (1H, d, J = 14 Hz), 3.92 (1H, d, J = 14 Hz), 3.99 (3H, s), 4.00 (3H, s), 7.10–7.50 (8H, m) | 1651, 1611 (CHCl3) |
| 44 | 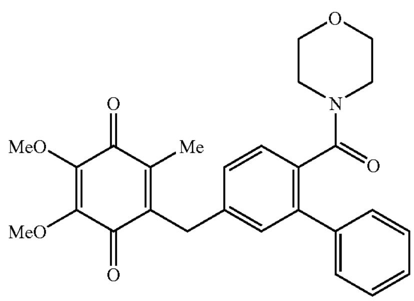 | Yellow powder 62–64° C. | 462 (M⁺ + 1) 154 (100) | 2.09 (3H, s), 2.35–2.50 (1H, m), 2.60–2.75 (1H, m), 2.85–3.00 (1H, m), 3.15–3.30 (2H, m), 3.35–3.50 (1H, m), 3.50–3.75 (2H, m), 3.87 (1H, d, J = 14 Hz), 3.92 (1H, d, J = 14 Hz), 3.99 (3H, s), 4.00 (3H, s), 7.15–7.50 (8H, m) | 1654 (KBr) |

TABLE 19

| Ex. No. | Structure | Property | FABMS(m/z) | NMR(CDCl₃, δ) | IR (cm⁻¹) |
|---|---|---|---|---|---|
| 45 | 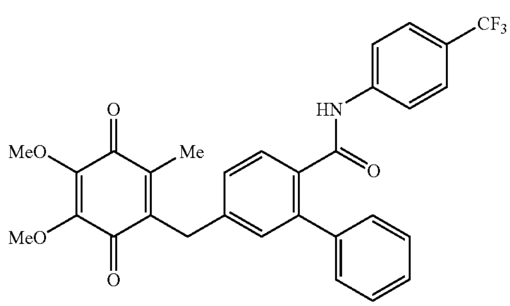 | Yellow powder 68–70° C. | 536 (M⁺ + 1) 154 (100) | 2.11 (3H, s), 3.94 (2H, s), 4.00 (6H, s), 6.95 (1H, s), 7.10–7.35 (4H, m), 7.35–7.50 (7H, m), 7.83 (1H, d, J = 8.0 Hz) | 1651, 1605 (KBr) |
| 46 | 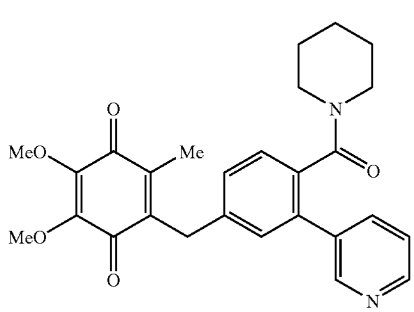 | Yellow oil | 461 (M⁺ + 1) 154 (100) | 0.60–0.80 (1H, m), 1.10–1.60 (5H, m), 2.11 (3H, s), 2.65–2.80 (1H, m), 2.85–3.05 (1H, m), 3.45–3.55 (2H, m), 3.92 (2H, s), 4.00 (6H, s), 7.15–7.40 (4H, m), 7.75–7.85 (1H, m), 8.55–8.70 (2H, m) | 1654, 1612 (CHCl3) |

TABLE 19-continued

| Ex. No. | Structure | Property | FABMS(m/z) | NMR(CDCl$_3$, δ) | IR (cm$^{-1}$) |
|---|---|---|---|---|---|
| 47 | 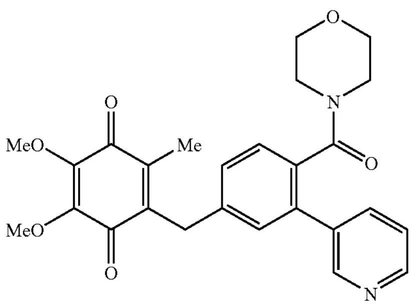 | Yellow crystals 126–127° C. | 463 (M$^+$ + 1) 154 (100) | 2.11 (3H, s), 2.60–2.80 (2H, m) 2.90–3.10 (1H, m), 3.20–3.40 (2H, m), 3.45–3.70 (3H, m), 3.92 (2H, s), 4.00 (6H, s), 6.78 (2H, d, J = 8.9 Hz), 6.92 (1H, s), 7.14 (2H, d, J = 8.9 Hz), 7.20–7.40 (4H, m), 7.70–7.85 (1H, m), 8.60–8.70 (1H, m) | 1630 (KBr) |
| 48 | 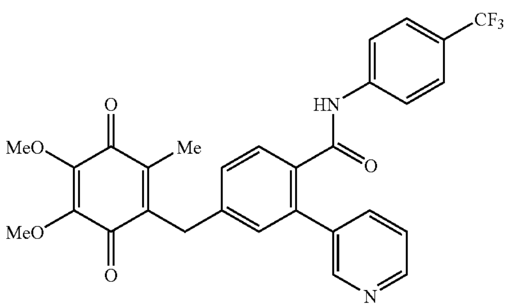 | Yellow crystals 127–130° C. | 537 (M$^+$ + 1) 154 (100) | 2.11 (3H, s), 3.93 (2H, s), 4.00 (6H, s), 7.15–7.60 (8H, m), 7.60–7.80 (2H, m), 8.50–8.65 (2H, m) | 1654, 1608 (KBr) |

TABLE 20

| Ex. No. | Structure | Property | FABMS(m/z) | NMR(CDCl$_3$, δ) | IR (cm$^{-1}$) |
|---|---|---|---|---|---|
| 49 | 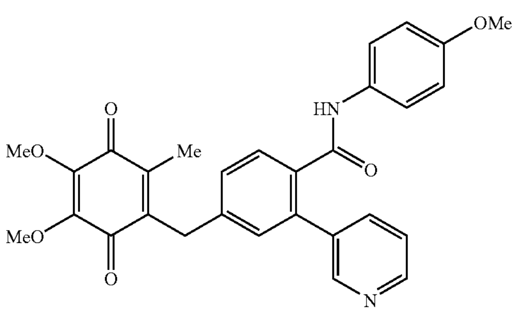 | Yellow crystals 143–145° C. | 499 (M$^+$ + 1) 154 (100) | 2.12 (3H, s), 3.76 (3H, s), 3.94 (2H, s), 4.00 (6H, s), 6.78 (2H, d, J = 8.9 Hz), 6.92 (1H, s), 7.14 (2H, d, J = 8.9 Hz), 7.20–7.40 (3H, m), 7.68 (1H, d, J = 7.9 Hz), 7.76 (1H, d, J = 7.8 Hz), (1H, d, J = 4.0 Hz), 8.68 (1H, s) | 1654, 1612 (KBr) |
| 50 | 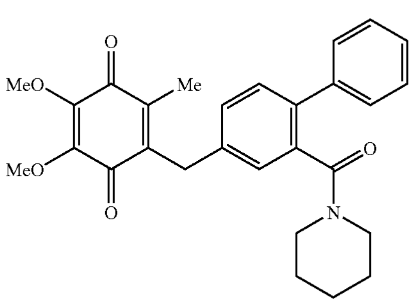 | Yellow oil | 460 (M$^+$ + 1) 154 (100) | 0.40–0.60 (1H, m), 1.00–1.55 (5H, m), 2.10 (3H, s), 2.60–2.75 (1H, m), 2.75–2.95 (1H, m), 3.25–3.45 (1H, m) 3.55–3.70 (1H, m), 3.84 (1H, d, J = 14 Hz), 3.93 (1H, d, J = 14 Hz), 4.00 (3H, s), 4.01 (3H, s), 7.10–7.50 (8H, m) | 1635 (CHCl3) |

TABLE 20-continued

| Ex. No. | Structure | Property | FABMS(m/z) | NMR(CDCl$_3$, δ) | IR (cm$^{-1}$) |
|---|---|---|---|---|---|
| 51 | 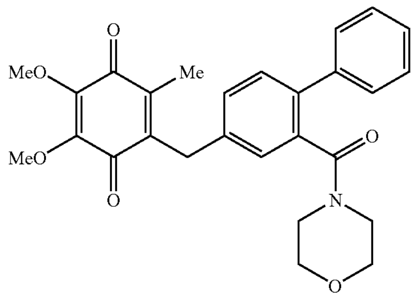 | Yellow crystals 105–106° C. | 462 (M$^+$ + 1) 154 (100) | 2.11 (3H, s), 2.30–2.45 (1H, m), 2.60–2.75 (1H, m), 2.85–3.00 (1H, m), 3.10–3.30 (2H, m), 3.30–3.45 (1H, m), 3.50–3.65 (1H, m), 3.65–3.80 (1H, m), 3.85 (1H, d, J = 14 Hz), 3.92 (1H, d, J = 14 Hz), 4.00 (3H, s), 4.01 (3H, s), 7.10–7.50 (8H, m) | 1632 (KBr) |
| 52 | 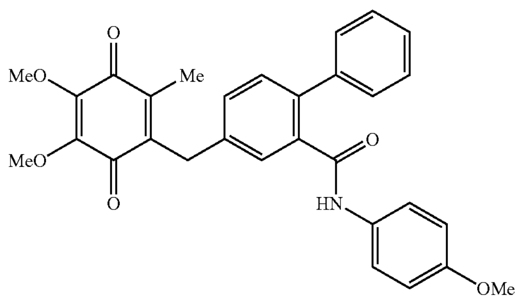 | Yellow crystals 159–160° C. | 498 (M$^+$ + 1) 154 (100) | 2.14 (3H, s), 3.95 (3H, s), 4.00 (3H, s), 4.01 (3H, s), 6.96 (1H, s), 7.18 (1H, d, J = 8.4 Hz), 7.30–7.50 (9H, m), 7.69 (1H, s) | 1639, 1607 (KBr) |

TABLE 21

| Ex. No. | Structure | Property | FABMS (m/z) | NMR(CDCl$_3$, δ) | IR (cm$^{-1}$) |
|---|---|---|---|---|---|
| 53 | 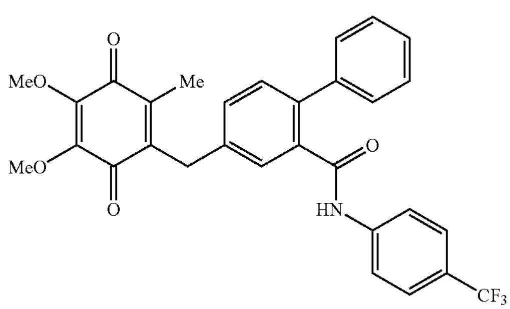 | Yellow crystals 125–126° C. | 536 (M$^+$+ 1) 154 (100) | 2.15(3H, s), 3.95(2H, s), 4.00(3H, s), 4.01(3H, s), 6.96(1H, s), 7.18(2H, d, J=8.4Hz), 7.30–7.50(9H, m), 7.69(1H, s) | 1665, 1610 (KBr) |
| 54 | 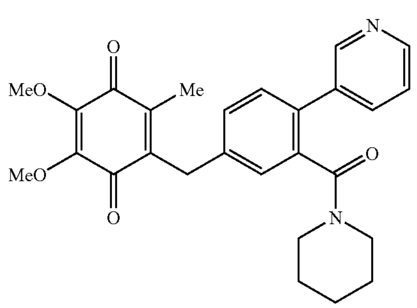 | Yellow crystals 54–56° C. | 461 (M$^+$+ 1) 154 (100) | 0.55–1.70(6H, m), 2.10(3H, s), 2.65–3.00(2H, m), 3.35–3.65(2H, m), 3.86(1H, d, J=14.2Hz), 3.95(1H, d, J=14.7Hz), 4.00(3H, s), 4.01(3H, s), 7.19 (1H, s), 7.20–7.40(3H, m), 7.81(1H, d, J=7.9 Hz), 8.59(2H, d, J=3.8Hz), 8.66(1H, s) | 1635 (KBr) |

TABLE 21-continued

| Ex. No. | Structure | Property | FABMS (m/z) | NMR(CDCl$_3$, δ) | IR (cm$^{-1}$) |
|---|---|---|---|---|---|
| 55 | 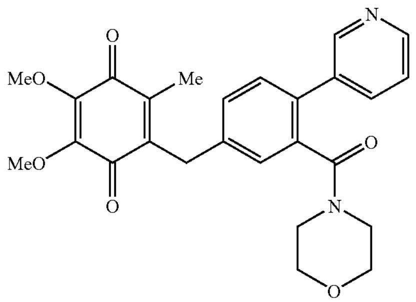 | Yellow powder 63–65° C. | 463 (M$^+$+ 1) 154 (100) | 2.11(3H, s), 2.55–2.80(2H, m), 2.90–3.10(1H, m), 3.20–3.40(2H, m), 3.45–3.70(3H, m), 3.87(1H, d, J=14.1Hz), 3.94(1H, d, J=13.3Hz), 4.00 (3H, s), 4.01(3H, s), 7.15–7.40(4H, m), 7.78(1H, d, J=7.9 Hz), 8.62(1H, d, J=3.7Hz), 8.65(1H, s-like) | 1635, 1612 (KBr) |
| 56 | 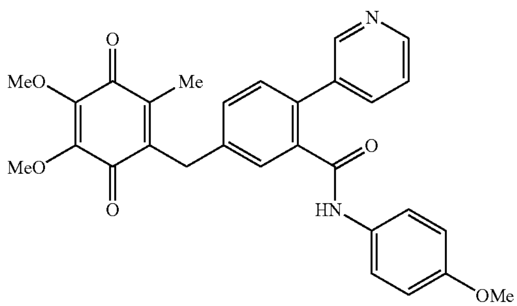 | Yellow crystals 157–158° C. | 499 (M$^+$+ 1) 154 (100) | 2.14(3H, s), 3.76(3H, s), 3.94(2H, s), 4.01(6H, s), 6.79(2H, d, J=8.9Hz), 6.92 (1H, br s), 7.14(2H, d, J=8.9Hz), 7.20–7.45(3H, m), 7.56(1H, s), 7.76(1H, d-like), 8.58(1H, d-like), 8.69(1H, s) | 1655, 1611 (KB) |

TABLE 22

| Ex. No. | Structure | Property | FABMS (m/z) | NMR(CDCl$_3$, δ) | IR (cm$^{-1}$) |
|---|---|---|---|---|---|
| 57 | 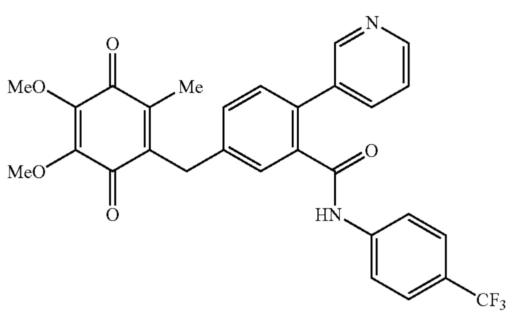 | Yellow crystals 193–194° C. | 537 (M$^+$+ 1) 154(100) | 2.14(3H, s), 3.95(2H, s), 4.00(3H, s), 4.01(3H, s), 7.15–7.45(6H, m), 7.51 (2H, d, J=8Hz), 7.58(1H, s), 7.73(1H, d=8Hz), 8.58(1H, d, J=5Hz), 8.67(1H, s) | 1684, 1656, 1614 (KBr) |
| 58a | 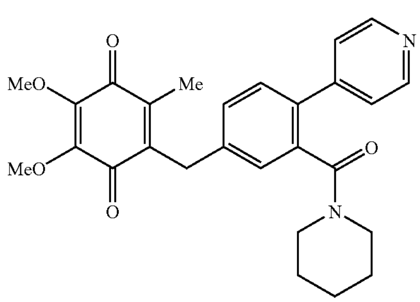 | Yellow crystals 70–72° C. | 461 (M$^+$+ 1) 154 (100) | 0.55–1.75(6H, m), 2.10(3H, s), 2.60–3.00(2H, m), 3.40–3.65(2H, m), 3.86 (1H, d, J=14Hz), 3.94(1H, d, J=14Hz), 4.00(3H, s), 4.01(3H, s), 7.18(1H, s), 7.25–7.40(2H, m), 7.39(2H, d, J=6 Hz), 8.62(2H, d, J=5Hz) | 1642, 1612 (KBr) |

TABLE 22-continued

| Ex. No. | Structure | Property | FABMS (m/z) | NMR(CDCl$_3$, δ) | IR (cm$^{-1}$) |
|---|---|---|---|---|---|
| 58b | (structure: 2,3-dimethoxy-5-methyl-6-[[3-(piperidin-1-ylcarbonyl)-4-(pyridin-4-yl)phenyl]methyl]-1,4-benzoquinone · CH$_2$SO$_2$H) | Yellow crystals 153–154° C. | 461 (M$^+$+ 1) 154 (100) | 0.70–2.00(6H, m), 2.11(3H, s), 2.93(3H, s), 2.70–3.20(2H, m), 3.30–3.80(2H, m), 3.94(2H, s), 4.01(6H, s), 7.25(1H, s), 7.42(2H, s), 7.96(2H, d, J=6.3Hz), 8.85 (2H, d, J=6.4Hz) | 1634, 1612 (KBr) |
| 59 | (structure: 2,3-dimethoxy-5-methyl-6-[[3-(morpholin-4-ylcarbonyl)-4-(pyridin-4-yl)phenyl]methyl]-1,4-benzoquinone) | Yellow crystals 70–72° C. | 463 (M$^+$+ 1) 154 (100) | 2.11(3H, s), 2.55–2.80(2H, m), 2.90–3.10 (1H, m), 3.20–3.40(2H, m), 3.45–3.70(3H, m), 3.87(2H, d, J=14.1Hz), 3.87(3H, d, J=14.1Hz), 3.94(1H, d, J=13.3Hz), 4.00 (1H, s), 4.01(3H, s), 7.15–7.40(4H, m), 7.78(1H, d, J=7.86 Hz), 8.62(1H, d, J=3.74 Hz), 8.65(1H, s-like) | 1638 (KBr) |

TABLE 23

| Ex. No. | Structure | Property | FABMS (m/z) | NMR(CDCl$_3$, δ) | IR (cm$^{-1}$) |
|---|---|---|---|---|---|
| 60a | (structure: 2,3-dimethoxy-5-methyl-6-[[3-[(4-methoxyphenyl)aminocarbonyl]-4-(pyridin-4-yl)phenyl]methyl]-1,4-benzoquinone) | Yellow crystals 151–152° C. | 499 (M$^+$+ 1) 154 (100) | 2.14(3H, s), 3.77(3H, s), 3.94(3H, s), 4.01(6H, s), 6.70–6.85(3H, m), 7.11(1H, d, J=9Hz), 7.25–7.45(4H, m), 7.56(1H, s), 8.63(2H, d, J=5.7Hz) | 1638, 1605 (KBr) |
| 60b | (structure: same as 60a · HCl) | Yellow crystals 169–171° C. | 499 (M$^+$+ 1) 154 (100) | 2.12(3H, s), 3.77(3H, s), 3.97(3H, s), 3.98(3H, s), 4.04(2H, s), 6.87(2H, d, J=8.9Hz), 7.40(2H, d, J=9.0 Hz), 7.45–7.70(3H, m), 8.06(2H, d, J=6.0 Hz), 8.79 (2H, d, J=5.9Hz) | 1654 (KBr) |

TABLE 23-continued

| Ex. No. | Structure | Property | FABMS (m/z) | NMR(CDCl$_3$, δ) | IR (cm$^{-1}$) |
|---|---|---|---|---|---|
| 61 | 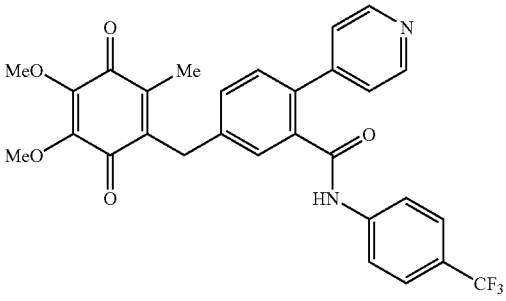 | Yellow crystals 106–108° C. | 537 (M$^+$+ 1) 154(100) | 2.14(3H, s), 3.94(2H, s), 4.01(6H, s), 7.10–7.60(10H, m), 8.61(2H, d, J= 5.3Hz) | 1654, 1608 (KBr) |
| 62 | 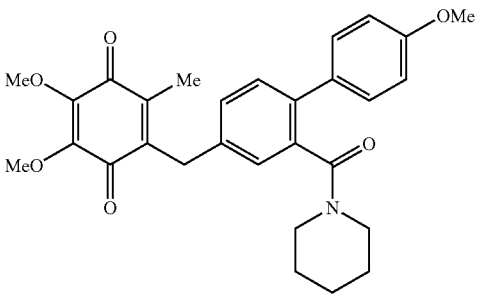 | Yellow oil | 490 (M$^+$) 154 (100) | 0.50–0.70(1H, m), 1.05–1.55(5H, m), 2.09(3H, s), 2.60–2.75(1H, m), 2.80–2.95 (1H, m), 3.35–3.50(1H, m), 3.50–3.65(1H, m), 3.83(1H, d, J=14 Hz), 3.92(1H, d, J=14Hz), 4.00(3H, s), 4.01(3H, s), 6.91 (2H, d, J=8.6Hz), 7.13(3H, s), 7.20–7.30 (2H, m), 7.37(2H, d, J=8.6 Hz) | 1651, 1633, 1614 (KBr) |

TABLE 24

| Ex. No. | Structure | Property | FABMS (m/z) | NMR(CDCl$_3$, δ) | IR (cm$^{-1}$) |
|---|---|---|---|---|---|
| 63 | 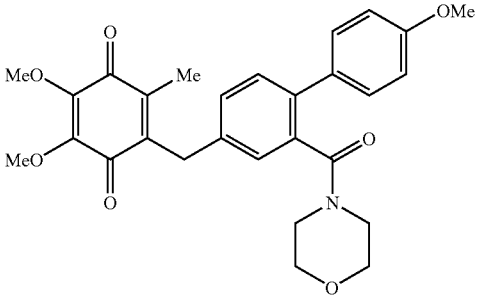 | Yellow crystals 64–66° C. | 492 (M$^+$+ 1) 154 (100) | 2.10(3H, s), 2.45–2.60(1H, m), 2.60– 2.75(1H, m), 2.80–3.00(1H, m), 3.20– 3.30(2H, m), 3.35–3.50(1H, m), 3.55– 3.65(1H, m), 3.65–3.75(1H, m), 3.84(1H, d, J=14Hz), 3.84(3H, s), 3.92(1H, d, J=14Hz), 4.00(3H, s), 4.01(3H, s), 6.93 (2H, d, J=8.6Hz), 7.17(1H, s), 7.20–7.30 (2H,m), 7.35(2H. d, J=8.6Hz) | 1639, 1611 (KBr) |
| 64 | 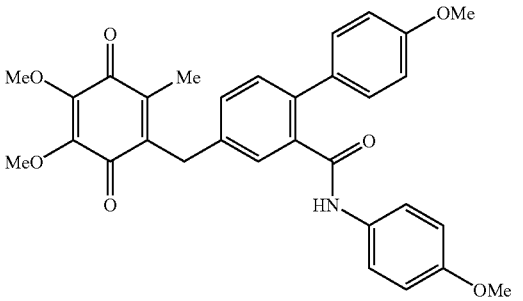 | Yellow crystals 159–160° C. | 528 (M$^+$+ 1) 154 (100) | 2.13(3H, s), 3.76(3H, s), 3.82(3H, s), 3.92(2H. s), 4.00(3H, s), 4.01(3H, s), 6.77(2H, d, J=8.9 Hz), 6.79(1H, s), 6.95 (2H, d, J=8.6Hz), 7.04(2H, d, J=8.9Hz), 7.20–7.40(4H, m), 7.62(1 H, s) | 1643, 1611 (KBr) |

TABLE 24-continued

| Ex. No. | Structure | Property | FABMS (m/z) | NMR(CDCl₃, δ) | IR (cm⁻¹) |
|---|---|---|---|---|---|
| 65 | 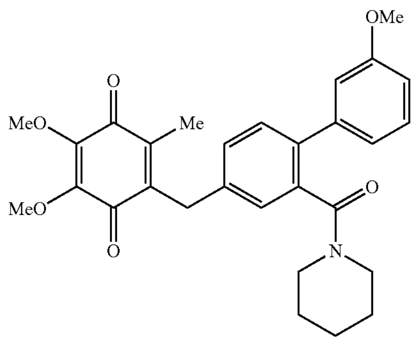 | Yellow crystals 46–48° C. | 490 (M⁺+ 1) 154 (100) | 0.50–0.65(1H, m), 1.05–1.60(5H, m), 2.10(3H, s), 2.65–2.95(2H, m), 3.30–3.45 (1H, m), 3.55–3.70(1H, m), 3.84(1H, d, J=14.0Hz), 3.93(1H, d, J=14.0 Hz), 4.00 (3H, s), 4.01(3H, s), 6.80–6.95(1H, m), 6.95–7.10(2H, m), 7.15(1H, s), 7.20–7.40 (3H, m) | 1612 (KBr) |
| 66 | 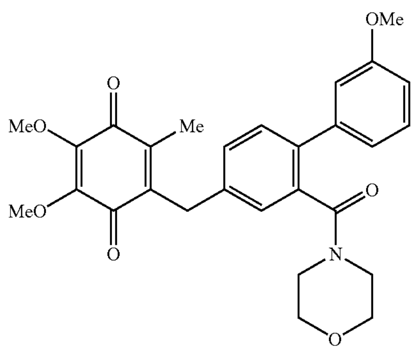 | Yellow crystals 63–65° C. | 4.92 (M⁺+ 1) 154 (100) | 2.11(3H, s), 2.40–2.55(1H, m), 2.65–2.80 (1H, m), 2.90–3.00(1H, m), 3.15–3.35 (2H, m), 3.35–3.50(1H, m), 3.55–3.90(2H, m), 3.81(3H, s), 3.85(1H, d, J=14.0Hz), 3.93 (1H, d, J=14.0Hz), 4.00(3H, s), 4.01(3H, s), 6.85–7.05(3H, m), 7.18(1H, s), 7.20–7.40(3H, m) | 1611 (KBr) |

TABLE 25

| Ex. No. | Structure | Property | FABMS (m/z) | NMR(CDCl₃, δ) | IR (cm⁻¹) |
|---|---|---|---|---|---|
| 67 | 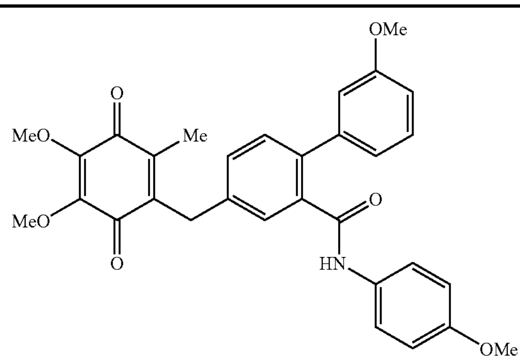 | Yellow crystals 152–155° C. | 528 (M⁺+ 1) 154 (100) | 2.14(3H, s), 3.75(6H, s), 3.93(2H, s), 4.00(3H, s), 4.01(3H, s), 6.77(2H, d, J=8.9Hz), 6.70–6.85(1H, m), 6.85–7.05 (5H, m), 7.25–7.40(3H, m), 7.64(1H, s) | 1648, 1604 (KBr) |
| 68 | 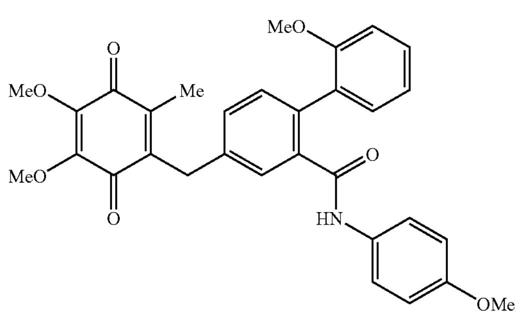 | Yellow crystals 147–148° C. | 528 (M⁺+ 1) 154 (100) | 2.15(3H, s), 3.66(3H, s), 3.75(3H, s), 3.93(2H, s), 4.00(3H, s), 4.01(3H, s), 6.75(2H, d, J=9.0Hz), 6.90(1H, d, J=8.2 Hz), 7.00–7.10(3H, m), 7.15(1H, s), 7.20–7.40(4H, m), 7.69(1H, s) | 1648, 1611 (KBr) |

TABLE 25-continued

| Ex. No. | Structure | Property | FABMS (m/z) | NMR(CDCl$_3$, δ) | IR (cm$^{-1}$) |
|---|---|---|---|---|---|
| 69 | 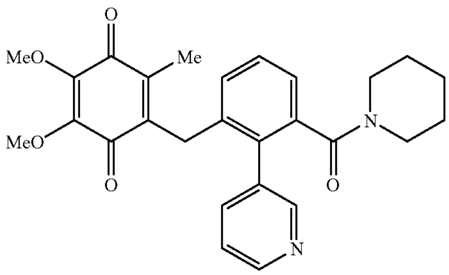 | Yellow oil | 461 (M$^+$+ 1) 154 (100) | 1.10–1.75(6H, s), 1.83(3H, s), 280–3.00 (1H, m), 3.35–3.70(2H, m), 3.82(1H, d, J=15.6Hz), 3.97, 3.99(6H, each s), 690– 7.50(4H, m), 7.65–7.90(1H, m), 8.55–8.75(2H, m) | 1648, 1612 (CHCl3) |
| 70 | 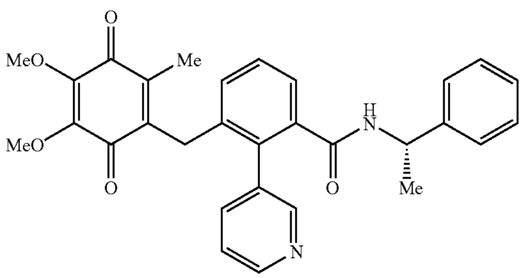 | Yellow oil | 497 (M$^+$+ 1) 154 (100) | 1.16, 1.25(3H, each d, J=6.8Hz), 1.84, 1.86(3H, each s), 3.40–3.70(2H, m), 3.96 (3H, s), 3.99(3H, s), 4.90–5.05(1H, m), 5.40–5.60(1H, m), 6.90–7.20(3H, m), 7.20–7.40(5H, m), 7.40–7.55(1H, m), 7.74(1H, t-like), 8.55–8.70(2H, m) | 1652, 1611 (CHCl3) |

TABLE 26

| Ex. No. | Structure | Property | FABMS (m/z) | NMR(CDCl$_3$, δ) | IR (cm$^{-1}$) |
|---|---|---|---|---|---|
| 71 | 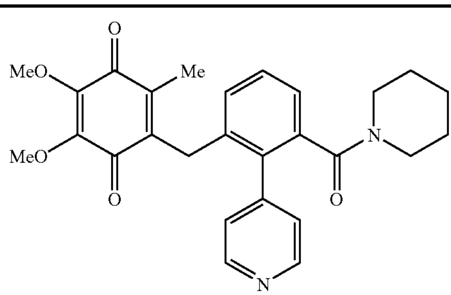 | Yellow oil | 461 (M$^+$+ 1, 100) | 1.05–1.75(6H, m), 1.84(3H, s), 2.75–2.95 (1H, m), 3.00–3.25(2H, m), 3.43(1H, d, J=15.7Hz), 3.50–3.65(1H, m), 3.83(1H, d, J=15.7Hz), 3.99(3H, s), 4.00(3H, s), 6.99(1H, d, J=7.8Hz), 7.19(1H, d, J=7.6 Hz), 7.25–7.50(2H, m), 8.60–8.85(2H, m) | 1648, 1612 (CHCl3) |
| 72 | 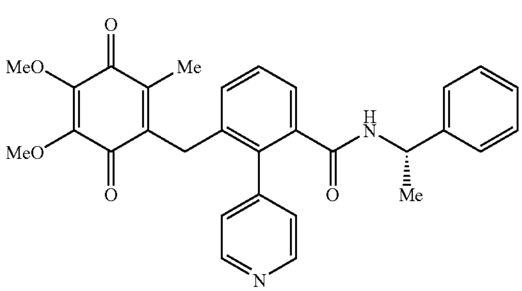 | Yellow oil | 497 (M$^+$+ 1) 154 (100) | 1.22(3H, d, J=6.9Hz), 1.86(3H, s), 3.45– 3.65(2H, m), 3.96(3H, s), 3.99(3H, s), 4.90–5.05(1H, m), 5.46(1H, d, J=80Hz) 6.95–7.05(2H, m), 7.20–7.50(8H, m), 8.55–8.70(2H, m) | 1652, 1611 (CHCl3) |
| 73 | 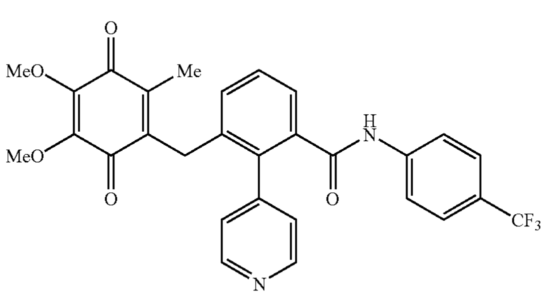 | Yellow crystals 144–146° C. | 537 (M$^+$ + 1) 154 (100) | 1.91(3H, s), 3.62(2H, s), 3.98(3H, s), 4.01(3H, s), 7.05–7.20(2H, m), 7.25–7.65 (8H, m), 8.70(2H, d, J=5.7Hz) | 1654, 1608 (KBr) |

TABLE 26-continued

| Ex. No. | Structure | Property | FABMS (m/z) | NMR(CDCl₃, δ) | IR (cm⁻¹) |
|---|---|---|---|---|---|
| 74a | 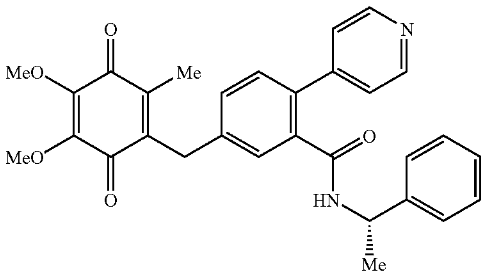 | Yellow crystals 124–126° C. | 497 (M⁺ + 1) 154 (100) | 1.29(3H, d), 2.11(3H, s), 3.90(2H, s), 4.00(6H, s), 5.00–5.15(1H, m), 5.49(1H, d), 6.95–7.10(2H, m), 7.20–7.40(7H, m), 7.43(1H, s), 8.51(2H, d) | 1642, 1611 (KBr) |

TABLE 27

| Ex. No. | Structure | Property | FABMS (m/z) | NMR(CDCl₃, δ) | IR (cm⁻¹) |
|---|---|---|---|---|---|
| 74b | 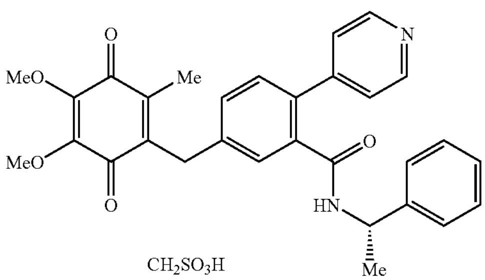 | Yellow crystals 156–158° C. | 497 (M⁺+ 1) 154 (100) | 1.48(3H, d), 2.13(3H, s), 2.82(3H, s), 3.93(2H, s), 4.00(3H, s), 4.01(3H, s), 5.00–5.20(1H, m), 6.55(1H, d), 7.10–7.50 (8H, m), 7.67(2H, d), 8.49(2H, d) | 1638, 1611 (KBr) |
| 75a | 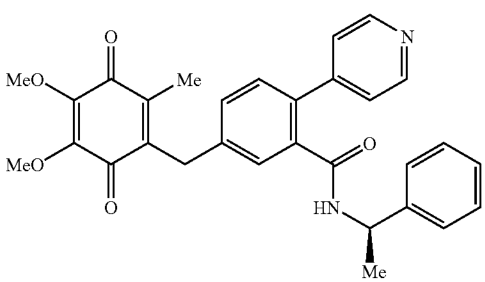 | Yellow crystals 102–103° C. | 497 (M⁺+ 1) 154 (100) | 1.29(3H, d, J=6.9Hz), 2.11(3H, s), 3.90 (2H, s), 3.99(6H, s), 5.00–5.15(1H, m), 5.51(1H, d, J=7.9Hz), 6.95–7.05(2H, m), 7.15–7.35(7H, m), 7.43(1H, s), 8.51(2H, d, J=5.4Hz) | 1654 (KBr) |
| 75b | 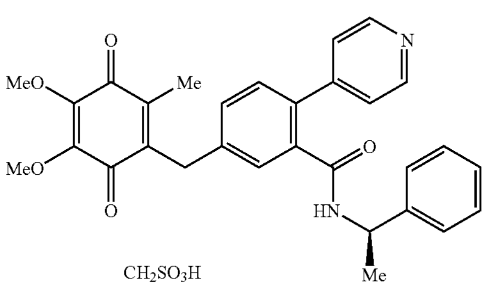 | Yellow crystals 157–159° C. | 497 (M⁺+ 1) 154 (100) | 1.48(3H, d, J=7.0Hz), 2.13 (3H, s), 2.84 (3H, s), 3.93(3H, s), 4.00(3H, s), 4.01 (3H, s), 5.05–5.20(1H, m), 6.58(1H, d, J=8.1Hz), 7.10–7.40(8H, m), 7.69(2H, d, J=5.1Hz), 8.48(2H, d, J=4.8Hz) | 1638 (KBr) |

TABLE 27-continued

| Ex. No. | Structure | Property | FABMS (m/z) | NMR(CDCl$_3$, δ) | IR (cm$^{-1}$) |
|---|---|---|---|---|---|
| 76a | 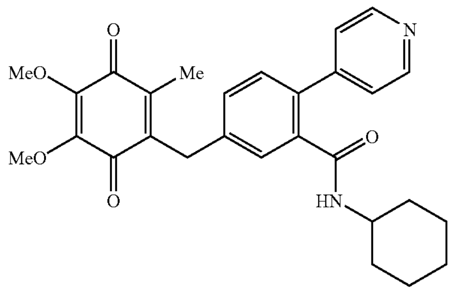 | Yellow crystals 149–150° C. | 497 (M$^+$+ 1) 154 (100) | 0.70–0.90(2H, m), 0.95–1.15(1H, m), 1.15–1.35(2H, m), 1.45–1.75(5H, m), 2.12(3H, s), 3.65–3.85(1H, m), 3.91(2H, s), 4.01(6H, s), 5.05(1H, d, J=8.3 Hz), 7.15–7.35(4H, m), 7.42(1H, d-like), 8.63 (2H, d-like) | 1638, 1611 (KBr) |

TABLE 28

| Ex. No. | Structure | Property | FABMS (m/z) | NMR(CDCl$_3$, δ) | IR (cm$^{-1}$) |
|---|---|---|---|---|---|
| 76b | 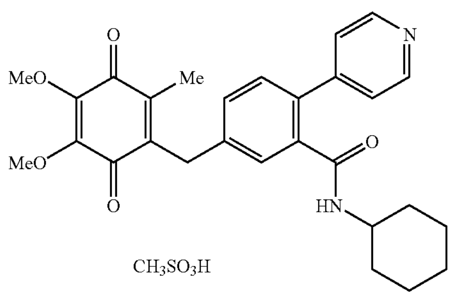 | Yellow crystals 180–184° C. | 475 (M$^+$+ 1) 154 (100) | 1.00–1.50(5H, m), 1.55–2.00(5H, m), 2.14(3H, s), 2.86(3H, s), 3.65–3.90(1H, m), 3.94(2H, s), 4.01(6H, s), 5.96(1H, d, J=8.0Hz), 7.20–7.50(3H, m), 7.89(2H, d-like), 8.81(2H, d-like) | 1639, 1609 (KBr) |
| 77a | 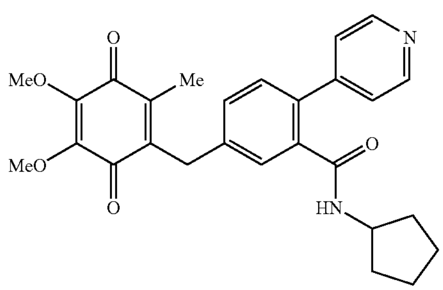 | Yellow crystals 143–144° C. | 461 (M$^+$+ 1) 154 (100) | 0.95–1.10(2H, m), 1.30–1.55(4H, m), 1.70–1.90(2H, m), 2.12(3H, s), 3.91(2H, s), 4.01(6H, s), 4.10–4.25(1H, m), 5.09 (1H, d, J=7.7Hz), 7.20–7.40(4H, m), 7.42 (1H, s), 8.63(2H. d-like) | 1642, 1609 (KBr) |
| 77b | 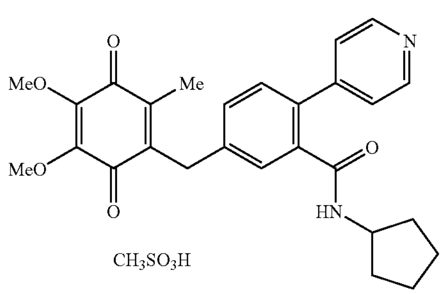 | Yellow crystals 173–716° C. | 461 (M$^+$+ 1) 154 (100) | 1.20–1.45(2H, m), 1.50–1.70(4H, m), 1.85–2.05(2H, m), 2.14(3H, s), 2.82(3H, s), 3.93(2H, s), 4.01(6H, s), 4.10–4.25 (1H, m), 6.23(1H, d, J=7.2 Hz), 7.32(1H, d, J=7.9Hz), 7.39(1H, d, J=8.0 Hz), 7.44 (1H, s), 7.92(2H, d, J=5.8Hz), 8.81(2H, d, J=5.8 Hz) | 1638, 1610 (KBr) |

TABLE 28-continued

| Ex. No. | Structure | Property | FABMS (m/z) | NMR(CDCl$_3$, δ) | IR (cm$^{-1}$) |
|---|---|---|---|---|---|
| 78a | 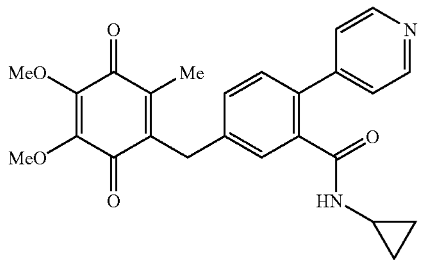 | Yellow crystals 152–154° C. | 433 (M$^+$+ 1) 154 (100) | 1.10–1.25(2H, m), 1.60–1.75(2H, m), 2.12(3H, s), 2.55–2.70(1H, m), 3.90 (2H, s), 4.01(6H, s), 5.38(1H, br s), 7.20–7.45 (5H, m), 8.62(2H, d-like) | 1638, 1611 (KBr) |

TABLE 29

| Ex. No. | Structure | Property | FABMS (m/z) | NMR(CDCl$_3$, δ) | IR (cm$^{-1}$) |
|---|---|---|---|---|---|
| 78b | CH$_3$SO$_3$H | Yellow crystals 181–183° C. | 433 (M$^+$+ 1) 154 (100) | 1.40–1.60(2H, m), 1.70–1.85(2H, m), 2.13(3H, s), 2.78(3H, s), 2.65–2.75(1H, m), 3.92(2H, s), 4.01(6H, s), 6.70(1H, d-like), 7.31(1H, d, J=8.0Hz), 7.39(1H, d, J=8.1Hz), 7.44(1H, s), 7.92(2H, d, J=5.7 Hz), 8.79(2H, d, J=5.8Hz) | 1641 (KBr) |
| 79a | 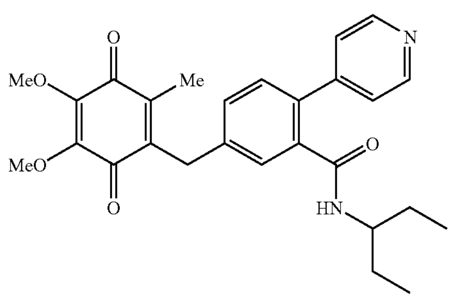 | Yellow crystals 155–156° C. | 463 (M$^+$+ 1) 154 (100) | 0.68(6H, t), 1.10–1.45(4H, m, 2.12(3H, s), 3.70–3.85(1H, m), 3.91(2H, s), 4.01 (6H, s). 5.07(1H, d), 7.20–7.45(5H, m), 8.61(2H, d, J=5.9 Hz) | 1748 (KBr) |
| 79b | CH$_3$SO$_3$H | Yellow crystals 205–206° C. | 463 (M$^+$+ 1) 154 (100) | 0.85(6H, t), 1.30–1.65(4H, m), 2.14(3H, s), 2.84(3H, s), 3.70–3.80(1H, m), 3.94 (2H, s), 4.01(6H, s), 5.96(1H, d, J=8.9Hz), 7.32(1H, d, J=7.9Hz), 7.40(1H, d, J=8.1Hz), 7.45(1H, s), 7.91(2H, d, J= 6.2Hz), 8.79(2H, d, J=6.2Hz) | 1638 1612 (KBr) |

Experimental Example 1

Effects of Compounds on Human Lung Cancer A549 Cells (A549/NF-κBLuc) Stably Transfected with Luciferase Plasmid (pNFκB-Luc, Stratagene, U.S.A.) Having the NF-κB Regulatory Sequence Using lipofectamine (Lifetech Oriental K.K., Tokyo), pNFκB-Luc were cotransfected with pSV2neo (Clontech, U.S.A.) into A549 cells (ATCC CCL185) according to the conventional method, and A549/NF-κBLuc stably transfected with pNFκB-Luc were selected by adding G418 sulfate (1 mg/ml, Lifetech Oriental K.K.) to the culture medium.

A compound prepared in an Example was added to A549/NF-κBLuc, then IL-1β which was able to activate the NF-κB was added at 1 hour thereafter and incubation was continued for 3 hours more. It has been made clear by using a luciferase activity as an index that the compound obtained in the Example suppresses the activation of NF-κB by stimulated with IL-1β. The $IC_{50}$ values are shown in the Table.

TABLE 30

| Compound | $IC_{50}$ value |
|---|---|
| Example 12 | toxic |
| Example 14 | >15 μg/ml |
| Example 15 | >15 μg/ml |
| Example 17 | >15 μg/ml |
| Example 18 | >15 μg/ml |
| Example 35 | >15 μg/ml |
| Example 36 | >15 μg/ml |
| Example 37 | >45 μg/ml |
| Example 38 | >45 μg/ml |
| Example 39 | >30 μg/ml |
| Example 40 | >45 μg/ml |
| Example 45 | >30 μg/ml |
| Example 47 | 24 μg/ml |
| Example 48 | >30 μg/ml |
| Example 49 | 24 μg/ml |
| Example 51 | >30 μg/ml |
| Example 52 | >45 μg/ml |
| Example 53 | >30 μg/ml |
| Example 54 | 15 μg/ml (33 μM) |
| Example 55 | >45 μg/ml |
| Example 56 | >45 μg/ml |
| Example 57 | >30 μg/ml |
| Example 58a | 15 μg/ml (30 μM) |
| Example 58b | 45 μg/ml (81 μM) |
| Example 59 | >45 μg/ml |
| Example 60a | >30 μg/ml |
| Example 60b | >30 μg/ml |
| Example 61 | >30 μg/ml |
| Example 64 | 12 μg/ml (23 μM) |
| Example 65 | 40 μg/ml (82 μM) |

TABLE 31

| Compound | $IC_{50}$ value |
|---|---|
| Example 66 | 42 μg/ml (85 μM) |
| Example 67 | >45 μg/ml |
| Example 68 | >45 μg/ml |
| Example 73 | >30 μg/ml |
| Example 74a | >45 μg/ml |
| Example 74b | >45 μg/ml |
| Example 75a | >45 μg/ml |
| Example 75b | >45 μg/ml |
| Example 76a | >45 μg/ml |
| Example 76b | >45 μg/ml |
| Example 77a | >45 μg/ml |
| Example 77b | >45 μg/ml |
| Example 78a | >45 μg/ml |
| Example 78b | >45 μg/ml |
| Example 79a | >45 μg/ml |
| Example 79b | >45 μg/ml |

The invention claimed is:

1. A substituted benzoic acid derivative represented by the following formula (I):

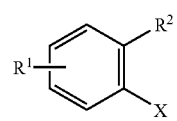

wherein $R^1$ is the following formula (II):

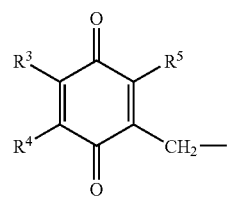

or the following formula (III):

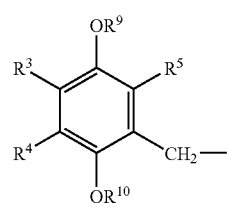

wherein $R^3$, $R^4$ and $R^5$ each independently represents a hydrogen atom, an alkyl group having 1 to 6 carbon(s) or an alkoxy group having 1 to 6 carbon(s); $R^9$ and $R^{10}$ each independently represents a hydrogen atom, an alkyl group having 1 to 6 carbon(s) or an acyl group having 2 to 11 carbons;

$R^2$ represents an optionally-substituted aromatic hydrocarbon group or an optionally-substituted heterocyclic group; and X represents a carboxyl group which may be esterified or amidated.

2. The substituted benzoic acid derivative according to claim 1, wherein $R^1$ is the following formula (II):

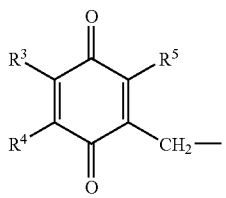

wherein $R^3$ and $R^4$ each independently represents a hydrogen atom, a methyl group or a methoxy group.

3. The substituted benzoic acid derivative according to claim 1, wherein $R^1$ is the following formula (II):

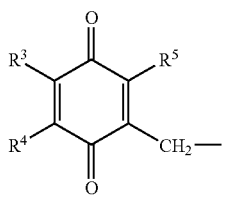

wherein $R^5$ represents a hydrogen atom or a methyl group.

4. The substituted benzoic acid derivative according to claim 1, wherein $R^2$ is an optionally substituted aryl group having 6 to 12 carbons or an optionally substituted heteroaryl group having 4 to 11 carbons.

5. The substituted benzoic acid derivative according to claim 1, wherein $R^2$ is a phenyl group, a 4-methoxyphenyl group, a 3-methoxyphenyl group, a 2-methoxyphenyl group, a 3,4-dimethoxyphenyl group, a 4-pyridyl group, a 3-pyridyl group, a 2-pyridyl group, a 2-furanyl group or a 3-furanyl group.

6. The substituted benzoic acid derivative according to claim 1, wherein X is a group —COOR$^6$, wherein $R^6$ represents a hydrogen atom, an optionally substituted alkyl group having 1 to 6 carbon(s) or an optionally substituted aralkyl group having 7 to 14 carbons.

7. The substituted benzoic acid derivative according to claim 1, wherein X is a group —CONR$^7$R$^8$, wherein $R^7$ and $R^8$ each independently represents a hydrogen atom, an optionally-substituted alkyl group having 1 to 6 carbon(s), an optionally-substituted aryl group having 6 to 12 carbons, an optionally-substituted heteroaryl group having 4 to 11 carbons, an optionally-substituted aralkyl group having 7 to 14 carbons or an optionally-substituted heteroarylalkyl group having 5 to 13 carbons, or $R^7$ and $R^8$ together with the nitrogen atom to which they are attached, represents a heterocyclic ring which may further contain a nitrogen atom, oxygen atom or sulfur atom or may be condensed.

8. The substituted benzoic acid derivative according to claim 1, wherein X is a group —CONR$^7$R$^8$, wherein $R^7$ and $R^8$ together with the nitrogen atom to which they are attached, represents a five to eight-membered nitrogen-containing heterocyclic ring which may further contain 1 to 3 hetero atom(s) selected from nitrogen atom, oxygen atom and sulfur atom where carbon atom or sulfur atom on the ring may be in a form of an oxide.

9. The substituted benzoic acid derivative according to claim 1, which is represented by the following formula (I):

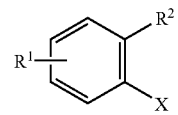

wherein $R^1$ is the following formula (II):

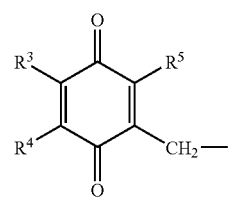

wherein $R^3$ and $R^4$ each represents a methyl group or a methoxy group and $R^5$ represents a methyl group; $R^2$ represents a phenyl group, a 4-methoxyphenyl group, a 3-methoxyphenyl group, a 2-methoxyphenyl group, a 3,4-dimethoxyphenyl group, a 4-pyridyl group, a 3-pyridyl group, a 2-pyridyl group, a 2-furanyl group or a 3-furanyl group; and X represents a carboxyl group which may be esterified or amidated.

10. A pharmaceutical composition of matter comprising a substituted benzoic acid derivative according to claim 1, or a pharmaceutically acceptable salt thereof, and a pharmaceutically acceptable carrier.

* * * * *